US007491799B2

(12) United States Patent
Steward et al.

(10) Patent No.: US 7,491,799 B2
(45) Date of Patent: *Feb. 17, 2009

(54) MODIFIED BOTULINUM NEUROTOXINS

(75) Inventors: Lance E. Steward, Irvine, CA (US); Ester Fernandez-Salas, Fullerton, CA (US); Todd M. Herrington, Brookline, MA (US); Kei Roger Aoki, Coto de Caza, CA (US)

(73) Assignee: Allergan, Inc., Irvine, CA (US)

( * ) Notice: Subject to any disclaimer, the term of this patent is extended or adjusted under 35 U.S.C. 154(b) by 407 days.

This patent is subject to a terminal disclaimer.

(21) Appl. No.: 10/757,077

(22) Filed: Jan. 14, 2004

(65) Prior Publication Data

US 2004/0220386 A1    Nov. 4, 2004

Related U.S. Application Data

(63) Continuation-in-part of application No. 10/163,106, filed on Jun. 4, 2002, which is a continuation-in-part of application No. 09/910,346, filed on Jul. 20, 2001, now abandoned, which is a continuation-in-part of application No. 09/620,840, filed on Jul. 21, 2000, now Pat. No. 6,903,187.

(51) Int. Cl.
    *C07K 14/33* (2006.01)
(52) U.S. Cl. .................................... 530/350
(58) Field of Classification Search ................ None
    See application file for complete search history.

(56) References Cited

U.S. PATENT DOCUMENTS

| 4,932,936 | A | 6/1990 | Dykstra et al. |
|---|---|---|---|
| 5,053,005 | A | 10/1991 | Borodic |
| 5,437,291 | A | 8/1995 | Pasricha et al. |
| 5,670,484 | A | 9/1997 | Binder |
| 5,714,468 | A | 2/1998 | Binder |
| 5,714,986 | A | 2/1998 | Dao |
| 5,721,215 | A | 2/1998 | Aoki et al. |
| 5,766,605 | A | 6/1998 | Sanders et al. |
| 5,939,070 | A | 8/1999 | Johnson et al. |
| 5,989,545 | A | 11/1999 | Foster et al. |
| 6,063,768 | A | 5/2000 | First |
| 6,113,915 | A | 9/2000 | Aoki et al. |
| 6,139,845 | A | 10/2000 | Donovan |
| 6,143,306 | A | 11/2000 | Donovan |
| 6,265,379 | B1 | 7/2001 | Donovan |
| 6,299,893 | B1 | 10/2001 | Schwartz et al. |
| 6,306,403 | B1 | 10/2001 | Donovan |
| 6,306,423 | B1 | 10/2001 | Donovan |
| 6,312,708 | B1 | 11/2001 | Donovan |
| 6,328,977 | B1 | 12/2001 | Donovan |
| 6,358,513 | B1 | 3/2002 | Voet et al. |
| 6,365,164 | B1 | 4/2002 | Schmidt |
| 6,395,277 | B1 | 5/2002 | Graham |
| 6,423,319 | B1 | 7/2002 | Brooks et al. |
| 6,458,365 | B1 | 10/2002 | Aoki et al. |
| 6,464,986 | B1 | 10/2002 | Aoki et al. |
| 2003/0027752 | A1 | 2/2003 | Steward et al. ............ 514/12 |
| 2003/0219462 | A1 | 11/2003 | Steward et al. ........... 424/239.1 |

FOREIGN PATENT DOCUMENTS

| WO | WO94/15629 | 7/1994 |
|---|---|---|
| WO | WO 96/39166 | 12/1996 |
| WO | WO 97/32599 | 9/1997 |
| WO | WO 00/05252 | 2/2000 |
| WO | WO 02/08268 A2 | 1/2002 |

OTHER PUBLICATIONS

Rudinger, In "Peptide Hormones" (ed. J.A. Parsons), University Park Press, Baltimore, pp. 1-7 (1976).*
Adenis, et al., J. Fr. Ophthamol. (1990) 13:259-264. (Abstract only in English).
Binz, et al., J. Biol. Chem. (1990) 265:9153-9158.
Blitzer, et al., Ann. Otol. Rhinol Laryngol. (1985) 94:591-594.
Brin, et al., Advances in Neurology, vol. 50: Dystonia 2 (1988), pp. 599-608.
Di Bello, et al., Eur. J. Biochem. (1994) 219:161-169.
Cohn, et al., Neurology (1987) 37 (3 Supp. 1):123-124. (abstract only).
Elston, et al., Br. J. Opthamol. (1985) 69:718-724.
Elston, et al., Br. J. Opthamol. (1985) 69:891-896.
Galli, et al., Cell (1998) 9:1437-1448.
Jancovic, et al., Neurology (1987) 37:616-623.
Li, et al., Biochemistry (1994) 33:7014-7020.
Maisey, et al., Eur. J. Biochem. (1988) 177:683-691.
Martinez-Arca, et al., J. Cell Biol. (2000) 149:889-899.
Milton, et al., Biochemistry (1992) 31:8799-8809.
Minton, In Clostridial Neurotoxins: the molecular pathogenesis of tetanus and botullsm,Montecucco, ed., Springer Verlag, NY, 1995, pp. 161-194.
Swain, et al., Peptide Res. (1993) 6:147-154.
Zhou, et al., Biochemistry (1995) 34:15175-15181.
Shin, et al., J. Biol. Chem. (1991) 266:10658-10665.
Rasiborska and Charlton, Can. J. Physiol. (1999) 77:679-688.
Erdal, et al., Arch. Pharmacol. (1995) 351:67-78.
Ragona, et al., The Larangyscope (1999) 109:1344-1346.
Naumann, et al., Eur. J. Neurol. (1999) 6:S111-S115.
Keller, et al., FEBS Lett. (1999) 456:137-142.
Dietrich, et al., J. Cell. Biol. (1997) 138:271-281.
Geisler, et al., J. Biol. Chem. (1998) 273:21316-21323.

(Continued)

*Primary Examiner*—Robert C Hayes
(74) *Attorney, Agent, or Firm*—Dean G. Stathakis; Joel B. German; Martin A. Voet

(57) ABSTRACT

Natural and modified neurotoxins and isolated neurotoxin compositions are described. The neurotoxins may include one or more structural modifications, wherein the structural modification(s) alters the biological persistence, such as the biological half-life and/or a biological activity of the modified neurotoxin relative to an identical neurotoxin without the structural modification(s). In one embodiment, methods of making the modified neurotoxin include using recombinant techniques. In some embodiments, methods of using the modified neurotoxin to treat conditions include treating various disorders, neuromuscular ailments and pain.

3 Claims, 36 Drawing Sheets

OTHER PUBLICATIONS

Tan, et al., J. Biol. Chem. (1998) 273:17351-17360.
Liu, et al., Trends Cell Biol. (1999) 9:356-363.
Cai and Singh, Biochemistry (2001) 40:4693.
Tikkanen, et al., Traffic (2000) 1:631-640.
Rapaport, et al., EMBO J. (1998) 17:2148-2155.
Miranda, et al., JBC Papers in Press (2001) 1-35.
Cowles, et al., Cell (1997) 91:109-118.
Aoki, et al., J. Neurol. (2001) 248 (Supp 1):3-10.
Aoki, Toxicon, (2001) 12:1815-1820.
Wiegand, et al., Nauny Schmiedberg's Arch. Pharmacol. (1976) 292.
Haberman, Nauny Schmiedberg's Arch. Pharmacol. (1974) 281.
Thompson, et al., Eur. J. Biochem. (1990) 189:73.
Arnon, et al., "Botulinum toxin as a biological weapon: medical and public health management," JAMA (2001) 285:1059-1070.
Eswaramoorthy, et al., "A novel mechanism for Clostridium botulinum neurotoxin inhibition," Biochemistry (2002) 41:9795-9802.
Aoki, et al., "Is the light chain subcellular localization an important factor for botulinum neurotoxin duration of action?," Naunyn Schmiedebergs Arch. Pharmacol. (2002) 385 (Suppl 2):R10.
Fernandez-Salas, et al., "Localization of BoNT light chains in neuronal and non-neuronal cell lines, implications for the duration of action of the different serotypes," Naunyn Schmiedebergs Arch. Pharmacol. (2002) 365 (Suppl 2):R19.
Steward, et al., "BoNT/A light chain and the dileucine motif: potential implications for light chain localization and neurotoxin duration of action," Naunyn Schmiedebergs Arch. Pharmacol. (2002) 385 (Suppl 2):R44.
Fernandez-Salas, et al., "Plasma Membrane Localization Signals in the Light Chain of Botulinum Neurotoxin," Slide presentation at USAMROD, Jan. 2004.
Fernandez-Salas, et al., "Plasma membrane localization signals in the light chain of botulinum neurotoxin," Proc. Natl. Acad. Sci. USA (2004) 101:3208-3213.
Fernandez-Salas, et al., "Is the light chain subcellular localization an important factor in Botulinum toxin duration of action?" Movement Disorders (2004) 19:S23-S34.
Fernandez-Salas, E., et al., *Plasma membrane localization signals in the light chain of botulinum neurotoxin serotype A*, Society of Neuroscience Abstract Viewer and Itinerary Planner, vol. 2003; pp. Abstract No. 9.2.
Foran, Patrick G., et al., *Evaluation of the therapeutic usefulness of botulinum neurotoxin B, C1, E, and F compared with the long lasting type A. Basis for distinct durations of inhibition of exocytosis in central neurons*, Journal of Biological Chemistry, vol. 278, No. 2, Jan. 10, 2003, pp. 1363-1371.
Wang Xingmin, et al., *Genetic analysis of type E botulinum toxin-producing Clostridium butyricum strains*, Applied and Environmental Microbiology, vol. 66, No. 11, Nov. 2000, pp. 4992-4997.
Fernandez-Salas, E., et al., *Plasma membrane localization signals in the light chain of botulinum neurotoxin*, Proceedings of the National Academy of Sciences of the United States of America, Mar. 2, 2004, vol. 101, No. 9, pp. 3208-3213.
Zhou et al., "Expression and purification of the light chain of botulinum neurotoxin A: A single mutation abolishes its cleavage of SNAP-25 and neurotoxicity after reconstruction with the heavy chain", Biochemistry, vol. 34, No. 46, pp. 15175-15181, 1995.
Darsow et al, J. Cell Biol. (1998) 142-913-922.
Fauci et al, Harrison's Principles of Internal Medicine 14th Edition, (1998), McGaw Hill- (table of contents only).
Kadhodayan et al, Protein Express (2000) 19: 125-130.
Kozaki et al, J. Med. Sci Biol. (1981) 34:61-68.
Lacy et al, Biochemistry (1994) 33: 7014-7020.
Peden et al, J. Biol. Chem. (2001) 276-49183-49187.
Press Release, "Protein Turnover and Autophagy", American Society for Cell Biology, Jan. 1, 1990.

* cited by examiner

```
  1 PFVNKQENYK DPVNGVDIAY IKIPNVGQMQ PVKAFKIHNK IWVIPERDTF
 51 TNPEEGDLNP PPEAKQVPVS YYDSTYLSTD NEKDNYLKGV TKLFERIYST
101 DLGRMLLTSI VRGIPFWGGS TIDTELKVID TNCINVIQPD GSYRSEELNL
151 VIIGPSADII QFECKSFGHE VLNLTRNGYG STQYIRFSPD FTFGFEESLE
201 VDTNPLLGAG KFATDPAVTL AHELIHAGHR LYGIAINPNR VFKVNTNAYY
251 EMSGLEVSFE ELRTFGGHDA KFIDSLQENE FRLYYYNKFK DIASTLNKAK
301 SIVGTTASLQ YMKNVFKEKY LLSEDTSGKF SVDKLKFDKL YKMLTEIYTE
351 DNFVKFFKVL NRKTYLNFDK AVEKINIVPK VNYTIYDGFN LRNTNLAANF
401 NGQNTEINNM NFTKLKNFTG LFEFYKLLCV RGIITSK
```

FIG. 3

Botulinum Toxin     Type A X-Ray Structure

FIG. 6

Yellow = protease domain
Green = binding domain
Red = translocational domain

```
                          1                                                                         75
BoNT-A_HalIA_LC     (1)   -PFVNKQFNYKDPVNGVDIAYIKIPNVG-QMQPVKAFKIHNKIWVIPERDTFTNPEGDLNPPPEAKQVPVSYYD
BoNT-B_Danish_I_LC  (1)   MPVTINNFNYNDPIDNNNIIMMEPPFARGTGRYYKAFKITDRIWIIPERYTFGYKEDFNKSSGIFNRDVCEYYD
Consensus           (1)    P     NFNY DPI    I  I  P           KAFKI  KIWIIPER TF    E               YYD 76                                                                        150
BoNT-A_HalIA_LC     (74)  STYLSTDNEKDNYLKGVTKLFERIYSTDLGRMLLTSIVRGIPEKGGSTIDTELKVIDTNCINVIQPDGSYR-SEE
BoNT-B_Danish_I_LC  (76)  PDYLNTNDKKNIFLQTMIKLFNRIKSKPLGEKLLEMIINGIPYLGDRRVPLEEFNTNIASVTVNKLISNPGEVER
Consensus           (76)    YL T    K   FL  M KLF RI S  LG   LL  II GIPF G     I E          I V          E 151                                                                       225
BoNT-A_HalIA_LC     (148) -----LNLVIIGPSADIIQFECKSFGHEVLNLTRNGYGSTQYIRFSPDFTFGFEESLEVDTNPLLGAGKFATDPA
BoNT-B_Danish_I_LC  (151) KKGIFANLIIFGPGPVLNENETIDIGIQNHFASREGFGIMQMKFCPEYVSVFNNVQENKGASIFNRRGYFSDPA
Consensus           (151)      NLII GP   I   E   G       SR GFG    IKF PDF    F     E    I      F SDPA 226                                                                       300
BoNT-A_HalIA_LC     (218) VTLAHELIHAGHRLYGIALNPNRVFKVNTNAYYEMSGLEVSFEELRTFGGHDAKFIDSLQENEFRLYYYNKFKDI
BoNT-B_Danish_I_LC  (226) LILMHELIHVLHGLYGIKVD-DLPIVPNEKKFFMQSTDAIQAEELYTFGGQDPSIITPSTDKSIYDKVLQNFRGI
Consensus           (226) L L  HELIH  H LYGI I         N    FF  S    I  EEL TFGG D    I     D         N FK I 301                                                                       375
BoNT-A_HalIA_LC     (293) ASTLNKAKSIVG-TTASLQYMKNVFKEKYLLSEDTSGKFSVDKLKFDKLYKMLTEIYTEDNFVKFFKVLNRKTYL
BoNT-B_Danish_I_LC  (300) VDRLNKVLVCISDPNININIYKNKFKDKYKFVEDSEGKYSIDVESFDKLYKSLMFGFTETNIAENYKIKTRASYF
Consensus           (301)    LNK     I        IN  KN  FKDKY    EDS GKFSID    FDKLYK L     FTE N       FXI  R SY 376                                                                       447
BoNT-A_HalIA_LC     (367) NFDKAVFKIN-IVPKVNYTIYDGFNLRNTNLAANFNGQNTEINNMNFTKLKNFTGLFEFYKLLCVRGIITSK
BoNT-B_Danish_I_LC  (375) SDSLPPVKIKNLLDNEIYTIEDGFNISDKDMEKEYRGQNKAINKQAYEEIS--KEHLAVYKIQMCKSVK---
Consensus           (376)        KI  IL      YTI DGFNI       L     F GQN   IN      F   I           YKI    K I
```

FIG. 9

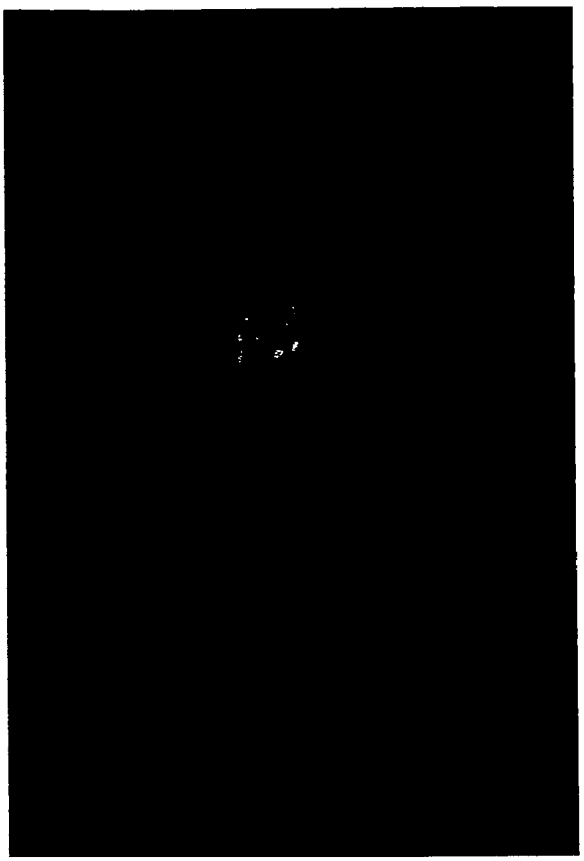
FIG. 17

FIG. 18

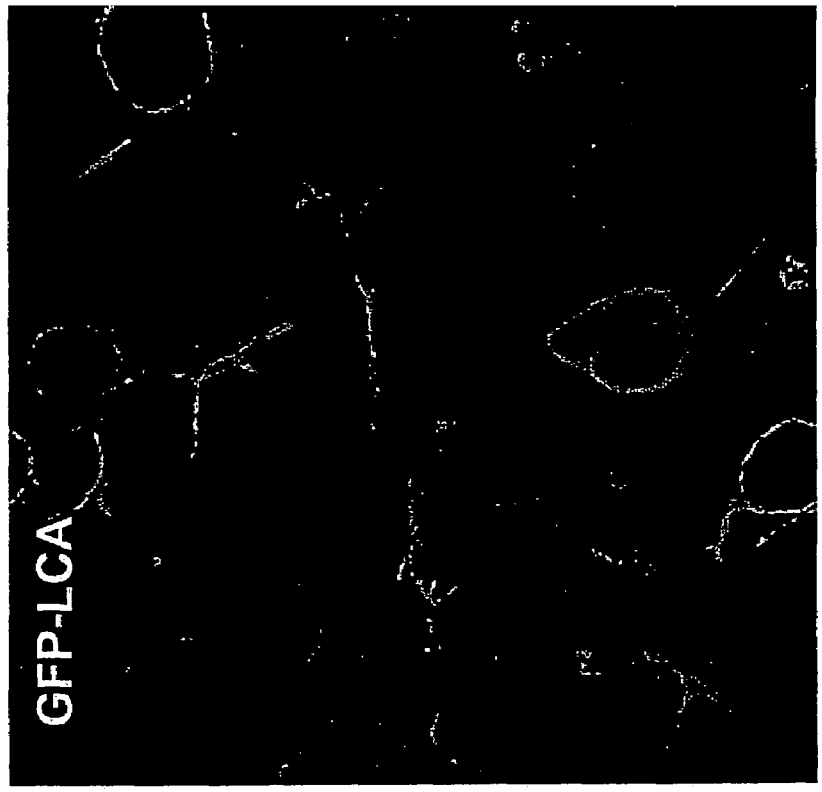
FIG. 21

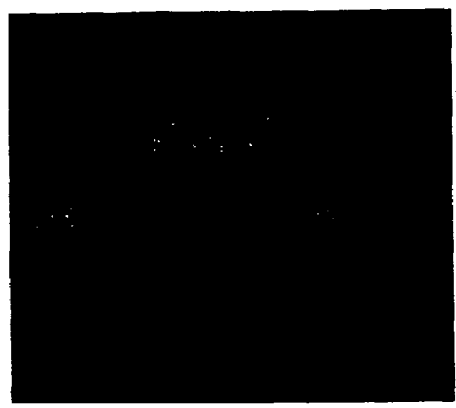
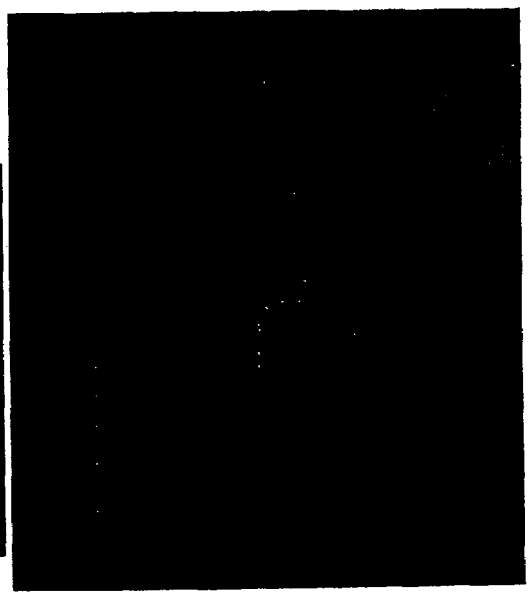
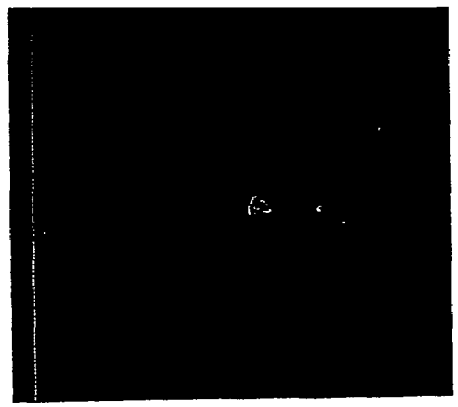
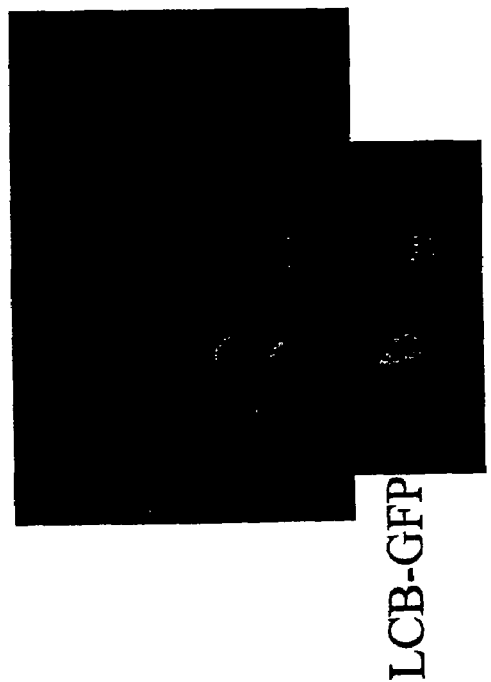
FIG. 22

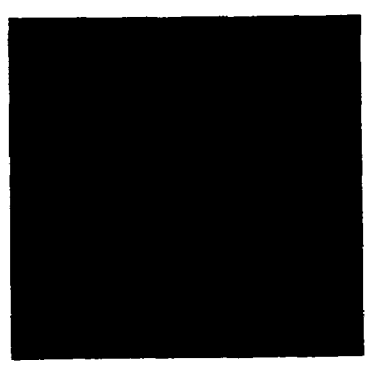
FIG. 23

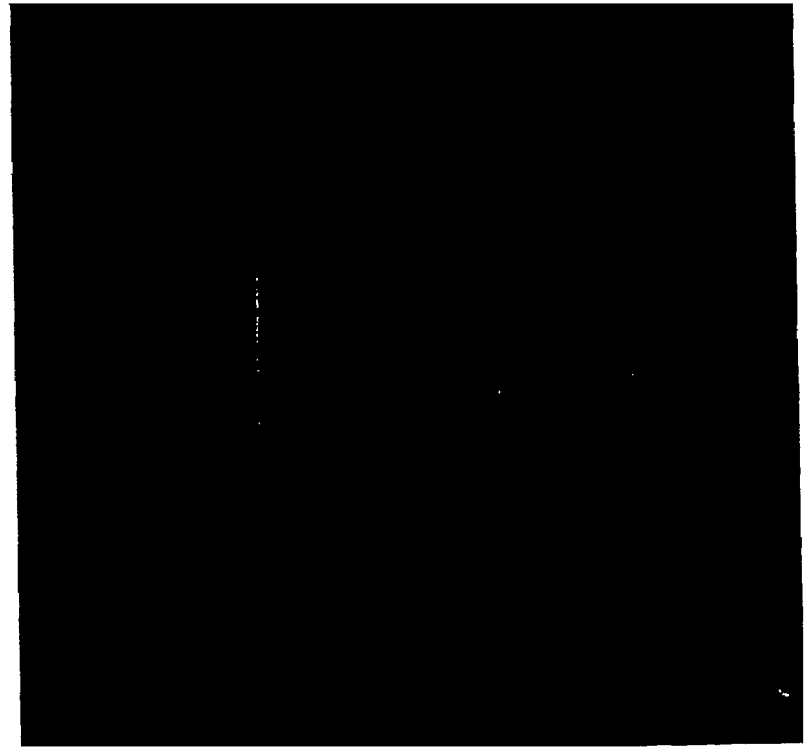
FIG. 25

MODIFIED BOTULINUM NEUROTOXINS

CROSS REFERENCE

This application is a continuation-in-part of application Ser. No. 10/163,106, filed Jun. 4, 2002, which is a continuation-in-part of application Ser. No. 09/910,346, filed Jul. 20, 2001 now abandoned, which is a continuation-in-part of application Ser. No. 09/620,840, filed Jul. 21, 2000 now U.S. Pat. No. 6,903,187. All prior applications are incorporated herein by reference in their entireties.

BACKGROUND

The present invention relates to modified neurotoxins, particularly modified Clostridial neurotoxins, and use thereof to treat various conditions including conditions that have been treated using naturally occurring *botulinum* toxins.

The present invention also relates to a composition comprising an isolated or purified *botulinum* toxin light chain (or a part thereof) and an intracellular structure, such as a component of a mammalian plasma membrane.

*botulinum* toxin, for example, *botulinum* toxin type A, has been used in the treatment of numerous conditions including pain, skeletal muscle conditions, smooth muscle conditions and glandular conditions. *botulinum* toxins are also used for cosmetic purposes.

Numerous examples exist for treatment using *botulinum* toxin. For examples of treating pain see Aoki, et al., U.S. Pat. No. 6,113,915 and Aoki, et al., U.S. Pat. No. 5,721,215. For an example of treating a neuromuscular disorder, see U.S. Pat. No. 5,053,005, which suggests treating curvature of the juvenile spine, i.e., scoliosis, with an acetylcholine release inhibitor, preferably *botulinum* toxin A. For the treatment of strabismus with *botulinum* toxin type A, see Elston, J. S., et al., British Journal of Ophthalmology, 1985, 69, 718-724 and 891-896. For the treatment of blepharospasm with *botulinum* toxin type A, see Adenis, J. P., et al., J. Fr. Ophthalmol., 1990, 13 (5) at pages 259-264. For treating spasmodic and oromandibular dystonia torticollis, see Jankovic et al., Neurology, 1987, 37, 616-623. Spasmodic dysphonia has also been treated with *botulinum* toxin type A. See Blitzer et al., Ann. Otol. Rhino. Laryngol, 1985, 94, 591-594. Lingual dystonia was treated with *botulinum* toxin type A according to Brin et al., Adv. Neurol. (1987) 50, 599-608. Cohen et al., Neurology (1987) 37 (Suppl. 1), 123-4, discloses the treatment of writer's cramp with *botulinum* toxin type A.

It would be beneficial to have *botulinum* toxins with altered biological persistence and/or altered biological activity. For example, a *botulinum* toxin can be used to immobilize muscles and prevent limb movements after tendon surgery to facilitate recovery. It would be beneficial to have a *botulinum* toxin (such as a *botulinum* toxin type A) which exhibits a reduced period of biological persistence so that a patient can regain muscle use and mobility at about the time they recover from surgery. Furthermore, a *botulinum* toxin with an altered biological activity, such as an enhanced biological activity can have utility as a more efficient toxin (i.e. more potent per unit amount of toxin), so that less toxin can be used.

Additionally, there is a need for modified neurotoxins (such as modified Clostridial toxins) which can exhibit an enhanced period of biological persistence and modified neurotoxins (such as modified Clostridial toxins) with reduced biological persistence and/or biological activity and methods for preparing such toxins.

Furthermore, there is a need for an isolated composition comprising a *botulinum* toxin light chain component and an intracellular structure component wherein the structure component interacts with the light chain component in a manner effective to facilitate substrate proteolysis within a cell, since such a composition can have utility for research, diagnostic and therapeutic purposes.

DEFINITIONS

Before proceeding to describe the present invention, the following definitions are provided and apply herein.

"Heavy chain" means the heavy chain of a Clostridial neurotoxin. It has a molecular weight of about 100 kDa and can be referred to herein as Heavy chain or as H.

"$H_N$" means a fragment (having a molecular weight of about 50 kDa) derived from the Heavy chain of a Clostridial neurotoxin which is approximately equivalent to the amino terminal segment of the Heavy chain, or the portion corresponding to that fragment in the intact Heavy chain. It is believed to contain the portion of the natural or wild-type Clostridial neurotoxin involved in the translocation of the light chain across an intracellular endosomal membrane.

"$H_C$" means a fragment (about 50 kDa) derived from the Heavy chain of a Clostridial neurotoxin which is approximately equivalent to the carboxyl terminal segment of the Heavy chain, or the portion corresponding to that fragment in the intact Heavy chain. It is believed to be immunogenic and to contain the portion of the natural or wild-type Clostridial neurotoxin involved in high affinity binding to various neurons (including motor neurons), and other types of target cells.

"Light chain" means the light chain of a Clostridial neurotoxin. It has a molecular weight of about 50 kDa, and can be referred to as light chain, L or as the proteolytic domain (amino acid sequence) of a Clostridial neurotoxin. The light chain is believed to be effective as an inhibitor of exocytosis, including as an inhibitor of neurotransmitter (i.e. acetylcholine) release when the light chain is present in the cytoplasm of a target cell.

"Neurotoxin" means a molecule that is capable of interfering with the functions of a cell, including a neuron. The "neurotoxin" can be naturally occurring or man-made. The interfered with function can be exocytosis.

"Modified neurotoxin" means a neurotoxin which includes a structural modification. In other words, a "modified neurotoxin" is a neurotoxin which has been modified by a structural modification. The structural modification changes the biological persistence, such as the biological half-life (i.e. the duration of action of the neurotoxin) and/or the biological activity of the modified neurotoxin relative to the neurotoxin from which the modified neurotoxin is made or derived. The modified neurotoxin is structurally different from a naturally existing neurotoxin.

"Mutation" means a structural modification of a naturally occurring protein or nucleic acid sequence. For example, in the case of nucleic acid mutations, a mutation can be a deletion, addition or substitution of one or more nucleotides in the DNA sequence. In the case of a protein sequence mutation, the mutation can be a deletion, addition or substitution of one or more amino acids in a protein sequence. For example, a specific amino acid comprising a protein sequence can be substituted for another amino acid, for example, an amino acid selected from a group which includes the amino acids alanine, aspargine, cysteine, aspartic acid, glutamic acid, phenylalanine, glycine, histidine, isoleucine, lysine, leucine, methionine, proline, glutamine, arginine, serine, threonine, valine, tryptophan, tyrosine or any other natural or non-naturally occurring amino acid or chemically modified amino acids. Mutations to a protein sequence can be the result of mutations to DNA sequences that when transcribed, and the resulting mRNA translated, produce the mutated protein sequence. Mutations to a protein sequence can also be created by fusing a peptide sequence containing the desired mutation to a desired protein sequence.

"Structural modification" means any change to a neurotoxin that makes it physically or chemically different from an identical neurotoxin without the structural modification.

"Biological persistence" or "persistence" means the time duration of interference or influence caused by a neurotoxin or a modified neurotoxin with a cellular (such as a neuronal) function, including the temporal duration of an inhibition of exocytosis (such as exocytosis of neurotransmitter, for example, acetylcholine) from a cell, such as a neuron.

"Biological half-life" or "half-life" means the time that the concentration of a neurotoxin or a modified neurotoxin, preferably the active portion of the neurotoxin or modified neurotoxin, for example, the light chain of Clostridial toxins, is reduced to half of the original concentration in a mammalian cell, such as in a mammalian neuron.

"Biological activity" or "activity" means the amount of cellular exocytosis inhibited from a cell per unit of time, such as exocytosis of a neurotransmitter from a neuron.

"Target cell" means a cell (including a neuron) with a binding affinity for a neurotoxin or for a modified neurotoxin.

"PURE A" means a purified *botulinum* toxin type A, that is the 150 kDa toxin molecule.

SUMMARY

New structurally modified neurotoxins have been discovered. The present structurally modified neurotoxins can provide substantial benefits, for example, enhanced or decreased biological persistence and/or biological half-life and/or enhanced or decreased biological activity as compared to the unmodified neurotoxin.

In accordance with the present invention, there are provided structurally modified neurotoxins, which include a neurotoxin and a structural modification. The structural modification is effective to alter a biological persistence of the structurally modified neurotoxin relative to an identical neurotoxin without the structural modification. Also, the structurally modified neurotoxin is structurally different from a naturally existing neurotoxin.

The present invention also encompasses a modified neurotoxin comprising a neurotoxin with a structural modification, wherein said structural modification is effective to alter a biological activity of said modified neurotoxin relative to an identical neurotoxin without said structural modification, and wherein said modified neurotoxin is structurally different from a naturally existing neurotoxin. This structural modification can be effective to reduce exocytosis from a target cell by more than the amount of the exocytosis reduced from the target cell by an identical neurotoxin without said structural modification. Alternately, the structural modification can be effective to reduce an exocytosis from a target cell by less than the amount of the exocytosis reduced from the cell by an identical neurotoxin without said structural modification. Significantly, the exocytosis can be exocytosis of a neurotransmitter and the modified neurotoxin can exhibit an altered biological activity without exhibiting an altered biological persistence. The structural modification can comprise a leucine-based motif. Additionally, the modified neurotoxin can exhibits an altered biological activity as well as an altered biological persistence. The present invention also includes the circumstances where: (a) the modified neurotoxin exhibits an increased biological activity as well as an increased biological persistence; (b) the modified neurotoxin exhibits an increased biological activity and a reduced biological persistence; (c) the modified neurotoxin exhibits a decreased biological activity and a decreased biological persistence, and; (d) the modified neurotoxin exhibits an decreased biological activity and an increased biological persistence.

Importantly, a unit amount (i.e. on a molar basis) of the modified neurotoxin can be more efficient to reduce an exocytosis from a cell than is a unit amount of the naturally existing neurotoxin. In other words, a unit amount of a modified neurotoxin, such as a modified *botulinum* toxin type A, can cleave its' intracellular substrate (SNAP) in a manner such that a greater inhibition of neurotransmitter exocytosis results (i.e. less neurotransmitter is released from the cell), as compared to the inhibition of neurotransmitter exocytosis exhibited by the naturally occurring neurotoxin.

Further in accordance with the present invention, are structurally modified neurotoxins, wherein a structural modification is effective to enhance a biological persistence of the modified neurotoxin. The enhanced biological persistence of the structurally modified neurotoxin can be due, at least in part, to an increased half-life and/or biological activity of the structurally modified neurotoxin.

Still further in accordance with the present invention, there are provided structurally modified neurotoxins wherein a biological persistence of the structurally modified neurotoxin is reduced relative to that of an identical neurotoxin without the structural modification. This reduction in biological persistence can be due, at least in part, to a decreased biological half-life and/or activity of the structurally modified neurotoxins.

Still further in accordance with the present invention, there are provided structurally modified neurotoxins wherein the structural modification comprises a number of amino acids. For example, the number of amino acids comprising the structural modification can be 1 or more amino acids, from 1 to about 22 amino acids, from 2 to about 10 amino acids, and from about 4 to about 7 amino acids.

In one embodiment, the structural modifications of the structurally modified neurotoxins can comprise an amino acid. The amino acid can comprise an R group containing a number of carbons. For example, the number of carbon atoms in the amino acid can be 1 or more, from 1 to about 20 carbons, from 1 to about 12 carbons, from 1 to about 9 carbons, from 2 to about 6 carbons, and about 4 carbons. R group as used in this application refers to amino acid side chains. For example, the R group for alanine is $CH_3$, and, for example, the R group for serine is $CH_2OH$.

In some embodiments, there are provided structurally modified neurotoxins wherein the modification comprises an amino acid. The amino acid can comprise an R group which is substantially hydrocarbyl.

In still another embodiment, there are provided structurally modified neurotoxins wherein the structural modification comprises an amino acid. The amino acid further can comprise an R group that includes at least one heteroatom.

Further in accordance with the present invention, there are provided structurally modified neurotoxins wherein the structural modification comprises, for example, a leucine-based motif, a tyrosine-based motif, and/or an amino acid derivative. Examples of an amino acid derivative that can comprise a structurally modified neurotoxin are a myristylated amino acid, an N-glycosylated amino acid, and a phosphorylated amino acid. The phosphorylated amino acids can be phosphorylated by, for example, casein kinase II, protein kinase C, and tyrosine kinase.

Still further in accordance with the present invention, there are provided structurally modified neurotoxins which can include a structural modification. The neurotoxin can comprise three amino acid sequence regions. The first region can be effective as a cellular binding moiety. This binding moiety can be a binding moiety for a target cell, such as a neuron. The binding moiety can be the carboxyl terminus of a *botulinum* toxin heavy chain. It is well known that the carboxyl terminus of a *botulinum* toxin heavy chain can be effective to bind, for example, receptors found on certain cells, including certain nerve cells. In one embodiment, the carboxyl terminus binds to receptors found on a presynaptic membrane of a nerve cell. The second region can be effective to translocate a structurally modified neurotoxin, or a part of a structurally modified neurotoxin across an endosome membrane. The third region can be effective to inhibit exocytosis from a target cell. The inhibition of exocytosis can be inhibition of neurotransmitter release, such as acetylcholine from a presynaptic membrane. For example, it is well known that the *botulinum* toxin light chain is effective to inhibit, for example, acetylcholine (as well as other neurotransmitters) release from various neuronal and non-neuronal cells.

At least one of the first, second or third regions can be substantially derived from a Clostridial neurotoxin. The third region can include the structural modification. In addition, the modified neurotoxin can be structurally different from a naturally existing neurotoxin. Also, the structural modification can be effective to alter a biological persistence of the modified neurotoxin relative to an identical neurotoxin without the structural modification.

In one embodiment, there are provided structurally modified neurotoxins, wherein the neurotoxin can be *botulinum* serotype A, B, $C_1$, $C_2$, D, E, F, G, tetanus toxin and/or mixtures thereof.

In some embodiments, there are provided structurally modified neurotoxins where the third region can be derived from *botulinum* toxin serotype A. In addition, there are provided structurally modified neurotoxins wherein the third region cannot be derived from *botulinum* serotype A.

In still another embodiment, there are provided structurally modified neurotoxins wherein the structural modification includes a biological persistence enhancing component effective to enhance the biological persistence of the structurally modified neurotoxin. The enhancing of the biological persistence can be at least in part due to an increase in biological half-life and/or activity of the structurally modified neurotoxin.

Further in accordance with the present invention, there are provided structurally modified neurotoxins comprising a biological persistence enhancing component, wherein the biological persistence enhancing component can comprise a leucine-based motif. The leucine-based motif can comprise a run of 7 amino acids, where a quintet of amino acids and a duplet of amino acids can comprise the leucine-based motif. The quintet of amino acids can define the amino terminal end of the leucine-based motif. The duplet of amino acids can define the carboxyl end of the leucine-based motif. There are provided structurally modified neurotoxins wherein the quintet of amino acids can comprise one or more acidic amino acids. For example, the acidic amino acid can be glutamate or aspartate. The quintet of amino acids can comprise a hydroxyl containing amino acid. The hydroxyl containing amino acid can be, for example, a serine, a threonine or a tyrosine. This hydroxyl containing amino acid can be phosphorylated. At least one amino acid comprising the duplet of amino acids can be a leucine, isoleucine, methionine, alanine, phenylalanine, tryptophan, valine or tyrosine. In addition, the duplet of amino acids in the leucine-based motif can be leucine-leucine, leucine-isoleucine, isoleucine-leucine or isoleucine-isoleucine, leucine-methionine. The leucine-based motif can be an amino acid sequence of phenylalanine-glutamate-phenylalanine-tyrosine-lysine-leucine-leucine.

In one embodiment, there are provided structurally modified neurotoxins wherein the modification can be a tyrosine-based motif. The tyrosine-based motif can comprise four amino acids. The amino acid at the N-terminal end of the tyrosine-based motif can be a tyrosine. The amino acid at the C-terminal end of the tyrosine-based motif can be a hydrophobic amino acid.

Further in accordance with the present invention, the third region can be derived from *botulinum* toxin serotype A or form one of the other *botulinum* toxin serotypes.

Still further in accordance with the present invention, there are provided structurally modified neurotoxins where the biological persistence of the structurally modified neurotoxin can be reduced relative to an identical neurotoxin without the structural modification. The reduced biological persistence can be in part due a decreased biological half-life and/or to a decrease biological activity of the neurotoxin.

In one embodiment, there are provided structurally modified neurotoxins, where the structural modification can include a leucine-based motif with a mutation of one or more amino acids comprising the leucine-based motif. The mutation can be a deletion or substitution of one or more amino acids of the leucine-based motif.

In some embodiments, there are provided structurally modified neurotoxins, where the structural modification includes a tyrosine-based motif with a mutation of one or more amino acids comprising the tyrosine-based motif. For example, the mutation can be a deletion or substitution of one or more amino acids of the tyrosine-based motif.

In still another embodiment, there are provided structurally modified neurotoxins, wherein the structural modification comprises an amino acid derivative with a mutation of the amino acid derivative or a mutation to a nucleotide or amino acid sequence which codes for the derivativization of the amino acid. For example, a deletion or substitution of the derivatized amino acid or a nucleotide or amino acid sequence responsible for a derivatization of the derivatized amino acid. The amino acid derivative can be, for example, a myristylated amino acid, an N-glycosylated amino acid, or a phosphorylated amino acid. The phosphorylated amino acid can be produced by, for example, casein kinase II, protein kinase C or tyrosine kinase.

In one embodiment of the present invention, there are provided structurally modified neurotoxins, wherein the first, second and/or third regions of the structurally modified neurotoxins can be produced by recombinant DNA methodologies, i.e. produced recombinantly.

In some embodiments of the present invention, there are provided structurally modified neurotoxins, wherein the first, second and/or third region of the neurotoxin is isolated from a naturally existing Clostridial neurotoxin.

Another embodiment of the present invention provides a modified neurotoxin comprising a *botulinum* toxin (such as a *botulinum* toxin type A) which includes a structural modification which is effective to alter a biological persistence of the modified neurotoxin relative to an identical neurotoxin without the structural modification. The structural modification can comprise a deletion of amino acids 416 to 437 from a light chain of the neurotoxin of SEQ ID NO: 29.

In still another embodiment of the present invention there is provided a modified neurotoxin (such as a *botulinum* toxin type A) which includes a structural modification which is effective to alter a biological persistence of the modified neurotoxin relative to an identical neurotoxin without the structural modification. The structural modification can comprise a deletion of amino acids 1 to 8 from a light chain of the neurotoxin of SEQ ID NO. 29.

Still further in accordance with the present invention there is provided a modified neurotoxin, such as a *botulinum* toxin type A, which includes a structural modification which is effective to alter a biological persistence of the modified neurotoxin relative to an identical neurotoxin without the structural modification. The structural modification may comprise, for example, a deletion of 2 or more amino acids from 1 to 20 and a deletion of 2 or more amino acids from 398 to 437 from a light chain of the neurotoxin of SEQ ID NO: 29. In one embodiment, the structural modification comprises a deletion of amino acids 1 to 8 and 416 to 437 from a light chain of the neurotoxin of SEQ ID NO: 29. In some embodiments, the structural modification comprises a deletion of amino acids 1 to 9 and 416 to 437 from a light chain of the neurotoxin of SEQ ID NO: 29. With regard to deletion on either the 1-8 or 1-9 amino acids; after synthesis the initial Methionine (M) of, for example, BoNT/A is apparently post-translationally removed within Clostridia. Amino acids 1-8 do not include the initial Met residue. If one includes the initial Met residue, then amino acids 1-9 are removed. Of course a recombinant toxin would need a Met residue incorporated to start protein synthesis. It may or may not be removed following synthesis.

For example, a native synthesized BoNT/A can comprise: MPFVNKQFNYKD (SEQ ID NO: 14), whereas a native processed BoNT/A can comprise PFVNKQFNYKD (SEQ ID NO: 15). Thus a proposed 8 amino acid deletion of SEQ ID NO: 27 would retain the YKD amino acid residues, while a recombinantly produced deletion would retain the amino acid residues NYKD at position numbers 9-12 of SEQ ID NO: 14.

Still further in accordance with the present invention, there is provided a modified *botulinum* toxin, such as a modified *botulinum* toxin type A, which includes a structural modification effective to alter a biological persistence of the modified neurotoxin relative to an identical neurotoxin without said structural modification. The structural modification can comprise a substitution of leucine at position 427 for an alanine and a substitution of leucine at position 428 for an alanine in a light chain of said neurotoxin of SEQ ID NO: 29.

Additionally, the scope of the present invention also includes methods for enhancing the biological persistence and/or or for enhancing the biological activity of a neurotoxin. In these methods, a structural modification can be fused or added to the neurotoxin, for example, the structural modification can be a biological persistence enhancing component and/or a biological activity enhancing component. Examples of structural modifications that can be fused or added to the neurotoxin are a leucine-based motif, a tyrosine-based motif and an amino acid derivative. Examples of amino acid derivatives are a myristylated amino acid, an N-glycosylated amino acid, and a phosphorylated amino acid. An amino acid can be phosphorylated by, for example, protein kinase C, caseine kinase II or tyrosine kinase.

Also in accordance with the present invention, there are provided methods for reducing the biological persistence and/or for reducing the biological activity of a neurotoxin. These methods can comprise a step of mutating an amino acid of the neurotoxin. For example, an amino acid of a leucine-based motif within the neurotoxin can be mutated. Also, for example, one or more amino acids within a tyrosine-based motif of the neurotoxin can be mutated. Also, for example, an amino acid derivative for DNA or amino acid sequence responsible for the derivatization of the amino acid can be mutated. The derivatized amino acid can be a myristylated amino acid, a N-glycosylated amino acid, or a phosphorylated amino acid. The phosphorylated amino acid can be produced by, for example, protein kinase C, caseine kinase II and tyrosine kinase. These mutations can be, for example, amino acid deletions or amino acids substitutions.

The present invention also includes methods for treating a condition. The methods can comprise a step of administering an effective dose of a structurally modified neurotoxin to a mammal to treat a condition. The structurally modified neurotoxin can include a structural modification. The structural modification is effective to alter the biological persistence and/or the biological activity of the neurotoxin. These methods for treating a condition can utilize a neurotoxin that does not comprise a leucine-based motif. Also, these methods for treating a condition can utilize a neurotoxin, which includes a biological persistence enhancing component and/or a biological activity enhancing component. The biological persistence or activity enhancing component can comprise, for example, a tyrosine-based motif, a leucine-based motif or an amino acid derivative. The amino acid derivative can be, for example, a myristylated amino acid, an N-glycosylated amino acid or a phosphorylated amino acid. The phosphorylated amino acid can be produced by, for example, protein kinase C, caseine kinase II or tyrosine kinase. The condition treated can be a neuromuscular disorder, an autonomic disorder or pain. The treatment of a neuromuscular disorder can comprise a step of locally administering an effective amount of a modified neurotoxin to a muscle or a group of muscles. A method for treating an autonomic disorder can comprise a step of locally administering an effective amount of a modified neurotoxin to a gland or glands. A method for treating pain can comprise a step of administering an effective amount of a modified neurotoxin to the site of the pain. In addition, the treatment of pain can comprise a step of administering an effective amount of a modified neurotoxin to the spinal cord.

Still further in accordance with the present invention, there are provided compositions and methods for treating with modified neurotoxins conditions including spasmodic dysphonia, laryngeal dystonia, oromandibular dysphonia, lingual dystonia, cervical dystonia, focal hand dystonia, blepharospasm, strabismus, hemifacial spasm, eyelid disorder, cerebral palsy, focal spasticity, spasmodic colitis, neurogenic bladder, anismus, limb spasticity, tics, tremors, bruxism, anal fissure, achalasia, dysphagia, lacrimation, hyperhydrosis, excessive salivation, excessive gastrointestinal secretions, pain from muscle spasms, headache pain, brow furrows and skin wrinkles.

The present invention also provides for isolated compositions which include a *botulinum* toxin light chain component and an intracellular structure component. The structure component interacts with the light chain component in a manner effective to facilitate or alter substrate proteolysis within a cell. Such a composition can have utility for research, diagnostic and therapeutic purposes. It is believed that toxin light chain localization is important for maintenance of the intracellular activity of, at least, the LC of BoNT. Thus, it is believed that an intracellular localization is an important factor in the long biological half life of LC/A. For example, our invention indicates that LC/A may be localized to the intracellular plasma membrane. Our experiments indicate that the LC/A may not be actually inserted into the plasma membrane, but may be instead directly associated with proteins that reside at or near the plasma membrane.

Also provided are methods of producing an isolated composition comprising a *botulinum* toxin light chain component and an intracellular structure component wherein the structure component interacts with the light chain component in a manner effective to facilitate substrate proteolysis within a cell. The methods may include the steps of: 1) interacting a *botulinum* toxin light chain component with an intracellular structure component at conditions effective to facilitate proteolysis of a substrate within a cell; and 2) isolating the composition. Compositions which include a modified *botulinum* toxin light chain and a structure component may be isolated by these methods as well.

In one embodiment, the light chain component is a type A toxin light chain component and the intracellular structure component is a plasma membrane, for example a plasma membrane of a mammalian cell.

In some embodiments, the light chain component is a type B toxin light chain component and the intracellular structure includes a cytoplasm component. The cytoplasm component may include mitochondria, nucleus, endoplasmic reticulum, golgi apparatus, lysosomes or secretory vesicles or combination thereof. The cytoplasm component may include any portion of an organelle, for example, the membrane of an organelle. Further, the cytoplasm component may also include any substance which is included inside a cell. In one embodiment, the cytoplasm component is from a mammalian cell.

The structure component of the present invention may include a cell membrane. The cell membrane may be a plasma membrane, for example, a plasma membrane of a mammalian cell.

The structure component may include a protein complex. In one embodiment, the protein complex includes a light chain component. A protein complex may also include a substrate of the light chain. In one embodiment, the substrate is an intracellular component involved in exocytosis. For example, the substrate may be SNAP-25. A protein complex may be between about 100 kDa and about 1000 kDa or more. In one embodiment, the protein complex is between about 100 kDa and about 400 kDa. For example, the protein complex may be about 110 kDa, about 140 kDa or about 170 kDa.

Our invention also includes an isolated composition comprising a *botulinum* toxin light chain component and an intracellular structure component wherein the structure component interacts with the light chain component in a manner effective to facilitate substrate proteolysis within a cell, where the light chain component comprises a C-terminal portion of a *botulinum* toxin light chain. Thus, our invention encompasses what can be referred to as a "swapping of tails". For example our invention encompasses a chimeric toxin protein where the C-terminal tail of LC/A and LC/E are swapped or changed. Also included within the scope of our invention is a modified or chimeric toxin molecule wherein the N-terminus of the LC of one *botulinum* toxin serotype are swapped or exchanged for the N-terminus of the LC of another *botulinum* toxin serotype.

Without wishing to be bound by theory, it can be hypothesized that toxin LC localization can provide a protective role (i.e. protective from cellular proteases) and thereby provide the LC of, for example, BoNT/A with it's extended duration of action.

It is conceivable that a modified toxin could be cytosolic with full enzymatic activity, and only the duration of action is modified. Our invention encompasses a cytoplasmic *botulinum* toxin light chain that does not interact with a intracellular structure component. For example, upon removal of the targeting sequence of BoNT/A it can accumulate in the cytosol and exhibit a shorter duration of action, and not interact with an intracellular structure component in a specific manner.

Thus, the presence of localizing signals and interaction with cellular partners can be important for sequestration of LC/A from cellular proteases. In this manner, sequestration or protection of the LC may be responsible for the long duration of action of BoNT/A by protection of the LC potentially extending the enzymatic activity beyond that of a LC lacking any localization or interacting signals.

In the present compositions, the light chain component may include the light chain of *botulinum* toxin type A, B, C, D, E, F or G or a portion thereof or a modified light chain thereof. In one embodiment, the light chain component comprises a C-terminal portion of a *botulinum* toxin light chain.

In one embodiment, a modified light chain is a light chain with an added biological activity- or biological persistence-enhancing component effective to enhance the proteolytic activity of the light chain. For example, the enhancing component may include a leucine based motif of SEQ ID No: 1.

In some embodiments, a modified light chain component is a light chain with a mutation to one or more amino acids included in the light chain to reduce the proteolytic activity of the light chain. For example, the mutation may be in a biological activity/persistence enhancing component of the light chain, for example, in a leucine based motif of SEQ ID No: 1.

Any combination of features described herein are included within the scope of the present invention provided that the features included in any such combination are not mutually inconsistent as will be apparent from the context, this specification, and the knowledge of one of ordinary skill in the art.

Additional advantages and aspects of the present invention are apparent in the following detailed description and claims.

BRIEF DESCRIPTION OF THE DRAWINGS

FIG. 3 shows the amino acid sequence for *botulinum* type A light chain. The amino acid sequence of SEQ ID NO: 29 shown, minus the underlined amino acids represents *botulinum* type A truncated light chain. The overline labeled ΔN8 indicates the eight amino acids deleted from the amino terminus of the light chain, the overline labeled ΔC22 indicates the 22 amino acids deleted from the carboxy terminus of the light chain. The double underline indicates the leucine-based motif and the dotted lines indicate tyrosine-based motifs.

FIG. 8 shows sequence alignment and consensus sequence for *botulinum* toxin type A Hall A light chain of SEQ ID NO: 29 and *botulinum* toxin type B Danish I light chain of SEQ ID NO: 30.

Figure 9:
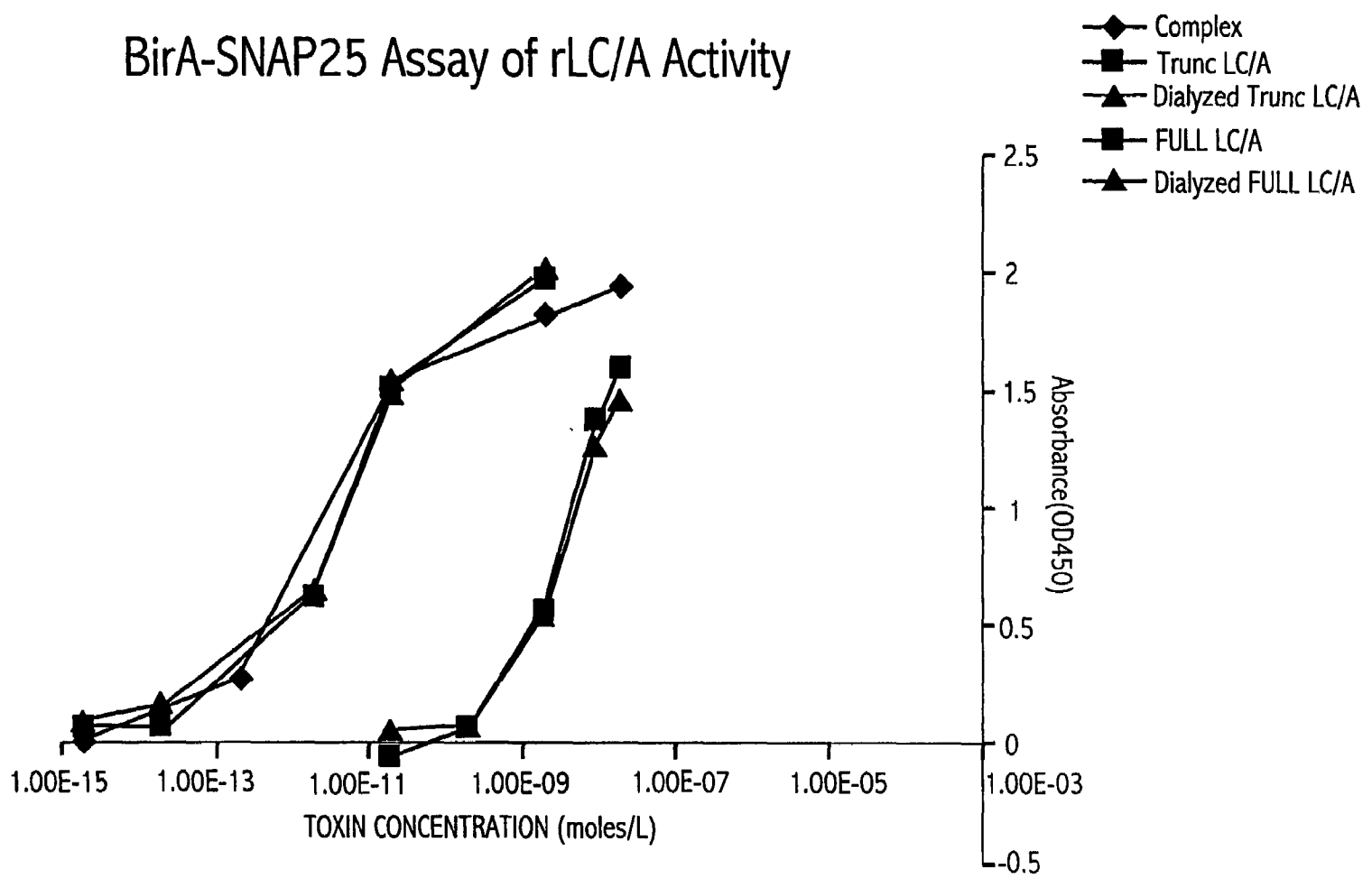

FIG. 9 is a graph which illustrates the results of an in vitro ELISA assay carried out by the inventors demonstrating that a truncated LC/A in vitro cleaves substrate at a slower rate or less efficiently than does non-truncated LC/A.

FIG. 17 shows PC12 cells transfected with plasmids encoding GFP-LCA(ΔN/ΔC) and LCA(ΔN/ΔC)-GFP. The N- and C-terminal truncated form of LC/A may be localized to an internal structure or accumulated within the cell rather than at the plasma membrane. Confocal microscope images are taken from slices at approximately the middle of the cell.

FIG. 18. shows confocal images of GFP-LCA(LL-->AA) expressed in PC12 cells. This construct shows a mixed pattern of localization. Some cells seem to have protein localized to the plasma membrane as well as the cytosol, other cells have primarily cytosolic protein, while others are localized to near the plasma membrane, but in a much more diffuse manner than GFP-LC/A (similar to other reported dileucine mutants).

FIG. 20A shows the presence of the SNAP-25$_{197}$ BoNT/A cleavage product in lysates containing GFP-LCA and GFP +LCA, but not GFP alone. FIG. 20B shows the presence of the SNAP-25$_{180}$ BoNT/E cleavage product in lysates containing GFP-LCE, but not GFP alone.

FIG. 21 shows that light chain A localizes to the plasma membrane. The top panel shows that GFP alone exhibits a diffuse cytoplasmic localization. However, the bottom panel shows that GFP-*botulinum* toxin A light chain localizes to the plasma membrane.

FIG. 22 shows that light chain B localizes in the cytoplasm. The top panel shows that GFP-*botulinum* toxin B light chain exhibits a diffuse cytoplasmic localization. The bottom panel shows that *botulinum* toxin B light chain-GFP localizes to punctate bodies inside the cytoplasm.

FIG. 23 shows that Light Chain E also localizes primarily in the cytoplasm. The top panel shows that GFP-*botulinum* toxin E light chain exhibits a semi-diffuse cytoplasmic localization. The bottom panel shows that *botulinum* toxin B light chain-GFP exhibits a diffuse cytoplasmic localization.

FIG. 25 shows localization of GFP in HeLa and HEK293T cells.

FIG. 30B shows the western blot of immunoprecipitated samples separated under non-reducing conditions leaving the cross linking agent uncleaved. Three different sized protein complexes containing GFP-LCA were detected. The 120 kDa protein is not completely defined. The 80 kDa protein is GFP-LCA.

FIG. 31A shows the western blot of the samples separated under reduced conditions. A 25 kDa protein is detected in the GFP-LCA sample corresponding to SNAP-25. FIG. 31B shows the western blot of samples separated under non-reducing conditions. The three protein bands detected with the antibody for SNAP-25 were detected with the antibody for LCA. These data indicate LCA forms a complex with SNAP-25 when transfected into PC-12 cells.

DETAILED DESCRIPTION

Figure 1:
FIG. 1 shows localization of GFP-*botulinum* toxin A light chain in (nerve growth factor) NGF-differentiated live PC12 cells visualized on a fluorescence inverted microscope. The arrow indicates that GFP-*botulinum* toxin A light chain localizes to the plasma membrane.

The present invention is based upon the discovery that the biological persistence and/or the biological activity of a neurotoxin can be altered by structurally modifying the neurotoxin. In other words, a modified neurotoxin with an altered biological persistence and/or biological activity can be formed from a neurotoxin containing or including a structural modification. In one embodiment, the structural modification includes the fusing of a biological persistence enhancing component to the primary structure of a neurotoxin to enhance its biological persistence. In a suitable embodiment, the biological persistence enhancing component is a leucine-based motif. Even more preferably, the biological half-life and/or the biological activity of the modified neurotoxin is enhanced by about 100%. Generally speaking, the modified neurotoxin has a biological persistence of about 20% to 300% more than an identical neurotoxin without the structural modification. That is, for example, the modified neurotoxin including the biological persistence enhancing component is able to cause a substantial inhibition of neurotransmitter release for example, acetylcholine from a nerve terminal for about 20% to about 300% longer than a neurotoxin that is not modified.

The present invention also includes within its scope a modified neurotoxin with a biological activity altered as compared to the biological activity of the native or unmodified neurotoxin. For example, the modified neurotoxin can exhibit a reduced or an enhanced inhibition of exocytosis (such as exocytosis of a neurotransmitter) from a target cell with or without any alteration in the biological persistence of the modified neurotoxin.

In a broad embodiment of the present invention, a leucine-based motif is a run of seven amino acids. The run is organized into two groups. The first five amino acids starting from the amino terminal of the leucine-based motif form a "quintet of amino acids." The two amino acids immediately following the quintet of amino acids form a "duplet of amino acids." In a suitable embodiment, the duplet of amino acids is located at the carboxyl terminal region of the leucine-based motif. In a suitable embodiment, the quintet of amino acids includes at least one acidic amino acid selected from a group consisting of a glutamate and an aspartate.

The duplet of amino acid includes at least one hydrophobic amino acid, for example leucine, isoleucine, methionine, alanine, phenylalanine, tryptophan, valine or tyrosine. Preferably, the duplet of amino acid is a leucine-leucine, a leucine-isoleucine, an isoleucine-leucine or an isoleucine-isoleucine, leucine-methionine. Even more preferably, the duplet is a leucine-leucine.

In one embodiment, the leucine-based motif is xDxxxLL (SEQ ID NO: 17), wherein x can be any amino acids. In another embodiment, the leucine-based motif is xExxxLL (SEQ ID NO: 18) wherein E is glutamic acid. In another embodiment, the duplet of amino acids can include an isoleucine or a methionine, forming xDxxxLI (SEQ ID NO: 19) or xDxxxLM (SEQ ID NO: 20), respectively. Additionally, the aspartic acid, D, can be replaced by a glutamic acid, E, to form xExxxLI (SEQ ID NO: 21), xExxxIL (SEQ ID NO: 22) and xExxxLM (SEQ ID NO: 23). In a preferred embodiment, the leucine-based motif is phenylalanine-glutamate-phenylalanine-tyrosine-lysine-leucine-leucine, SEQ ID NO: 1.

In some embodiments, the quintet of amino acids comprises at least one hydroxyl containing amino acid, for example, a serine, a threonine or a tyrosine. Preferably, the hydroxyl containing amino acid can be phosphorylated. More preferably, the hydroxyl containing amino acid is a serine which can be phosphorylated to allow for the binding of adapter proteins.

Although non-modified amino acids are provided as examples, a modified amino acid is also contemplated to be within the scope of this invention. For example, leucine-based motif can include a halogenated, preferably, fluorinated leucine.

Various leucine-based motif are found in various species. A list of possible leucine-based motif derived from the various species that can be used in accordance with this invention is shown in Table 1. This list is not intended to be limiting.

TABLE 1

| Species | Sequence | SEQ ID # |
| --- | --- | --- |
| Botulinum type A | FEFYKLL | 1 |
| Rat VMAT 1 | EEKRAIL | 2 |
| Rat VMAT 2 | EEKMAIL | 3 |
| Rat VAChT | SERDVLL | 4 |
| Rat δ | VDTQVLL | 5 |
| Mouse δ | AEVQALL | 6 |
| Frog γ/δ | SDKQNLL | 7 |
| Chicken γ/δ | SDRQNLI | 8 |
| Sheep δ | ADTQVLM | 9 |
| Human CD3γ | SDKQTLL | 10 |
| Human CD4 | SQIKRLL | 11 |
| Human δ | ADTQALL | 12 |
| S. cerevisiae Vam3p | NEQSPLL | 13 |

VMAT is vesicular monoamine transporter; VACht is vesicular acetylcholine transporter and S. cerevisiae Vam3p is a yeast homologue of synaptobrevin. Italicized serine residues are potential sites of phosphorylation.

The modified neurotoxin can be formed from any neurotoxin. Also, the modified neurotoxin can be formed from a fragment of a neurotoxin, for example, a *botulinum* toxin with a portion of the light chain and/or heavy chain removed. Preferably, the neurotoxin used is a Clostridial neurotoxin. A Clostridial neurotoxin comprises a polypeptide having three amino acid sequence regions. The first amino acid sequence region can include a target cell (i.e. a neuron) binding moiety which is substantially completely derived from a neurotoxin selected from a group consisting of beratti toxin; butyricum toxin; tetanus toxin; *botulinum* type A, B, C₁, D, E, F, and G. Preferably, the first amino acid sequence region is derived from the carboxyl terminal region of a toxin heavy chain, H_C. Also, the first amino acid sequence region can comprise a targeting moiety which can comprise a molecule (such as an amino acid sequence) that can bind to a receptor, such as a cell surface protein or other biological component on a target cell.

The second amino acid sequence region is effective to translocate the polypeptide or a part thereof across an endosome membrane into the cytoplasm of a neuron. In one embodiment, the second amino acid sequence region of the polypeptide comprises an amine terminal of a heavy chain, H_N, derived from a neurotoxin selected from a group consisting of beratti toxin; butyricum toxin; tetanus toxin; *botulinum* type A, B, C₁, D, E, F, and G.

The third amino acid sequence region has therapeutic activity when it is released into the cytoplasm of a target cell, such as a neuron. In one embodiment, the third amino acid sequence region of the polypeptide comprises a toxin light chain, L, derived from a neurotoxin selected from a group consisting of beratti toxin; butyricum toxin; tetanus toxin; *botulinum* type A, B, C₁, D, E, F, and G.

The Clostridial neurotoxin can be a hybrid neurotoxin. For example, each of the neurotoxin's amino acid sequence regions can be derived from a different Clostridial neurotoxin serotype. For example, in one embodiment, the polypeptide comprises a first amino acid sequence region derived from the H_C of the tetanus toxin, a second amino acid sequence region derived from the H_N of *botulinum* type B. and a third amino acid sequence region derived from the light chain of *botulinum* serotype E. All other possible combinations are included within the scope of the present invention.

Alternatively, all three of the amino acid sequence regions of the Clostridial neurotoxin can be from the same species and same serotype. If all three amino acid sequence regions of the neurotoxin are from the same Clostridial neurotoxin species and serotype, the neurotoxin will be referred to by the species and serotype name. For example, a neurotoxin polypeptide can have its first, second and third amino acid sequence regions derived from *Botulinum* type E. In which case, the neurotoxin is referred as *Botulinum* type E.

Additionally, each of the three amino acid sequence regions can be modified from the naturally occurring sequence from which they are derived. For example, the amino acid sequence region can have at least one or more amino acids added or deleted as compared to the naturally occurring sequence.

A biological persistence enhancing component or a biological activity enhancing component, for example a leucine-based motif, can be fused with any of the above described neurotoxins to form a modified neurotoxin with an enhanced biological persistence and/or an enhanced biological activity. "Fusing" as used in the context of this invention includes covalently adding to or covalently inserting in between a primary structure of a neurotoxin. For example, a biological persistence enhancing component and/or a biological activity enhancing component can be added to a Clostridial neurotoxin which does not have a leucine-based motif in its primary structure. In one embodiment, a leucine-based motif is fused with a hybrid neurotoxin, wherein the third amino acid sequence is derived from *botulinum* serotype A, B, C₁, C₂, D, E, F, or G. In some embodiments, the leucine-based motif is fused with a *botulinum* type E.

In some embodiments, a biological persistence enhancing component and/or a biological activity enhancing component is added to a neurotoxin by altering a cloned DNA sequence encoding the neurotoxin. For example, a DNA sequence encoding a biological persistence enhancing component and/or a biological activity enhancing component is added to a cloned DNA sequence encoding the neurotoxin into which the biological persistence enhancing component and/or a biological activity enhancing component is to be added. This can be done in a number of ways which are familiar to a molecular biologist of ordinary skill. For example, site directed mutagenesis or PCR cloning can be used to produce the desired change to the neurotoxin encoding DNA sequence. The DNA sequence can then be reintroduced into a native host strain. In the case of *botulinum* toxins the native host strain would be a *Clostridium botulinum* strain. Preferably, this host strain will be lacking the native *botulinum* toxin gene. In an alternative method, the altered DNA can be introduced into a heterologous host system such as *E. coli* or other prokaryotes, yeast, insect cell lines or mammalian cell lines. Once the altered DNA has been introduced into its host, the recombinant toxin containing the added biological persistence enhancing component and/or a biological activity enhancing component can be produced by, for example, standard fermentation methodologies.

Similarly, a biological persistence enhancing component can be removed from a neurotoxin. For example, site directed mutagenesis can be used to eliminate biological persistence enhancing components, for example, a leucine-based motif.

Standard molecular biology techniques that can be used to accomplish these and other genetic manipulations are found in Sambrook et al. (1989) which is incorporated in its entirety herein by reference.

In one embodiment, the leucine-based motif is fused with, or added to, the third amino acid sequence region of the neurotoxin. In a suitable embodiment, the leucine-based motif is fused with, or added to, the region towards the carboxylic terminal of the third amino acid sequence region. More preferably, the leucine-based motif is fused with, or added to, the carboxylic terminal of the third region of a neurotoxin. Even more preferably, the leucine-based motif is fused with, or added to the carboxylic terminal of the third region of *botulinum* type E. The third amino acid sequence to which the leucine-based motif is fused or added can be a component of a hybrid or chimeric modified neurotoxin. For example, the leucine-based motif can be fused to or added to the third amino acid sequence region (or a part thereof) of one *botulinum* toxin type (i.e. a *botulinum* toxin type A), where the leucine-based motif-third amino acid sequence region has itself been fused to or conjugated to first and second amino acid sequence regions from another type (or types) of a *botulinum* toxin (such as *botulinum* toxin type B and/or E).

In some embodiments, a structural modification of a neurotoxin which has a pre-existing biological persistence enhancing component and/or a biological activity enhancing component, for example, a leucine-based motif includes deleting or substituting one or more amino acids of the leucine-based motif. In addition, a modified neurotoxin includes a structural modification which results in a neurotoxin with one or more amino acids deleted or substituted in the leucine-based motif. The removal or substitution of one or more amino acids from the preexisting leucine-based motif is effective to reduce the biological persistence and/or a biological activity of a modified neurotoxin. For example, the deletion or substitution of one or more amino acids of the leucine-based motif of *botulinum* type A reduces the biological half-life and/or the biological activity of the modified neurotoxin.

Amino acids that can be substituted for amino acids contained in a biological persistence enhancing component include alanine, aspargine, cysteine, aspartic acid, glutamic acid, phenylalanine, glycine, histidine, isoleucine, lysine, leucine, methionine, proline, glutamine, arginine, serine, threonine, valine, tryptophan, tyrosine and other naturally occurring amino acids as well as non-standard amino acids.

In the present invention the native *botulinum* type A light chain has been shown to localize to differentiated PC12 cell membranes in a characteristic pattern. Biological persistence enhancing components are shown to substantially contribute to this localization.

The data of the present invention demonstrates that when the *botulinum* toxin type A light chain is truncated or when the leucine-based motif is mutated, the light chain substantially loses its ability to localize to the membrane in its characteristic pattern. Localization to the cellular membrane is believed to be a key factor in determining the biological persistence and/or the biological activity of a *botulinum* toxin. This is because localization to a cell membrane can protect the localized protein from intracellular protein degradation.

Figure 2:
FIG. 2 shows the localization of GFP-truncated *botulinum* toxin A light chain in NGF-differentiated live PC12 cells visualized on a fluorescence inverted microscope. The arrow indicates that GFP-truncated *botulinum* toxin A light chain localizes to punctuate bodies inside the cytoplasm.

FIGS. 1 and 2 show that deletion of the leucine-based motif from the light chain of *botulinum* type A can change membrane localization of the type A light chain. FIG. 1 shows localization of GFP-light chain A fusion protein in differentiated PC12 cells. The GFP fusion proteins were produced and visualized in differentiated PC12 cells using methods well known to those skilled in the art, for example, as described in Galli et al (1998) Mol Biol Cell 9:1437-1448, incorporated in its entirety herein by reference; also, for example, as described in Martinez-Arca et al (2000) J Cell Biol 149:889-899, also incorporated in its entirety herein by reference. Localization of a GFP-truncated light chain A is shown in FIG. 2. Comparing FIGS. 1 and 2, it can be seen that the pattern of localization is completely altered by the deletion of the N-terminus and C-terminus comprising the leucine-based motif. FIG. 3 shows the amino acid sequence of the *botulinum* type A light chain. The underlined amino acid sequences indicate the amino acids that were deleted in the truncated mutant. The leucine-based motif is indicated by the asterisked bracket.

Figure 4:
FIG. 4 shows the localization of GFP-*botulinum* toxin A light chain with LL to AA mutation at position 427 and 428 in NGF-differentiated live PC12 cells visualized on a fluorescence inverted microscope. The arrow indicates that GFP-*botulinum* toxin A light chain with LL to AA mutation localizes to punctate bodies inside the cytoplasm.

Further studies have been done in the present invention to analyze the effect of specific amino acid substitutions within the leucine-based motif. For example, in one study both leucine residues contained in the leucine-based motif were substituted for alanine residues. FIG. 4 shows the fluorescent image of differentiated PC12 cells transfected with DNA encoding this di-leucine to di-alanine substituted GFP-*botulinum* A light chain. As can be seen, the substitution of alanine for leucine at positions 427 and 428 in the *botulinum* type A light chain substantially changes the localization characteristic of the light chain.

It is within the scope of this invention that a leucine-based motif, or any other persistence enhancing component and/or a biological activity enhancing component present on a light chain, can be used to protect the heavy chain as well. A random coil belt extends from the *botulinum* type A translocation domain and encircles the light chain. It is possible that this belt keeps the two subunits in proximity to each other inside the cell while the light chain is localized to the cell membrane. The structure of native *botulinum* toxin type A is shown in FIG. 6.

Figure 5:
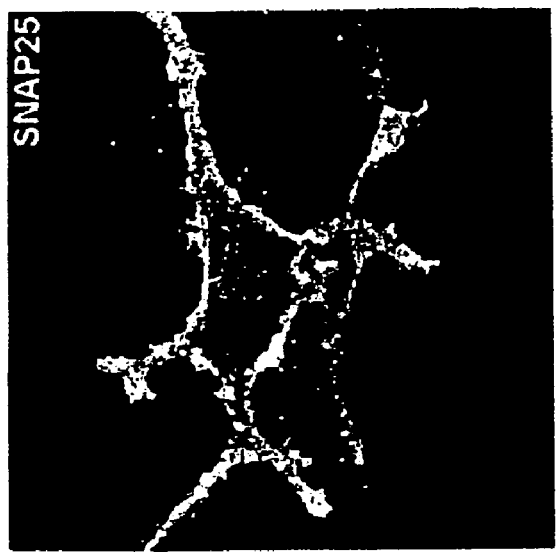
FIG. 5 shows localization of fluorescently labeled anti-SNAP-25 visualized in horizontal confocal sections of staurosporine-differentiated PC12 cells. The arrow indicates that SNAP-25 localizes to the plasma membrane.

In addition, the data of the present invention shows that the leucine-based motif can be valuable in localizing the *botulinum* A toxin in close proximity to the SNAP-25 substrate within the cell. This can mean that the leucine-based motif is important not only for determining the half-life of the toxin but for determining the activity of the toxin as well. That is, the toxin will have a greater activity if it is maintained in close proximity to the SNAP-25 substrate inside the cell. FIG. 5 shows the localization of SNAP-25 in horizontal confocal sections of differentiated PC12 cells (from Martinez-Arca et al (2000) J Cell Biol 149:889-899). Similarity in the pattern of localization can be seen when comparing localization of *botulinum* type A light chain as seen in FIG. 1 to localization of SNAP-25 seen in FIG. 5.

The data of the present invention clearly shows that truncation of the light chain, thereby deleting the leucine-based motif, or amino acid substitution within the leucine-based motif substantially changes membrane localization of the *botulinum* type A light chain in nerve cells. In both truncation and substitution a percentage of the altered light chain can localize to the cell membrane in a pattern unlike that of the native type A light chain (see FIGS. 1, 2 and 4). This data supports the presence of biological persistence enhancing components other than a leucine-based motif such as tyrosine motifs and amino acid derivatives. Use of these other biological persistence enhancing components and/or a biological activity enhancing components in modified neurotoxins is also within the scope of the present invention.

Also within the scope of the present invention is more than one biological persistence enhancing component used in combination in a modified neurotoxin to alter biological persistence of the neurotoxin that is modified. The present invention also includes use of more than one biological activity enhancing or biological activity reducing components used in combination in a modified neurotoxin to alter the biological activity of the neurotoxin that is modified.

Tyrosine-based motifs are within the scope of the present invention as biological persistence and/or a biological activity altering components. Tyrosine-based motifs comprise the sequence Y-X-X-Hy (SEQ ID NO: 24), where Y is tyrosine, X is any amino acid and Hy is a hydrophobic amino acid. Tyrosine-based motifs can act in a manner that is similar to that of leucine-based motifs. In FIG. 3 some of tyrosine motifs found in the type A toxin light chain are bracketed (SEQ ID NO: 31, SEQ ID NO: 32, SEQ ID NO: 33, SEQ ID NO: 34, SEQ ID NO: 35, SEQ ID NO: 36, SEQ ID NO: 37, and SEQ ID NO: 38). In addition, a tyrosine-based motif is found within the leucine-based motif which is indicated by an asterisked bracket in FIG. 3.

Also within the scope of the present invention are modified neurotoxins which comprise one or more biological persistence altering components and/or a biological activity enhancing components which occur naturally in both *botulinum* toxin types A and B.

Figure 7:
FIG. 7 shows localization of GFP-*botulinum* type B neurotoxin light chain in NGF-differentiated live PC12 cells visualized on a fluorescence inverted microscope. The arrow indicates that GFP-*botulinum* toxin B light chain localizes to punctate bodies inside the cytoplasm.

FIG. 7 shows localization of GFP-*botulinum* type B neurotoxin light chain in live, differentiated PC12 cells. Localization of the type B light chain appears to be to an intracellular organelle. Similar localization pattern is seen for GFP-truncated *botulinum* type A shown in FIG. 2. Localization of a *botulinum* toxin, or *botulinum* toxin light chain, within the cell is believed to be a key factor in determining biological persistence and/or biological activity of the toxin. Therefore, these data appear to indicate that there are biological persistence altering component(s), and/or biological activity altering component(s), common to the type A and type B *botulinum* toxins. These, and other biological persistence altering components, and biological activity altering components, are contemplated for use in accordance with the present invention.

FIG. 8 shows a sequence alignment between type A and type B light chains isolated from strains type A HaIIA (SEQ ID NO: 29) and type B Danish I (SEQ ID NO: 30) respectively. Light chains or heavy chains isolated from other strains of *botulinum* toxin types A and B can also be used for sequence comparison. The shaded amino acids represent amino acid identities, or matches, between the chains. Each of the shaded amino acids between amino acid position 10 and amino acid position 425 of the FIG. 8 consensus sequence, alone or in combination with any other shaded amino acid or amino acids, represents a biological persistence altering component that is within the scope of the present invention. For example, amino acids KAFK at positions 19 to 22 of SEQ ID NO: 29, LNK at positions 304 to 306 of SEQ ID NO: 29, L at position 228 of SEQ ID NO: 29 in combination with KL at positions 95 and 96 of SEQ ID NO: 29, FDKLYK at positions 346 to 351 of SEQ ID NO: 29, YL-T at positions 78 to 81 of SEQ ID NO: 29, YYD at positions 73 to 75 of SEQ ID NO: 29 in combination with YL at positions 78 and 79 of SEQ ID NO: 29 in combination with T a position 81 of SEQ ID NO: 29, F at position 297 of SEQ ID NO: 29 in combination with I at position 300 of SEQ ID NO: 29 in combination with KL at positions 95 and 96 of SEQ ID NO: 29 can be biological persistence altering components for use within the scope of this invention. In addition, conserved regions of charge, hydrophobicity, hydro-philicity and/or conserved secondary, tertiary, or quaternary structures that may be independent of conserved sequence are within the scope of the present invention.

Amino acid derivatives are also within the scope of the present invention as biological persistence enhancing components and/or as biological activity enhancing components. Examples of amino acid derivatives that act to effect biological persistence and/or biological activity are phosphorylated amino acids. These amino acids include, for example, amino acids phosphorylated by tyrosine kinase, protein kinase C or casein kinase II. Other amino acid derivatives within the scope of the present invention as biological persistence enhancing components and/or as biological activity enhancing components are myristylated amino acids and N-glycosylated amino acids.

The present invention also contemplates compositions which include a *botulinum* light chain component interacting with a cellular structure component, for example, an intracellular structure component. The structure component may include lipid, carbohydrate, protein or nucleic acid or any combination thereof.

The structure component may include a cell membrane, for example, a plasma membrane. In certain embodiments, the structure component comprises all or part of one or more organelles, for example, the nucleus, endoplasmic reticulum, golgi apparatus, mitochondria, lysosomes or secretory vesicles or combinations thereof. The structure component may include any portion of an organelle, for example, the membrane of an organelle. The structure component may also include any substance which is included in the cytoplasm of a cell.

The structure component may include one or more proteins. In a suitable embodiment, the structure component includes one or more cellular proteins. One or more of these cellular proteins may be membrane associated proteins, for example, plasma membrane associated proteins. In one embodiment of the invention, the structure component includes adaptor proteins. Examples of adaptor proteins are AP-1, AP-2 and AP-3. Adaptor proteins and their characteristics are well known in the art and are discussed in, for example, Darsow et al., J. Cell Bio., 142, 913 (1998) which is incorporated in its entirety herein by reference. The one or more proteins may also include the substrate which is cleaved by the proteolytic domain of a *botulinum* toxin light chain component. For example, a protein included in the structure component may be SNAP-25.

The interaction between the light chain of *botulinum* type A and the structure component may contribute to localization of the toxin in a certain pattern. Therefore, the interaction may act to facilitate proteolysis by, for example, increasing the biological persistence and/or biological activity of the light chain.

A *botulinum* toxin heavy chain or portion thereof may also be associated with the light chain component when the light chain is interacting with the structure component.

In one embodiment, a *botulinum* toxin light chain component, when interacting with the structure component in a cell, may localize in the cell in a particular pattern. For example, localization of a *botulinum* toxin type A light chain component may be in a punctate or spotted pattern. For example, a *botulinum* type A light chain component may be localized in a punctate pattern on a cell membrane, for example, a plasma membrane. *Botulinum* type B light chain may localize in the cytoplasm. *botulinum* type E may localize to the plasma membrane but to a lesser degree than type A. *Botulinum* type E may also localize in the cytoplasm.

Methodologies to produce an isolated composition of the invention are available to those skilled in the art. For example, a composition may be isolated by isolating the plasma membrane from a cell after introduction of a light chain component, for example, light chain A, into a cell. The light chain may be introduced into the cell by, for example, electroporation or by endocytosis. In the case of introduction into the cell by endocytosis, a heavy chain component may be included with the light chain component to facilitate the endocytosis, for example, receptor mediated endocytosis, of the light chain. In such preparation process, the heavy chain component may also be isolated and be included in the composition.

After introduction into the cell, the light chain component associates or interacts with the substrate component forming a composition. The composition may be isolated by purification of the light chain component-structure component from the cell. Standard purification techniques known to those skilled in the art may be used to isolate a membrane and/or membrane associated protein(s) which is included in the structure component which interacts with the light chain component. Examples of conventional techniques for isolation and purification of the light chain component/structure component include immunoprecipitation and/or membrane purification techniques.

The light chain component may be crosslinked to a portion of the structure component before isolation. The technical procedures for cross linking of biomolecules using agents such as DTBP are well known to those skilled in the art.

In some embodiments, a composition of the invention may be prepared by mixing together a purified or a partially purified light chain component and a purified or a partially purified intracellular structure component under conditions which are effective to form the composition. Conditions important in forming the composition may include pH, ionic concentration and temperature.

The *botulinum* toxin light chain component of a composition, may be a modified *botulinum* toxin light chain. Modifications may be mutations and/or deletions as described elsewhere herein.

A modified light chain component may include a light chain A modified to remove a leucine based motif or other structure(s) which contributes to localization of the type A light chain to the plasma membrane thereby resulting in a light chain with a reduced ability to localize to a plasma membrane. This may result in a reduction in the biological activity and/or biological persistence of the light chain A. The biological persistence and/or activity of the modified light chain may be about 10% to about 90% that of an unmodified type A light chain.

Another modified light chain component may include a light chain A modified by adding one or more leucine based motifs, or other structure(s) which contributes to localization of the type A light chain to the plasma membrane, thereby resulting in a light chain with an increased ability to localize to a plasma membrane. This may result in an increase in the biological activity and/or biological persistence of the light chain A. The biological persistence and/or activity of the modified light chain may be about 1.5 to about 5 times that of an unmodified type A light chain.

Another modified light chain component may include a light chain B modified by adding one or more leucine based motifs, or other structure(s) which contributes to localization of the type A light chain to the plasma membrane, thereby resulting in a type B light chain with a increased ability to localize to a plasma membrane. This may result in an increase in the biological activity and/or biological persistence of the light chain A. The biological persistence and/or activity of the modified light chain may be about 1.5 to about 10 times that of an unmodified type B light chain.

A modified light chain component may include a light chain E modified by adding one or more leucine based motifs, or other structure(s) which contribute to localization of the type A light chain to the plasma membrane, thereby resulting in a light chain with an increased ability to localize to a plasma membrane. This may result in an increase in the biological activity and/or biological persistence of the light chain A. The biological persistence and/or activity of the modified light chain may be about 2 to about 20 times that of an unmodified type E light chain.

Compositions of the invention have many uses and applications, for example, in research science and medicine. Other uses and applications will be readily apparent to those skilled in the art.

In one broad aspect of the present invention, a method is provided for treating a condition using a modified neurotoxin. The conditions can include, for example, skeletal muscle conditions, smooth muscle conditions, pain and glandular conditions. The modified neurotoxin can also be used for cosmetics, for example, to treat brow furrows.

The neuromuscular disorders and conditions that can be treated with a modified neurotoxin include: for example, spasmodic dysphonia, laryngeal dystonia, oromandibular and lingual dystonia, cervical dystonia, focal hand dystonia, blepharospasm, strabismus, hemifacial spasm, eyelid disorders, spasmodic torticolis, cerebral palsy, focal spasticity and other voice disorders, spasmodic colitis, neurogenic bladder, anismus, limb spasticity, tics, tremors, bruxism, anal fissure, achalasia, dysphagia and other muscle tone disorders and other disorders characterized by involuntary movements of muscle groups can be treated using the present methods of administration. Other examples of conditions that can be treated using the present methods and compositions are lacrimation, hyperhydrosis, excessive salivation and excessive gastrointestinal secretions, as well as other secretory disorders. In addition, the present invention can be used to treat dermatological conditions, for example, reduction of brow furrows, reduction of skin wrinkles. The present invention can also be used in the treatment of sports injuries.

Borodic U.S. Pat. No. 5,053,005 discloses methods for treating juvenile spinal curvature, i.e. scoliosis, using *botulinum* type A. The disclosure of Borodic is incorporated in its entirety herein by reference. In one embodiment, using substantially similar methods as disclosed by Borodic, a modified neurotoxin can be administered to a mammal, preferably a human, to treat spinal curvature. In a suitable embodiment, a modified neurotoxin comprising *botulinum* type E fused with a leucine-based motif is administered. Even more preferably, a modified neurotoxin comprising *botulinum* type A-E with a leucine-based motif fused to the carboxyl terminal of its light chain is administered to the mammal, preferably a human, to treat spinal curvature.

In addition, the modified neurotoxin can be administered to treat other neuromuscular disorders using well known techniques that are commonly performed with *botulinum* type A. For example, the present invention can be used to treat pain, for example, headache pain, pain from muscle spasms and various forms of inflammatory pain. For example, Aoki U.S. Pat. No. 5,721,215 and Aoki U.S. Pat. No. 6,113,915 disclose methods of using *botulinum* toxin type A for treating pain. The disclosure of these two patents is incorporated in its entirety herein by reference.

Autonomic nervous system disorders can also be treated with a modified neurotoxin. For example, glandular malfunctioning is an autonomic nervous system disorder. Glandular malfunctioning includes excessive sweating and excessive salivation. Respiratory malfunctioning is another example of an autonomic nervous system disorder. Respiratory malfunctioning includes chronic obstructive pulmonary disease and asthma. Sanders et al. disclose methods for treating the autonomic nervous system; for example, treating autonomic nervous system disorders such as excessive sweating, excessive salivation, asthma, etc., using naturally existing *botulinum* toxins. The disclosure of Sander et al. is incorporated in its entirety by reference herein. In one embodiment, substantially similar methods to that of Sanders et al. can be employed, but using a modified neurotoxin, to treat autonomic nervous system disorders such as the ones discussed above. For example, a modified neurotoxin can be locally applied to the nasal cavity of the mammal in an amount sufficient to degenerate cholinergic neurons of the autonomic nervous system that control the mucous secretion in the nasal cavity.

Pain that can be treated by a modified neurotoxin includes pain caused by muscle tension, or spasm, or pain that is not associated with muscle spasm. For example, Binder in U.S. Pat. No. 5,714,468 discloses that headache caused by vascular disturbances, muscular tension, neuralgia and neuropathy can be treated with a naturally occurring *botulinum* toxin, for example *Botulinum* type A. The disclosures of Binder are incorporated in its entirety herein by reference. In one embodiment, substantially similar methods to that of Binder can be employed, but using a modified neurotoxin, to treat headache, especially the ones caused by vascular disturbances, muscular tension, neuralgia and neuropathy. Pain caused by muscle spasm can also be treated by an administration of a modified neurotoxin. For example, a *botulinum* type E fused with a leucine-based motif, preferably at the carboxyl terminal of the *botulinum* type E light chain, can be administered intramuscularly at the pain/spasm location to alleviate pain.

Furthermore, a modified neurotoxin can be administered to a mammal to treat pain that is not associated with a muscular disorder, such as spasm. In one broad embodiment, methods of the present invention to treat non-spasm related pain include central administration or peripheral administration of the modified neurotoxin.

For example, Foster et al. in U.S. Pat. No. 5,989,545 discloses that a *botulinum* toxin conjugated with a targeting moiety can be administered centrally (intrathecally) to alleviate pain. The disclosures of Foster et al. are incorporated in its entirety by reference herein. In one embodiment, substantially similar methods to that of Foster et al. can be employed, but using the modified neurotoxin according to this invention, to treat pain. The pain to be treated can be an acute pain, or preferably, chronic pain.

An acute or chronic pain that is not associated with a muscle spasm can also be alleviated with a local, peripheral administration of the modified neurotoxin to an actual or a perceived pain location on the mammal. In one embodiment, the modified neurotoxin is administered subcutaneously at or near the location of pain, for example, at or near a cut. In some embodiments, the modified neurotoxin is administered intramuscularly at or near the location of pain, for example, at or near a bruise location on the mammal. In some embodiments, the modified neurotoxin is injected directly into a joint of a mammal, for treating or alleviating pain caused by arthritic conditions. Also, frequent repeated injection or infusion of the modified neurotoxin to a peripheral pain location is within the scope of the present invention. However, given the long lasting therapeutic effects of the present invention, frequent injection or infusion of the neurotoxin can not be necessary. For example, practice of the present invention can provide an analgesic effect, per injection, for 2 months or longer, for example 27 months, in humans.

Without wishing to limit the invention to any mechanism or theory of operation, it is believed that when the modified neurotoxin is administered locally to a peripheral location, it inhibits the release of Neuro-substances, for example substance P, from the peripheral primary sensory terminal by inhibiting SNARE-dependent exocytosis. Since the release of substance P by the peripheral primary sensory terminal can cause or at least amplify pain transmission process, inhibition of its release at the peripheral primary sensory terminal will dampen the transmission of pain signals from reaching the brain.

In addition to having pharmacologic actions at the peripheral location, the modified neurotoxin of the present invention can also have inhibitory effects in the central nervous system, upon direct intrathecal administration, as set forth in U.S. Pat. No. 6,113,915, or upon peripheral administration, where presumably the modified toxin acts through retrograde transport via a primary sensory afferent. This hypothesis of retrograde axonal transport is supported by published data which shows that *botulinum* type A can be retrograde transported to the dorsal horn when the neurotoxin is injected peripherally. Thus, work by Weigand et al, *Nauny-Schmiedeberg's Arch. Pharmacol.* 1976; 292, 161-165, and Habermann, *Nauny-Schmiedeberg's Arch. Pharmacol.* 1974; 281, 47-56, showed that *botulinum* toxin is able to ascend to the spinal area by retrograde transport. As such, a modified neurotoxin, for example *botulinum* type A with one or more amino acids mutated from the leucine-based motif, injected at a peripheral location, for example intramuscularly, can be expected to be retrograde transported from the peripheral primary sensory terminal to a central region.

The amount of the modified neurotoxin administered can vary widely according to the particular disorder being treated, its severity and other various patient variables including size, weight, age, and responsiveness to therapy. Generally, the dose of modified neurotoxin to be administered will vary with the age, presenting condition and weight of the mammal, preferably a human, to be treated. The potency of the modified neurotoxin will also be considered.

Assuming a potency (for a *botulinum* toxin type A) which is substantially equivalent to $LD_{50}$=2,730 U in a human patient and an average person is 75 kg, a lethal dose (for a *botulinum* toxin type A) would be about 36 U/kg of a modified neurotoxin. Therefore, when a modified neurotoxin with such an $LD_{50}$ is administered, it would be appropriate to administer less than 36 U/kg of the modified neurotoxin into human subjects. Preferably, about 0.01 U/kg to 30 U/kg of the modified neurotoxin is administered. More preferably, about 1 U/kg to about 15 U/kg of the modified neurotoxin is administered. Even more preferably, about 5 U/kg to about 10 U/kg modified neurotoxin is administered. Generally, the modified neurotoxin will be administered as a composition at a dosage that is proportionally equivalent to about 2.5 cc/100 U. Those of ordinary skill in the art will know, or can readily ascertain, how to adjust these dosages for neurotoxin of greater or lesser potency. It is known that *botulinum* toxin type B can be administered at a level about fifty times higher that that used for a *botulinum* toxin type A for similar therapeutic effect. Thus, the units amounts set forth above can be multiplied by a factor of about fifty for a *botulinum* toxin type B.

Although examples of routes of administration and dosages are provided, the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14$^{th}$ edition, published by McGraw Hill). For example, the route and dosage for administration of a modified neurotoxin according to the present disclosed invention can be selected based upon criteria such as the solubility characteristics of the modified neurotoxin chosen as well as the types of disorder being treated.

The modified neurotoxin can be produced by chemically linking the leucine-based motif to a neurotoxin using conventional chemical methods well known in the art. For example, *botulinum* type E can be obtained by establishing and growing cultures of *Clostridium botulinum* in a fermenter, and then harvesting and purifying the fermented mixture in accordance with known procedures.

The modified neurotoxin can also be produced by recombinant techniques. Recombinant techniques are preferable for producing a neurotoxin having amino acid sequence regions from different Clostridial species or having modified amino acid sequence regions. Also, the recombinant technique is preferable in producing *botulinum* type A with the leucine-based motif being modified by deletion. The technique includes steps of obtaining genetic materials from natural sources, or synthetic sources, which have codes for a cellular binding moiety, an amino acid sequence effective to translocate the neurotoxin or a part thereof, and an amino acid sequence having therapeutic activity when released into a cytoplasm of a target cell, preferably a neuron. In a suitable embodiment, the genetic materials have codes for the biological persistence enhancing component, preferably the leucine-based motif, the $H_C$, the $H_N$ and the light chain of the Clostridial neurotoxins and fragments thereof. The genetic constructs are incorporated into host cells for amplification by first fusing the genetic constructs with a cloning vectors, such as phages or plasmids. Then the cloning vectors are inserted into a host, for example, *Clostridium* sp., *E. coli* or other prokaryotes, yeast, insect cell line or mammalian cell lines. Following the expressions of the recombinant genes in host cells, the resultant proteins can be isolated using conventional techniques.

There are many advantages to producing these modified neurotoxins recombinantly. For example, to form a modified neurotoxin, a modifying fragment, or component must be attached or inserted into a neurotoxin. The production of neurotoxin from anaerobic *Clostridium* cultures is a cumbersome and time-consuming process including a multi-step purification protocol involving several protein precipitation steps and either prolonged and repeated crystallization of the toxin or several stages of column chromatography. Significantly, the high toxicity of the product dictates that the procedure must be performed under strict containment (BL-3). During the fermentation process, the folded single-chain neurotoxins are activated by endogenous Clostridial proteases through a process termed nicking to create a dichain. Sometimes, the process of nicking involves the removal of approximately 10 amino acid residues from the single-chain to create the dichain form in which the two chains remain covalently linked through the intrachain disulfide bond.

The nicked neurotoxin is much more active than the unnicked form. The amount and precise location of nicking varies with the serotypes of the bacteria producing the toxin. The differences in single-chain neurotoxin activation and, hence, the yield of nicked toxin, are due to variations in the serotype and amounts of proteolytic activity produced by a given strain. For example, greater than 99% of *Clostridial botulinum* serotype A single-chain neurotoxin is activated by the Hall A *Clostridial botulinum* strain, whereas serotype B and E strains produce toxins with lower amounts of activation (0 to 75% depending upon the fermentation time). Thus, the high toxicity of the mature neurotoxin plays a major part in the commercial manufacture of neurotoxins as therapeutic agents.

The degree of activation of engineered Clostridial toxins is, therefore, an important consideration for manufacture of these materials. It would be a major advantage if neurotoxins such as *botulinum* toxin and tetanus toxin could be expressed, recombinantly, in high yield in rapidly-growing bacteria (such as heterologous *E. coli* cells) as relatively non-toxic single-chains (or single chains having reduced toxic activity) which are safe, easy to isolate and simple to convert to the fully-active form.

With safety being a prime concern, previous work has concentrated on the expression in *E. coli* and purification of individual H and light chains of tetanus and *botulinum* toxins; these isolated chains are, by themselves, non-toxic; see Li et al., *Biochemistry* 33:7014-7020 (1994); Zhou et al., *Biochemistry* 34:15175-15181 (1995), hereby incorporated by reference herein. Following the separate production of these peptide chains and under strictly controlled conditions the H and light chains can be combined by oxidative disulphide linkage to form the neuroparalytic di-chains.

EXAMPLES

The following non-limiting examples provide those of ordinary skill in the art with specific suitable methods to treat non-spasm related pain within the scope of the present invention and are not intended to limit the scope of the invention.

Example 1

Treatment of Pain Associated with Muscle Disorder:

An unfortunate 36 year old woman has a 15 year history of temporomandibular joint disease and chronic pain along the masseter and temporalis muscles. Fifteen years prior to evaluation she noted increased immobility of the jaw associated with pain and jaw opening and closing and tenderness along each side of her face. The left side is originally thought to be worse than the right. She is diagnosed as having temporomandibular joint (TMJ) dysfunction with subluxation of the joint and is treated with surgical orthoplasty meniscusectomy and condyle resection.

She continues to have difficulty with opening and closing her jaw after the surgical procedures and for this reason, several years later, a surgical procedure to replace prosthetic joints on both sides is performed. After the surgical procedure progressive spasms and deviation of the jaw ensues. Further surgical revision is performed subsequent to the original operation to correct prosthetic joint loosening. The jaw continues to exhibit considerable pain and immobility after these surgical procedures. The TMJ remained tender as well as the muscle itself. There are tender points over the temporomandibular joint as well as increased tone in the entire muscle. She is diagnosed as having post-surgical myofascial pain syndrome and is injected with the modified neurotoxin into the masseter and temporalis muscles; the modified neurotoxin is *botulinum* type E comprising a leucine-based motif. The particular dose as well as the frequency of administrations depends upon a variety of factors within the skill of the treating physician.

Several days after the injections she noted substantial improvement in her pain and reports that her jaw feels looser. This gradually improves over a 2 to 3 week period in which she notes increased ability to open the jaw and diminishing pain. The patient states that the pain is better than at any time in the last 4 years. The improved condition persists for up to 27 months after the original injection of the modified neurotoxin.

Example 2

Treatment of Pain Subsequent to Spinal Cord Injury:

A patient, age 39, experiencing pain subsequent to spinal cord injury is treated by intrathecal administration, for example, by spinal tap or by catherization (for infusion) to the spinal cord, with the modified neurotoxin; the modified neurotoxin is *botulinum* type E comprising a leucine-based motif. The particular toxin dose and site of injection, as well as the frequency of toxin administrations, depend upon a variety of factors within the skill of the treating physician, as previously set forth. Within about 1 to about 7 days after the modified neurotoxin administration, the patient's pain is substantially reduced. The pain alleviation persists for up to 27 months.

Example 3

Peripheral Administration of a Modified Neurotoxin to Treat "Shoulder-Hand Syndrome":

Pain in the shoulder, arm, and hand can develop, with muscular dystrophy, osteoporosis and fixation of joints. While most common after coronary insufficiency, this syndrome can occur with cervical osteoarthritis or localized shoulder disease, or after any prolonged illness that requires the patient to remain in bed.

A 46 year old woman presents a shoulder-hand syndrome type pain. The pain is particularly localized at the deltoid region. The patient is treated by a bolus injection of a modified neurotoxin subcutaneously to the shoulder; preferably the modified neurotoxin is *botulinum* type E comprising a leucine-based motif. The modified neurotoxin can also be, for example, modified *botulinum* type A, B, C1, C2, D, E, F or G which comprise a leucine-based motif. The particular dose as well as the frequency of administrations depends upon a variety of factors within the skill of the treating physician, as previously set forth. Within 1-7 days after modified neurotoxin administration the patient's pain is substantially alleviated. The duration of the pain alleviation is from about 7 to about 27 months.

Example 4

Peripheral Administration of a Modified Neurotoxin to Treat Postherapeutic Neuralgia:

Postherapeutic neuralgia is one of the most intractable of chronic pain problems. Patients suffering this excruciatingly painful process often are elderly, have debilitating disease, and are not suitable for major interventional procedures. The diagnosis is readily made by the appearance of the healed lesions of herpes and by the patient's history. The pain is intense and emotionally distressing. Postherapeutic neuralgia can occur anywhere, but is most often in the thorax.

A 76 year old man presents a postherapeutic type pain. The pain is localized to the abdomen region. The patient is treated by a bolus injection of a modified neurotoxin intradermally to the abdomen; the modified neurotoxin is, for example, *botulinum* type A, B, C1, C2, D, E, F and/or G. The modified neurotoxin comprises a leucine-based motif and/or additional tyrosine-based motifs. The particular dose as well as the frequency of administration depends upon a variety of factors within the skill of the treating physician, as previously set forth. Within 1-7 days after modified neurotoxin administration the patient's pain is substantially alleviated. The duration of the pain alleviation is from about 7 to about 27 months.

Example 5

Peripheral Administration of a Modified Neurotoxin to Treat Nasopharyngeal Tumor Pain:

These tumors, most often squamous cell carcinomas, are usually in the fossa of Rosenmuller and can invade the base of the skull. Pain in the face is common. It is constant, dull-aching in nature.

A 35 year old man presents a nasopharyngeal tumor type pain. Pain is found at the lower left cheek. The patient is treated by a bolus injection of a modified neurotoxin intramuscularly to the cheek, preferably the modified neurotoxin is *botulinum* type A, B, C1, C2, D, E, F or G comprising additional biological persistence enhancing amino acid derivatives, for example, tyrosine phosphorylations. The particular dose as well as the frequency of administrations depends upon a variety of factors within the skill of the treating physician. Within 1-7 days after modified neurotoxin administration the patient's pain is substantially alleviated. The duration of the pain alleviation is from about 7 to about 27 months.

Example 6

Peripheral Administration of a Modified Neurotoxin to Treat Inflammatory Pain:

A patient, age 45, presents an inflammatory pain in the chest region. The patient is treated by a bolus injection of a modified neurotoxin intramuscularly to the chest, preferably the modified neurotoxin is *botulinum* type A, B, C1, C2, D, E, F or G comprising additional tyrosine-based motifs. The particular dose as well as the frequency of administrations depends upon a variety of factors within the skill of the treating physician, as previously set forth. Within 1-7 days after modified neurotoxin administration the patient's pain is substantially alleviated. The duration of the pain alleviation is from about 7 to about 27 months.

Example 7

Treatment of Excessive Sweating:

A male, age 65, with excessive unilateral sweating is treated by administering a modified neurotoxin. The dose and frequency of administration depends upon degree of desired effect. Preferably, the modified neurotoxin is *botulinum* type A, B, C1, C2, D, E, F and/or G. The modified neurotoxins comprise a leucine-based motif. The administration is to the gland nerve plexus, ganglion, spinal cord or central nervous system. The specific site of administration is to be determined by the physician's knowledge of the anatomy and physiology of the target glands and secretory cells. In addition, the appropriate spinal cord level or brain area can be injected with the toxin. The cessation of excessive sweating after the modified neurotoxin treatment is up to 27 months.

Example 8

Post Surgical Treatments:

A female, age 22, presents a torn shoulder tendon and undergoes orthopedic surgery to repair the tendon. After the surgery, the patient is administered intramuscularly with a modified neurotoxin to the shoulder. The modified neurotoxin can *botulinum* type A, B, C, D, E, F, and/or G wherein one or more amino acids of a biological persistence enhancing component are deleted from the toxin. For example, one or more leucine residues can be deleted from and/or mutated from the leucine-based motif in *botulinum* toxin serotype A. Alternatively, one or more amino acids of the leucine-based motif can be substituted for other amino acids. For example, the two leucines in the leucine-based motif can be substituted for alanines. The particular dose as well as the frequency of administrations depends upon a variety of factors within the skill of the treating physician. The specific site of administration is to be determined by the physician's knowledge of the anatomy and physiology of the muscles. The administered modified neurotoxin reduces movement of the arm to facilitate the recovery from the surgery. The effect of the modified neurotoxin is for about five weeks or less.

Example 9

Cloning, Expression and Purification of the *Botulinum* Neurotoxin Light Chain Gene:

This example describes methods to clone and express a DNA nucleotide sequence encoding a *botulinum* toxin light chain and purify the resulting protein product. A DNA sequence encoding the *botulinum* toxin light chain can be amplified by PCR protocols which employ synthetic oligonucleotides having sequences corresponding to the 5' and 3' end regions of the light chain gene. Design of the primers can allow for the introduction of restriction sites, for example, Stu I and EcoR I restriction sites into the 5' and 3' ends of the *botulinum* toxin light chain gene PCR product. These restriction sites can be subsequently used to facilitate unidirectional subcloning of the amplification products. Additionally, these primers can introduce a stop codon at the C-terminus of the light chain coding sequence. Chromosomal DNA from *C. botulinum*, for example, strain HallA, can serve as a template in the amplification reaction.

The PCR amplification can be performed in a 0.1 mL volume containing 10 mM Tris-HCl (pH 8.3), 50 mM KCl, 1.5 mM MgCl2, 0.2 mM of each deoxynucleotide triphosphate (dNTP), 50 pmol of each primer, 200 ng of genomic DNA and 2.5 units of Taq DNA polymerase. The reaction mixture can be subjected to 35 cycles of denaturation (1 minute at 94° C.), annealing (2 minutes at 55° C.) and polymerization (2 minutes at 72° C.). Finally, the reaction can be extended for an additional 5 minutes at 72° C.

The PCR amplification product can be digested with for example, Stu I and EcoR I, to release the light chain encoding, cloned, PCR DNA fragment. This fragment can then be purified by, for example, agarose gel electrophoresis, and ligated into, for example, a Sma I and EcoR I digested pBluescript II SK phagemid. Bacterial transformants, for example, *E. coli*, harboring this recombinant phagemid can be identified by standard procedures, such as blue/white screening. Clones comprising the light chain encoding DNA can be identified by DNA sequence analysis performed by standard methods. The cloned sequences can be confirmed by comparing the cloned sequences to published sequences for *botulinum* light chains, for example, Binz, et al., in *J. Biol. Chem.* 265, 9153 (1990), Thompson et al., in *Eur. J. Biochem.* 189, 73 (1990) and Minton, Clostridial Neurotoxins, The Molecular Pathogenesis of Tetanus and Botulism p. 161-191, Edited by C. Motecucco (1995).

The light chain can be subcloned into an expression vector, for example, pMal-P2. pMal-P2 harbors the malE gene encoding MBP (maltose binding protein) which is controlled by a strongly inducible promoter, $P_{tac}$.

To verify expression of the *botulinum* toxin light chain, a well isolated bacterial colony harboring the light chain gene containing pMal-P2 can be used to inoculate L-broth containing 0.1 mg/ml ampicillin and 2% (w/v) glucose, and grown overnight with shaking at 30° C. The overnight cultures can be diluted 1:10 into fresh L-broth containing 0.1 mg/ml of ampicillin and incubated for 2 hours. Fusion protein expression can be induced by addition of IPTG to a final concentration of 0.1 mM. After an additional 4 hour incubation at 30° C., bacteria can be collected by centrifugation at 6,000×g for 10 minutes.

A small-scale SDS-PAGE analysis can confirm the presence of a 90 kDa protein band in samples derived from IPTG-induced bacteria. This MW would be consistent with the predicted size of a fusion protein having MBP (~40 kDa) and *botulinum* toxin light chain (~50 kDa) components.

The presence of the desired fusion proteins in IPTG-induced bacterial extracts can be confirmed by western blotting using the polyclonal anti-L chain probe described by Cenci di Bello et al., in *Eur. J. Biochem.* 219, 161 (1993). Reactive bands on PVDF membranes (Pharmacia; Milton Keynes, UK) can be visualized using an anti-rabbit immunoglobulin conjugated to horseradish peroxidase (BioRad; Hemel Hempstead, UK) and the ECL detection system (Amersham, UK). Western blotting results typically confirm the presence of the dominant fusion protein together with several faint bands corresponding to proteins of lower MW than the fully sized fusion protein. This observation suggests that limited degradation of the fusion protein occurred in the bacteria or during the isolation procedure.

To produce the subcloned light chain, pellets from 1 liter cultures of bacteria expressing the wild-type *botulinum* neurotoxin light chain proteins can be resuspended in column buffer [10 mM Tris-HCl (pH 8.0), 200 mM NaCl, 1 mM EGTA and 1 mM DTT] containing 1 mM phenylmethanesulfonyl fluoride (PMSF) and 10 mM benzamidine, and lysed by sonication. The lysates can be cleared by centrifugation at 15,000×g for 15 minutes at 4° C. Supernatants can be applied to an amylose affinity column [2×10 cm, 30 ml resin] (New England BioLabs; Hitchin, UK). Unbound proteins can be washed from the resin with column buffer until the eluate is free of protein as judged by a stable absorbance reading at 280 nm. The bound MBP-L chain fusion protein can be subsequently eluted with column buffer containing 10 mM maltose. Fractions containing the fusion protein can be pooled and dialyzed against 20 mM Tris-HCl (pH 8.0) supplemented with 150 mM NaCl, 2 mM, CaCl2 and 1 mM DTT for 72 hours at 4° C.

The MBP-L chain fusion proteins can be purified after release from the host bacteria. Release from the bacteria can be accomplished by enzymatically degrading or mechanically disrupting the bacterial cell membrane. Amylose affinity chromatography can be used for purification. Recombinant wild-type or mutant light chains can be separated from the sugar binding domains of the fusion proteins by site-specific cleavage with Factor Xa. This cleavage procedure typically yields free MBP, free light chains and a small amount of uncleaved fusion protein. While the resulting light chains present in such mixtures can be shown to possess the desired activities, an additional purification step can be employed. For example, the mixture of cleavage products can be applied to a second amylose affinity column which binds both the MBP and uncleaved fusion protein. Free light chains can be isolated in the flow through fraction.

Example 10

Reconstitution of Native Light Chain, Recombinant Wild-Type Light Chain with Purified Heavy Chain:

Native heavy and light chains can be dissociated from a BoNT with 2 M urea, reduced with 100 mM DTT and then purified according to established chromatographic procedures. For example, Kozaki et al. (1981, *Japan J. Med. Sci. Biol.* 34, 61) and Maisey et al. (1988, *Eur. J. Biochem.* 177, 683). A purified heavy chain can be combined with an equimolar amount of either native light chain or a recombinant light chain. Reconstitution can be carried out by dialyzing the samples against a buffer consisting of 25 mM Tris (pH 8.0), 50 μM zinc acetate and 150 mM NaCl over 4 days at 4° C. Following dialysis, the association of the recombinant light chain and native heavy chain to form disulfide linked 150 kDa dichains is monitored by SDS-PAGE and/or quantified by densitometric scanning.

Example 11

Production of a Modified Neurotoxin with an Enhanced Biological Persistence:

A modified neurotoxin can be produced by employing recombinant techniques in conjunction with conventional chemical techniques.

A neurotoxin chain, for example a *botulinum* light chain that is to be fused with a biological persistence enhancing component to form a modified neurotoxin can be produced recombinantly and purified as described in example 9.

The recombinant neurotoxin chain derived from the recombinant techniques can be covalently fused with (or coupled to) a biological persistence enhancing component, for example a leucine-based motif, a tyrosine-based motif and/or an amino acid derivative. Peptide sequences comprising biological persistence enhancing components can be synthesized by standard t-Boc/Fmoc technologies in solution or solid phase as is known to those skilled in the art. Similar synthesis techniques are also covered by the scope of this invention, for example, methodologies employed in Milton et al. (1992, *Biochemistry* 31, 8799-8809) and Swain et al. (1993, *Peptide Research* 6, 147-154). One or more synthesized biological persistence enhancing components can be fused to the light chain of *botulinum* type A, B, C1, C2, D, E, F or G at, for example, the carboxyl terminal end of the toxin.

The fusion of the biological persistence enhancing components is achieved by chemical coupling using reagents and techniques known to those skilled in the art, for example PDPH/EDAC and Traut's reagent chemistry.

Alternatively, a modified neurotoxin can be produced recombinantly without the step of fusing the biological persistence enhancing component to a recombinant *botulinum* toxin chain. For example, a recombinant neurotoxin chain, for example, a *botulinum* light chain, derived from the recombinant techniques of example 9 can be produced with a biological persistence enhancing component, for example a leucine-based motif, a tyrosine-based motif and/or an amino acid derivative. For example, one or more DNA sequences encoding biological persistence enhancing components can be added to the DNA sequence encoding the light chain of *botulinum* type A, B, C1, C2, D, E, F or G. This addition can be done by any number of methods used for site directed mutagenesis which are familiar to those skilled in the art.

The recombinant modified light chain containing the fused or added biological persistence enhancing component can be reconstituted with a heavy chain of a neurotoxin by the method described in example 10 thereby producing a complete modified neurotoxin.

The modified neurotoxins produced according to this example have an enhanced biological persistence. Preferably, the biological persistence is enhanced by about 20% to about 300% relative to an identical neurotoxin without the additional biological persistence enhancing component(s).

Example 12

Production of a Modified Neurotoxin with a Reduced Biological Persistence:

A modified neurotoxin with a reduced biological persistence can be produced by employing recombinant techniques. For example, a *botulinum* light chain derived from the recombinant techniques of example 9 can be produced without a biological persistence enhancing component. For example, one or more leucine-based motifs, tyrosine-based motifs and/or amino acid derivatives can be mutated. For example, one or more DNA sequences encoding biological persistence enhancing components can be removed from the DNA sequence encoding the light chain of *botulinum* type A, B, C1, C2, D, E, F or G. For example, the DNA sequence encoding the leucine based motif can be removed from the DNA sequence encoding *botulinum* type A light chain. Removal of the DNA sequences can be done by any number of methods familiar to those skilled in the art.

The recombinant modified light chain with the deleted biological persistence enhancing component can be reconstituted with a heavy chain of a neurotoxin by the method described in example 10 thereby producing a complete modified neurotoxin.

The modified neurotoxin produced according to this example has a reduced biological persistence. Preferably, the biological persistence is reduced by about 20% to about 300% relative to an identical neurotoxin, for example *botulinum* type A, with the leucine-based motif.

Although the present invention has been described in detail with regard to certain suitable methods, other embodiments, versions, and modifications within the scope of the present invention are possible. For example, a wide variety of modified neurotoxins can be effectively used in the methods of the present invention in place of Clostridial neurotoxins. Also, the corresponding genetic codes, i.e. DNA sequence, to the modified neurotoxins are also considered to be part of this invention. Additionally, the present invention includes peripheral administration methods wherein two or more modified neurotoxins, for example *botulinum* type E with a fused leucine-based motif and *botulinum* type B comprising a leucine-based motif, are administered concurrently or consecutively. While this invention has been described with respect to various specific examples and embodiments, it is to be understood that the invention is not limited thereto and that it can be variously practiced with the scope of the following claims.

Example 13

Production of a Modified Neurotoxin with a Reduced Biological Persistence:

Localization to the cellular membrane is likely a key factor in determining the biological persistence of *botulinum* toxins. This is because localization to a cell membrane can protect the localized protein from intracellular protein degrading complexes.

It is well known and generally accepted that the biological persistence of *botulinum* type B neurotoxin is shorter than the biological persistence of *botulinum* type A neurotoxin. In this work, it was demonstrated that when the *botulinum* toxin type A light chain is truncated, which comprises removing the leucine-based motif, the light chain substantially loses its ability to localize to the cellular membrane in its characteristic pattern. In fact, truncated type A light chain localizes to the cellular membrane in a pattern similar to that of *botulinum* toxin type B light chain.

Therefore, it can be hypothesized that truncated *botulinum* type A has a reduced biological persistence and/or a reduced biological activity similar to that of *botulinum* toxin type B.

Example 14

Production of a Modified Neurotoxin with an Altered Biological Persistence:

Localization to the cellular membrane is likely a key factor in determining the biological persistence of *botulinum* toxins. This is because localization to a cell membrane can protect the localized protein from intracellular protein degrading complexes.

In this work, it was demonstrated that when the *botulinum* toxin type A light chain is mutated, changing the two leucines at positions 427 and 428 to alanines (FIG. 3), the light chain substantially loses its ability to localize to the cellular membrane in its characteristic pattern.

From this data it can be concluded that the mutated *botulinum* type A has an altered biological persistence.

Example 15

In Vitro Cleavage of SNAP 25 by Truncated LC/A:

As illustrated by FIG. 9, an in vitro ELISA assay was carried out by the inventors demonstrating that a truncated LC/A in vitro cleaves SNAP-25 substrate less efficiently than does non-truncated LC/A. The data displayed is not a measure of inhibition of exocytosis but a measure of the in vitro formation of SNAP-25 cleavage. The assay was carried out as follows:

Materials:

BirA-SNAP25$_{128-206}$—this is a recombinant substrate for LC/A, consisting of a BirA signal sequence fused to the N-terminus of residues 128-206 of SNAP25. This fusion construct was produced in *E. coli* and the BirA signal sequence was biotinylated by the *E. coli*. Microtiter plates were coated with streptavidin. The toxin used was BoNT/A complex or LC/A constructs. The primary antibody was anti-SNAP25$_{197}$ antibody. This antibody recognizes the C-terminus of SNAP25 following cleavage by Type A toxin (BirA-SNAP25$_{128-197}$). The secondary antibody was goat, anti-rabbit IgG conjugated to horseradish peroxidase. The ImmunoPure TMB substrate was from Pierce, a colorimetric substrate for horseradish peroxidase. The antibody that recognizes the cleaved product SNAP25$_{197}$ is specific for that cleaved product and does not recognize the full length uncleaved substrate SNAP25$_{206}$.

Method:

BirA-SNAP25$_{128-206}$ was bound to streptavidin on a microtiter plate. To the plates were added serial dilutions of BoNT/A 900 kDa complex, His6-S-nativeLC/A, or His6-S-truncLC/A-His6. All toxin samples were pre-incubated with DTT (this is not required for the LC/A constructs, but they were treated the same as the BoNT/A complex). The toxin samples were incubated with the substrate for 90 minutes at 37° C. The toxin was removed and the bound substrate was incubated with anti-SNAP25$_{197}$ antibody. Unbound antibody was washed away and the plates were then incubated with the secondary antibody (anti-rabbit IgG conjugated to horseradish peroxidase). Unbound antibody was again washed away and a colorimetric assay for horseradish peroxidase was performed. The assay was quantified by reading the absorbance at 450 nm.

In other work by the inventors disclosed herein the light chain constructs that were expressed in the PC-12 cells were expressed directly in the PC-12 cells and do not contain any tags. The light chain constructs that have been expressed from E. coli for these in vitro assays contain affinity tags for purification purposes (these tags are not present on the proteins expressed in the PC-12 cells, as disclosed herein). The LC/A expressed in PC12 was the fusion protein GFP-LC/A. Between the GFP and the LC/A there is a set of Gly to separate both proteins.

An explanation of the various constructs follows:

Complex (red in the graph)—this is BoNT/A 900 kDa complex isolated from C. botulinum Truncated LC/A—a construct lacking 8 amino acids at the N-terminus and 22 amino acids at the C-terminus. However, this construct does contain a 6-histidine and an S-tag at the N-terminus as well as a 6-histidine tag at the C-terminus.

Dialyzed Truncated LC/A—same as Truncated LC/A, but imidazole resulting from the purification has been removed.

Full LC/A (dark green in graph)—native LC/A construct (full-length), but containing the N-terminal 6-histidine and S-tag. Does not have the C-terminal 6-histidine.

Dialyzed Full LC/A (light green in graph)—same as Full LC/A, but imidazole resulting from the purification has been removed.

Figure 10:
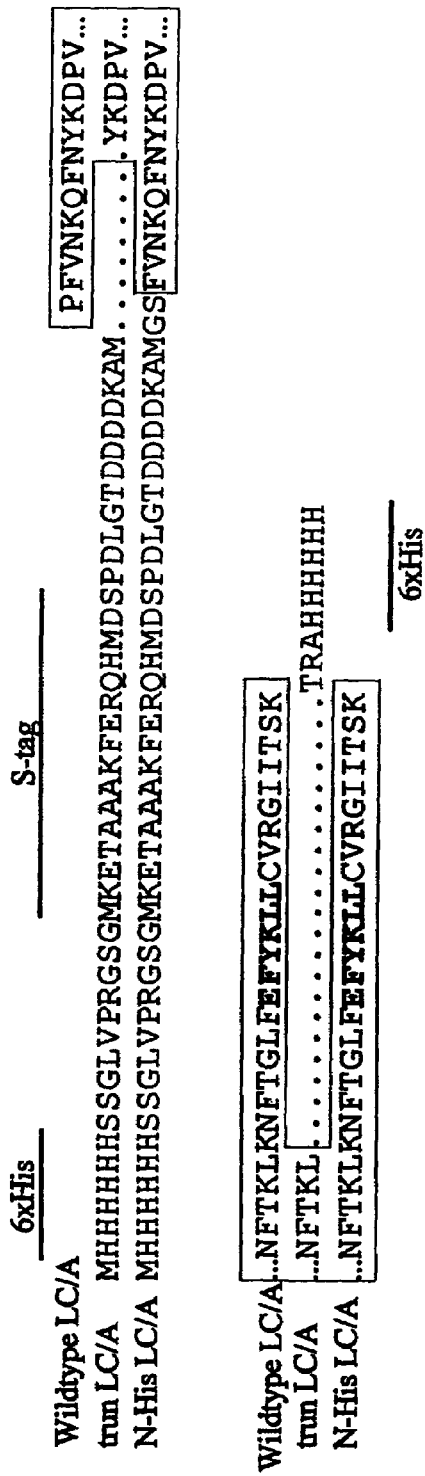
FIG. 10 shows a comparison of LC/A constructs expressed from *E. coli* for in vitro analysis. The LC/A (WT) sequences shown are amino acids 2-14 of SEQ ID NO: 29 (Amino terminus) and amino acids 412-438 of SEQ ID NO: 29 (Carboxyl Terminus). The LC/A (ΔN8/ΔC22) sequences shown are SEQ ID NO: 25 (Amino terminus) and SEQ ID NO: 26 (Carboxyl Terminus). The N-His LC/A (WT) sequences shown are SEQ ID NO: 148 (Amino terminus) and amino acids 412-438 of SEQ ID NO: 29 (Carboxyl Terminus).

To graphically depict these differences, FIG. 10 shows the very N-terminus and the very C-terminus of these constructs (the middle portion of the LC/A proteins is not shown). What is referred to as Wildtype corresponds to the native LC/A that the inventors had expressed directly in the PC-12 cells (this is construct that the inventors demonstrated activity with via Western blot analysis of the cleaved SNAP25 product). Truncated LC/A is the truncated light chain containing the His and S-tags. N-His-LC/A is what was referred to as Full LC/A in FIG. 9.

Example 16A

Intracellular Localization of Botulinum Toxin Type A Light Chain:

The sequences of LC/A, LC/B, and LC/E were analyzed for the presence of localization signals. A putative dileucine motif was identified at the C-terminus of LC/A and was unique to that serotype. The role of the dileucine motif in LC/A activity as well as localization was investigated. The inventors found that a LC/A construct that lacks 8 N-terminal and 22 C-terminal amino acids (including the dileucine motif) retains minimal activity and is mislocalized when expressed in PC12 cells. The specific role of the dileucine motif was elucidated by generating a LL-->AA double mutant. The LL-->AA mutant has minimally reduced activity, but is mislocalized when expressed in PC12 cells. The mislocalization is similar to that recently reported for the LL-->AA mutant of VAMP4. Localization and activity data are reported, supporting the hypothesis that the dileucine motif is important for proper intracellular localization of LC/A.

Materials and Methods:

LC from BoNT/A (Allergan Hall A), N— and C-terminal truncated LC/A, and double mutant LC/A (LL-->AA) were cloned into pQBI25 (Qbiogene) as both N— and C-terminal GFP fusion proteins: GFP-LCA, LCA-GFP; GFP-LCA(LL-->AA); LCA(LL-->AA)-GFP; GFP-LCA(ΔN/ΔC); LCA(ΔN/ΔC)-GFP.

Undifferentiated PC12 (rat pheochromocytoma) cells were transfected with Lipofectamine2000 (Invitrogen) and then were differentiated with NGF (Harlan).

Expression and integrity of the light chains were assessed by immuno-precipitation with a GFP monoclonal antibody (3E6, Qbiogene), followed by western blot with antibodies to GFP (pAb, Santa Cruz) or LCA (pAb, Allergan).

Catalytic activity of PC12 expressed LC-GFP fusion proteins was determined by western blot analysis with the following antibodies:

SMI-81 (Stemberger) and N-19 (Santa Cruz): Recognize full-length SNAP-25 as well as SNAP25$_{197}$ pAb SNAP25$_{197}$: Polyclonal antibody generated at Allergan specific to the BoNT/A cleaved peptide.

In vitro activity of rLC's was determined by SNAP25 ELISA assay.

Recombinant LC (rLC/A), truncated LC (trunLC/A(ΔN8/ΔC22)), and double mutant LC/A(LL-->AA) were cloned into pET-30(+) vectors containing polyHis affinity tags. The LC's were purified via Ni$^{+2}$ affinity chromatography.

A biotinylated substrate corresponding to SNAP25(134-206) was immobilized on a streptavidin-coated microtiter plate. The appropriate LC constructs and 900 kDa BoNT/A complex were added to substrate coated plates. Protease activity was determined by quantitating the formation of SNAP(134-197) with a pAb (Allergan) specific for the proteolysis product. The activity of 900 kDa BoNT/A complex was determined as a control.

Localization of the GFP fusions in paraformaldehyde fixed cells was determined by confocal microscopy (Leica). Cell slices from the middle of the cell are shown in the images.

FIG. 3 shows LC/A sequence with the 8 N-terminal and 22 C-terminal amino acids that were deleted in the LC/A (ΔN8/ΔC22) construct underlined. The dileucine motif is bracketed from the top with an asterisk. The two leucine residues that were mutated to alanines are the two leucines in the dileucine motif. Mutation of LL-->AA has been demonstrated to disrupt appropriate trafficking and localization of membrane associated proteins.

Figure 11:
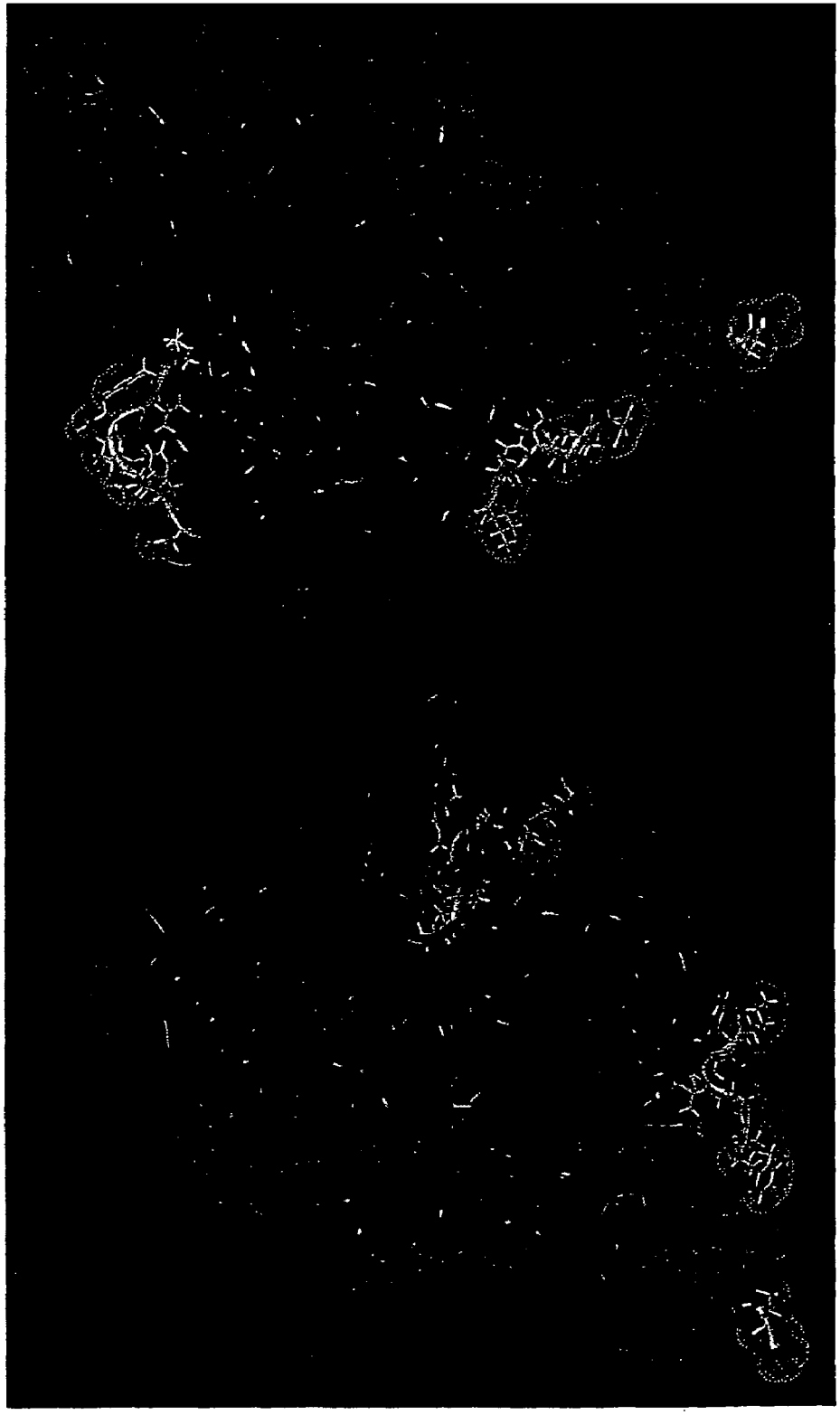
FIG. 11 shows a ribbon diagram of LC/A with a Connolly surface overlay. The coordinates were extracted from the holotoxin x-ray structure (Protein Data Bank accession I.D. 3BTA) from Lacy et al., *Nat. Struct. Biol.,* 5, 898 (1998). Residues 1-430 are shown in the structure, the 8 C-terminal amino acids were not resolved in the holotoxin structure.

FIG. 11 shows a ribbon diagram of LC/A with a Connolly surface overlay from Lacy et al., *Nat. Struct. Biol.*, 5, 898 (1998) which is incorporated in its entirety herein by reference. The N- and C-terminal regions of interest are yellow with amino acid side-chains included. The dileucine motif is red and the $Zn^{2+}$ atom is a silver sphere. The structure was extracted from the holotoxin x-ray structure and includes residues 1-430 (the 17 C-terminal amino acids were not resolved in the structure).

Figure 12:
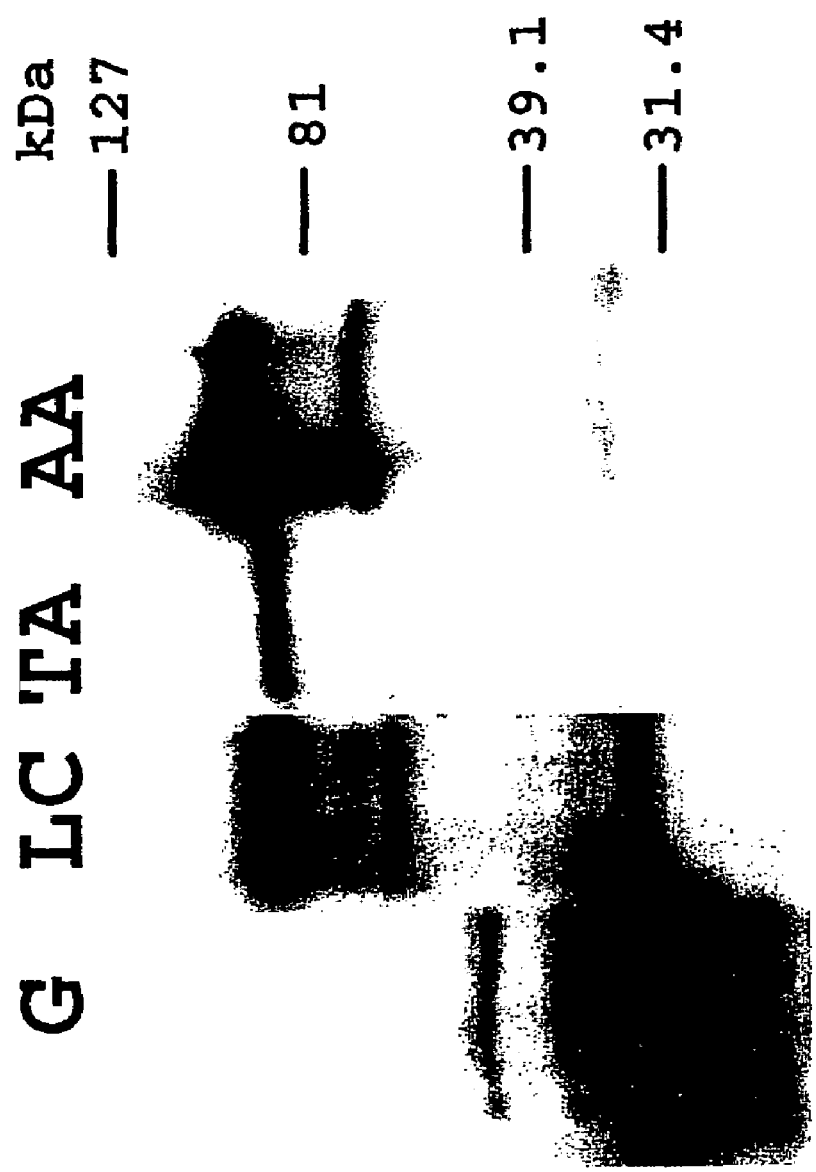
FIG. 12. shows the detection of GFP-LC fusion proteins expressed in differentiated PC12 cells by western blot.
Figure 13:
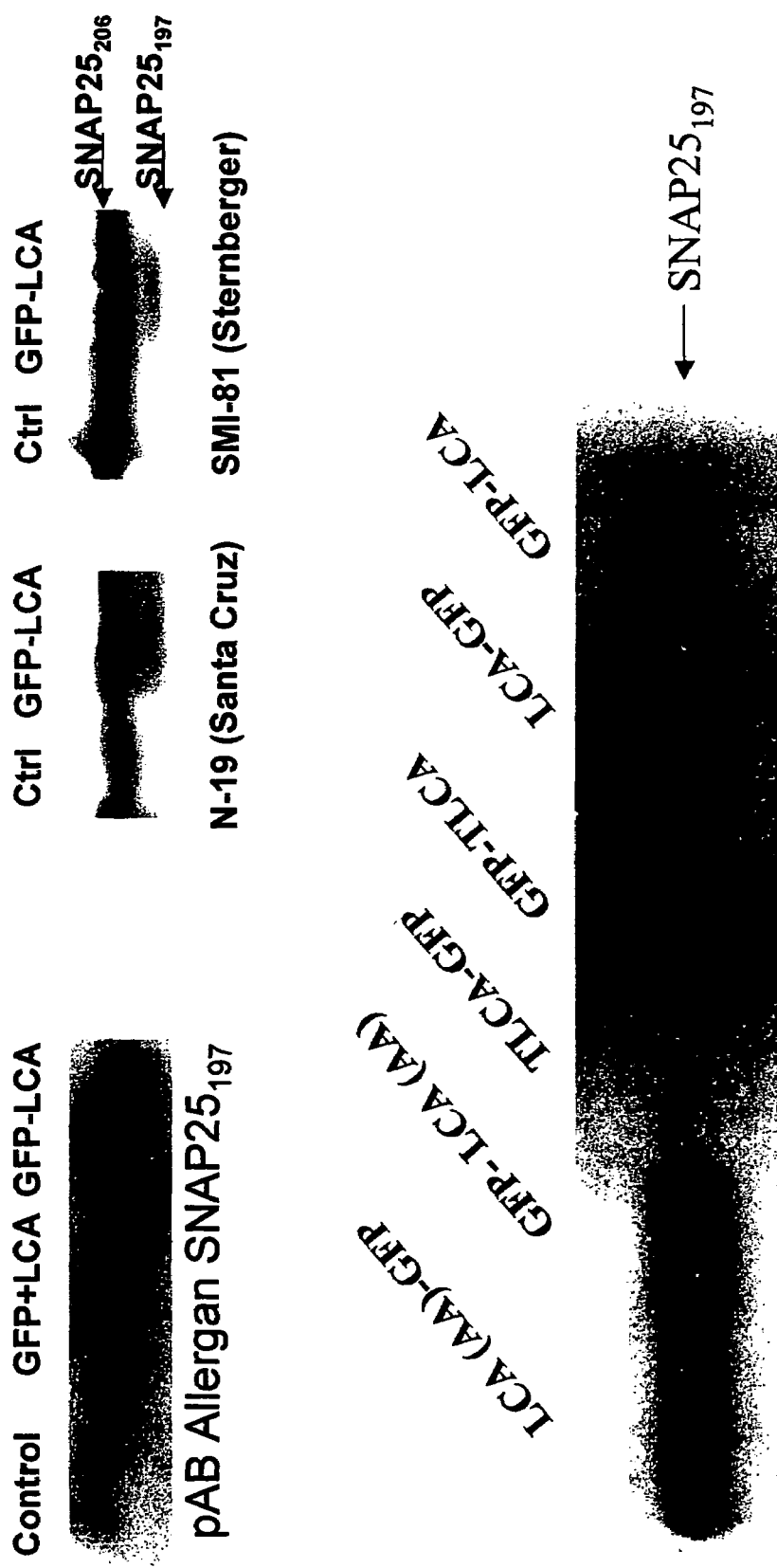
FIG. 13 is a western blot showing GFP-LC activity.

FIGS. 12 and 13 show GFP-LC/A recombinant fusion constructs that are expressed and active when transfected in PC12 cells.

FIG. 12 shows the detection of GFP-LC fusion proteins expressed in differentiated PC12 cells by western blot. GFP-LC Fusion Proteins Detected in PC12 Lysates. Lanes: G, GFP; LC, GFP-LC/A; AA, GFP-LC/A(LL-->AA); TA, GFP-LCA(ΔN8/ΔC22). Expression and integrity of the fusion proteins was also assessed with a pAb to LCA.

FIG. 13 shows expressed LC's are Active Proteases. PC12 cells transfected with and expressing the appropriate GFP-LC fusion construct were collected and lysed. Activity was assessed by western blot using either antibodies specific to the cleaved product of LCA ($SNAP25_{197}$) or to the N-terminus of SNAP25 (recognizes both cleaved and uncleaved SNAP25). Truncated LC/A is expressed less efficiently and appears to be much less active than LCA. LCA(AA) appears to be slightly less active than LC/A in PC12 cells. N-19 (Santa Cruz) SMI-81 (Stemberger) are antibodies to N-terminus $SNAP25_{206}$.

Figure 14:
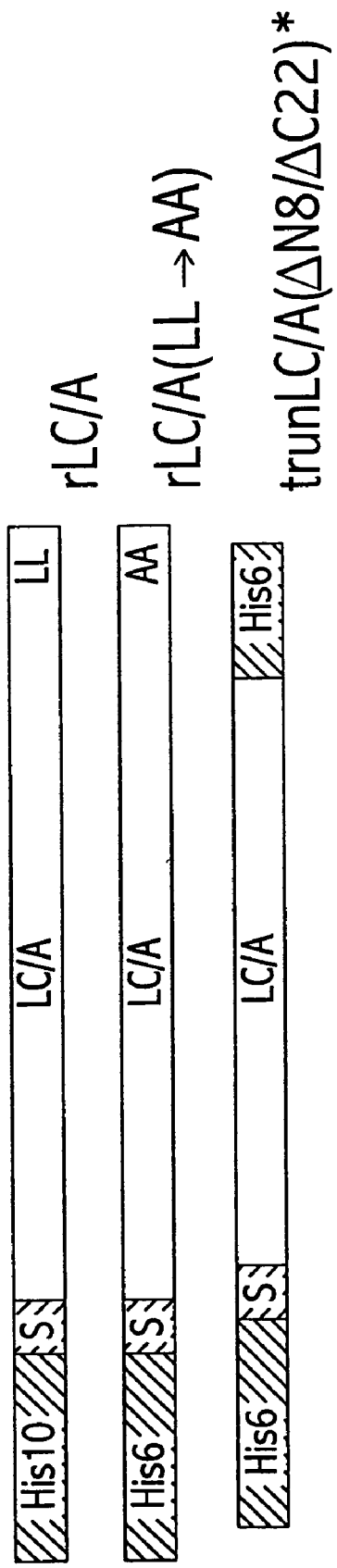
FIG. 14 shows the *E. coli* recombinant constructs for expression of rLC/A and mutants.
Figure 15:
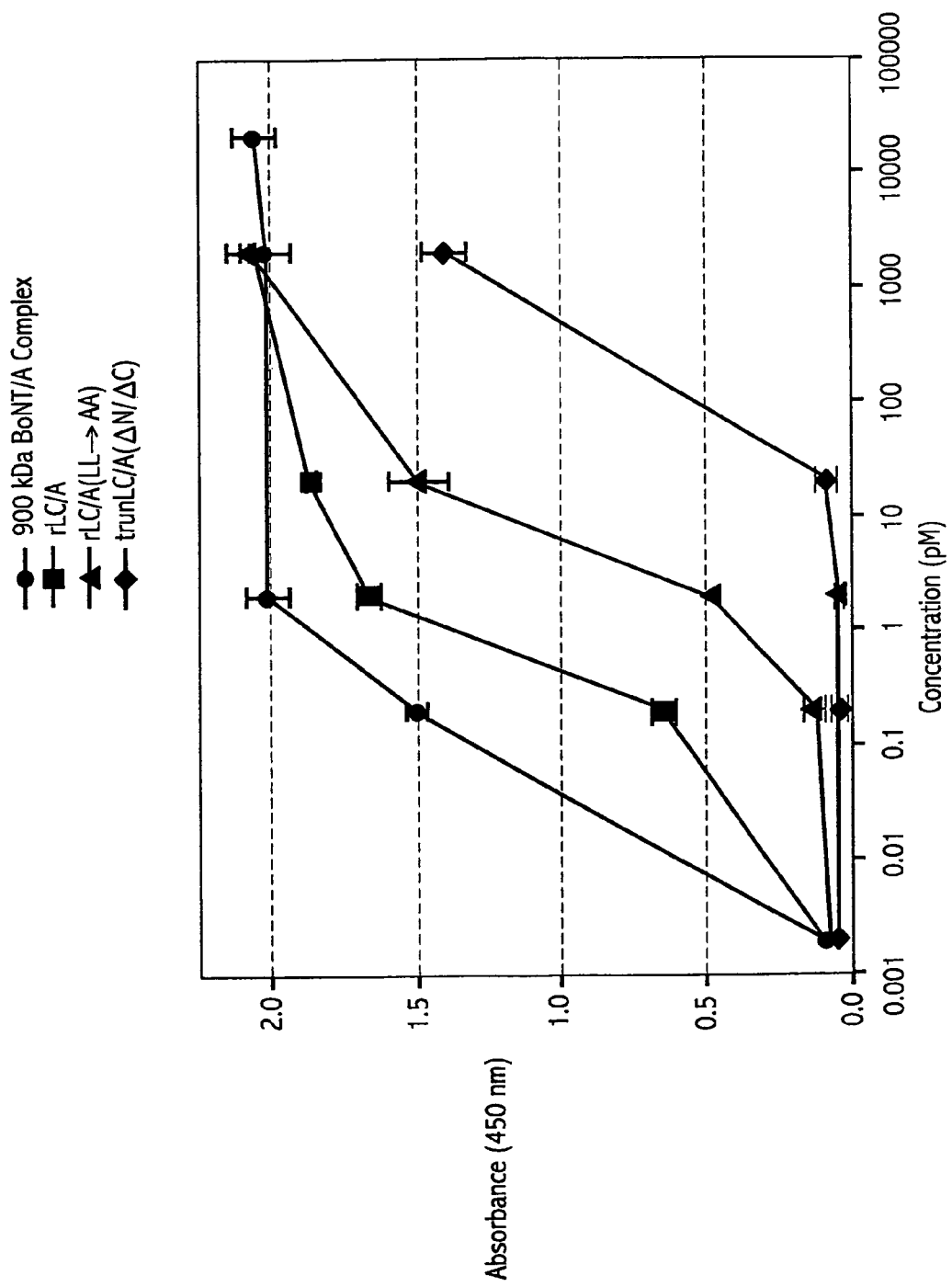
FIG. 15 shows a SNAP-25 ELISA assay data showing in vitro activity of *E. coli* expressed rLC/A and mutants.

FIGS. 14 and 15 show *E. coli* expression and in vitro activity of rLC/A and mutants FIG. 14 shows *E. coli* expression of rLC/A and mutants. * corresponds to the minimal essential domain of LC/A reported in Kadkhodayan et al, *Prot. Exp. Purif.*, 19, 125 (2000) which is incorporated in its entirety herein by reference.

FIG. 15 shows a SNAP-25 ELISA assay showing in vitro activity of *E. coli* expressed rLC/A and mutants. SNAP25 (134-206) was immobilized on a streptavidin-coated microtitre plate. The formation of SNAP-25(134-197) was quantified with an Ab specific to that product. As a control 900 kDa BoNT/A complex was included. rLC/A(LL-->AA) is approximately 10 fold less active than rLC/A. Truncated LC/A is approximately 1000 fold less active than rLC/A.

Figure 16:
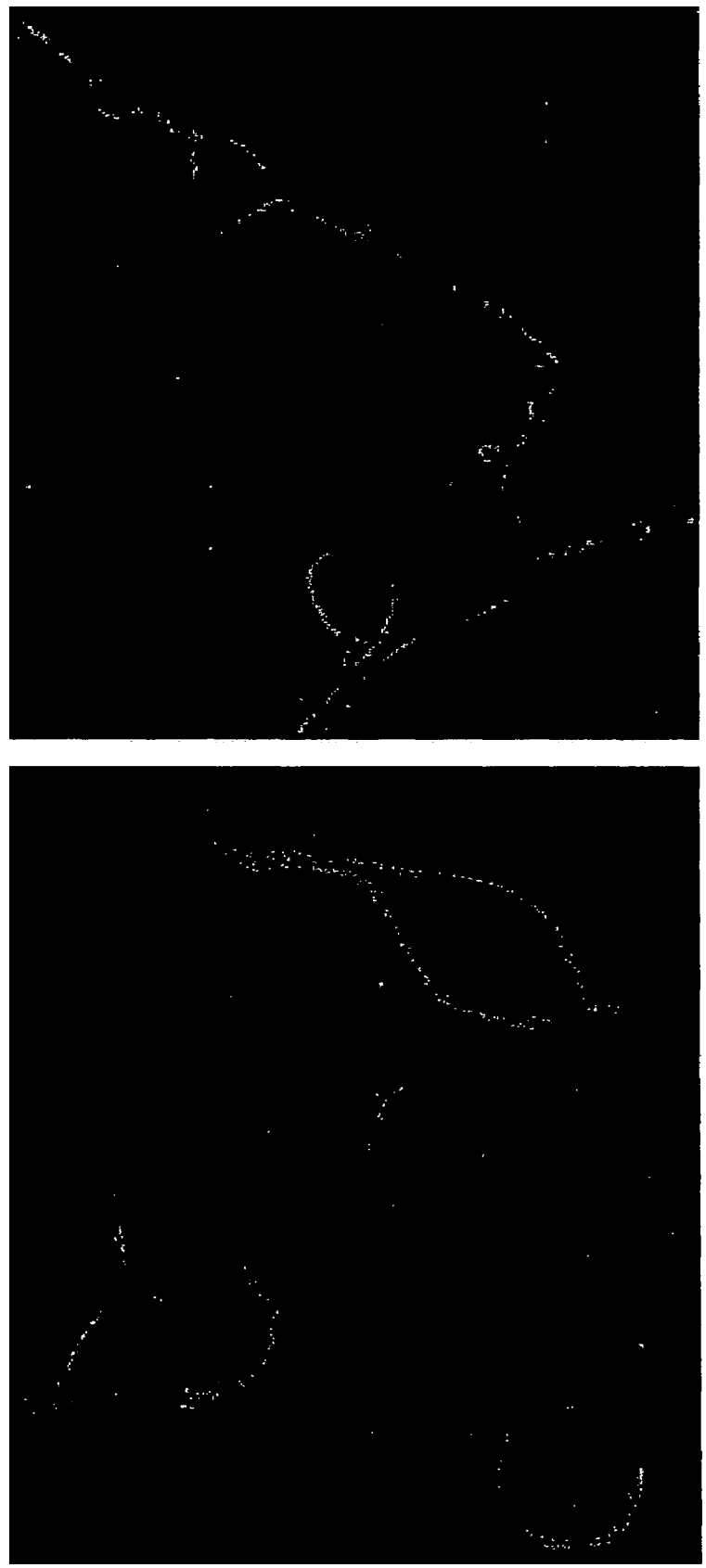
FIG. 16 shows localization of GFP-LC/A at the plasma membrane of PC12 cells by confocal microscopy. Images are from slices at approximately the middle of the cell.

FIG. 16 shows PC12 cells transfected with plasmids encoding GFP-LCA. Confocal images were captured at approximately the middle of the cell. Subcellular localization of the light chain in PC12 cells is shown. Localization of LC/A at the plasma membrane can clearly be observed. LCA-GFP displays the same localization pattern (data not shown).

FIG. 17 shows PC12 cells transfected with plasmids encoding GFP-LCA(ΔN/ΔC) and LCA(ΔN/ΔC)-GFP (data not shown). The N— and C-terminal truncated form of LC/A may be localized to an internal structure rather than at the plasma membrane.

FIG. 18 shows confocal images of GFP-LCA(LL-->AA) expressed in PC12 cells. Mutation to the dileucine motif disrupts LC/A localization of the plasma membrane. The dileucine mutant is localized in a more diffuse pattern than GFP-LCA. The localization pattern is similar to that seen for VAMP4 dileucine mutant as reported in Penden et al, *J. Biol. Chem.*, 276, 49183 (2001) which is incorporated in its entirety herein by reference.

The results shown in at least FIGS. 3 and 11 to 18 demonstrate that the presence of a dileucine motif is critical for the proper intracellular localization of LC/A and may be important for the long duration of action of BoNT/A.

Additional studies showed that a GFP-LCA construct with the eight amino acid residues of SEQ ID NO: 27 (PFVNKQFN) deleted from the N-terminus (no C-terminus deletion) localized in PC12 cells a very similar pattern to the localization in PC12 cells of a truncated GFP-LCA construct with both the C and N terminus deletions.

Further studies showed that a GFP-LCA construct with the twenty two amino acid residues of SEQ ID NO: 28 (KNFTGLFEFYKLLCVRGIITSK) deleted from the C-terminus (no N-terminus deletion) localized in PC12 cells in a very similar manner to that of the GFP-LCA(LL-->AA) mutant.

A GFP-LCA construct with both the eight amino acid residues of SEQ ID NO: 27 (PFVNKQFN) deleted from the N-terminus and the twenty two amino acid residues of SEQ ID NO: 28 (KNFTGLFEFYKLLCVRGIITSK) deleted from the C-terminus accumulated intracellularly.

Example 16B

The first 30 residues of the amino-terminus (N-term) and the last 50 residues of the carboxyl-terminal (C-term) of the amino acid sequences of *botulinum* toxin serotypes A through G light chains (LC) are shown in Table 2.

TABLE 2

| Toxin | N-term (AAs 1-30) of LC | SEQ ID NO: | C-term (last 50 AAs) of LC | SEQ ID NO: |
|---|---|---|---|---|
| BoNT/A | MPFVNKQFNYKDPVNGVDIAYIKIPNAGQM | 39 | GFNLRNTNLAANFNGQNTEINNMNFTKLKNFTGLFEFYKLLCVRGIITSK | 40 |
| BoNT/B | MPVTINNFNYNDPIDNDNIIMMEPPFARGT | 41 | YTIEEGFNISDKNMGKEYRGQNKAINKQAYEEISKEHLAVYKIQMCKSVK | 42 |
| BoNT/C$_1$ | MPITINNFNYSDPVDNKNILYLDTHLNTLA | 43 | NIPKSNLNVLFMGQNLSRNPALRKVNPENMLYLFTKFCHKAIDGRSLYNK | 44 |
| BoNT/D | MTWPVKDFNYSDPVNDNDILYLRIPQNKLI | 45 | YTIRDGFNLTNKGFNIENSGQNIERNPALQKLSSESVVDLFTKVCLRLTK | 46 |
| BoNT/E | MPKINSFNYNDPVNDRTILYIKPGGCQEFY | 47 | GYNINNLKVNFRGQNANLNPRIITPITGRGLVKKIIRFCKNIVSVKGIRK | 48 |

TABLE 2-continued

| Toxin | N-term (AAs 1-30) of LC | SEQ ID NO: | C-term (last 50 AAs) of LC | SEQ ID NO: |
|---|---|---|---|---|
| BoNT/F | MPVAINSFNYNDPVNDDTI LYMQIPYEEKS | 49 | TVSEGFNIGNLAVNNRGQS IKLNPKIIDSIPDKGLVEK IVKFCKSVIPRK | 50 |
| BoNT/G | MPVNIKNFNYNDPINNDDI IMMEPFNDPGP | 51 | QNEGFNIASKNLKTEFNGQ NKAVNKEAYEEISLEHLVI YRIAMCKPVMYK | 52 |

Alterations in the amino acid sequence of these serotypes can include amino acid substitutions, mutations, deletions, or various combinations of these alterations. Such alterations can be engineered in the first thirty amino acids (AAs) in the N-terminus of the light chain and/or the last fifty AAs in the C-terminus of the light chain using recombinant DNA technological methods that are standard in the art.

Examples of amino acid sequence substitutions include the replacement of one or more contiguous or non-contiguous amino acids in the first 30 amino acids of the N-terminus and/or the last 50 amino acids of the C-terminus of the light chain with an equal number and placement of amino acids that differ from the wild-type sequence. Substitutions can be conservative or non-conservative of the character of the amino acid. For example, the amino acid valine at a specific position in the wild-type sequence can be replaced with an alanine in the same position in the substituted sequence. Furthermore, basic residues such as arginine or lysine can be substituted for highly hydrophobic residues such as tryptophan. A proline or histidine residue may be substituted in order to form or disrupt a potentially important structural or catalytic element of the protein. Some examples of amino acid substitutions are indicated by bold underlined text in the sequences described in Table 3.

TABLE 3

| Toxin | N-term (AAs 1-30) of LC | SEQ ID NO: | C-term (last 50 AAs) of LC | SEQ ID NO: |
|---|---|---|---|---|
| BoNT/A | MPFANKQFNYKDPVNGVDI AYIKIPNAGQM | 53 | GFNLRNTNLAANFNGQNTE INNMNRTKLKNFTGLFEFY KLLCVRGIITSK | 54 |
| BoNT/A | MPFVNKQFNKKDPVNGVDI AYIKIPNAGQM | 55 | GFNLRNTNLAANFNGQNTE INNMNFTKLKNAAGLFEFY KLLCVRGIITSK | 56 |
| BoNT/A | MPFVNKQFNYKDPVNGVDI ARIKIPNAGQM | 57 | GFNLRNTNLAANHNGQNTE INNMNFTKLKNFTGLFEFY KLLCVRGIITSK | 58 |
| BoNT/A | MPFVNKHFNYKDPVNGVDI AYIKIPNAGQM | 59 | GFNLRNTNLAANFNGQNTE INNMNFTKLKNFTGLFEFY KLLCARGIITSK | 60 |
| BoNT/B | MPATINNFNYNDPIDNDNI IMMEPPFARGT | 61 | YTIEEGFNISDKNMGKEYR GQNKAINKQAYEEISKEHL AVYKIRMCKSVK | 62 |
| BoNT/B | MPVTINNFNYNDPIDNDNI IAAEPPFARGT | 63 | YTIEEGFNISDKNMGKEYR GQNKAINKQAYEEISKEHL AVRKIQMCKSVK | 64 |
| BoNT/B | MPVTINNFNRNDPIDNDNI IMMEPPFARGT | 65 | YTIEEGFNISDKNMGKEYR GQNKAINKQAKEEISKEHL AVYKIQMCKSVK | 66 |
| BoNT/C₁ | MPITINNKNYSDPVDNKNI LYLDTHLNTLA | 67 | NIPKSNLNVLFMGQNLSRN PALRKVNPENMLYLFTKFC HKAIDGRSLRNK | 68 |
| BoNT/D | MTWPAKDFNYSDPANDNDI LYLRIPQNKLI | 69 | YTIRDGFNLTNKGFNIENS GQNIERNPALQKLSSESVV DLFTKACLRLTK | 70 |
| BoNT/E | MPKINSFNYNDPANDRTIL YIKPGGCQEFY | 71 | GYNINNLKVNFRGQNANLN PRIITPITGRGHVKKIIRF CKNIVSVKGIRK | 72 |
| BoNT/E | MPKINSRNYNDPVNDRTIL YIKPGGCQEFY | 73 | GYNINNLKVNFRGQNANLN PRIITPITGRGLVKKIIRF CKNAASVKGIRK | 74 |
| BoNT/E | MPKINSFNYNDPVNDRTIL YIKPGGCQEFR | 75 | GYNINNLKVNFRGQNANLN PRIITPITGRGLVKKIIRF CKNIVSAKGIRK | 76 |
| BoNT/F | MPAAINSFNYNDPVNDDTI LYMQIPYEEKS | 77 | TVSEGFNIGNLAVNNRGQS IKLNPKIIDSIPDKGLVEK IVKFCKSAIPRK | 78 |
| BoNT/G | MPVNIKNHNYNDPINNDDI IMMEPFNDPGP | 79 | QNEGFNIASKNLKTEFNGQ NKAVNKEAYEEISLEHLVI YRIAMCKPAMYK | 80 |

Examples of amino acid sequence mutations include changes in the first 30 amino acids of the N-terminus and/or the last 50 amino acids of the C-terminus of the light chain sequence such that one or several amino acids are added, substituted and/or deleted such that the identity, number and position of amino acids in the wild-type light chain sequence is not necessarily conserved in the mutated light chain sequence. Some examples of amino acid sequence mutations are described in Table 4, in which additions of amino acids are shown in bold underlined text, and deletions are indicated by dashes in the sequences shown.

TABLE 4

| Toxin | N-term (AAs 1-30) of LC | SEQ ID NO: | C-term (last 50 AAs) of LC | SEQ ID NO: |
|---|---|---|---|---|
| BoNT/A | MPFVNKQFNYKDPVNGVDI AYIKIPH---- | 81 | GFNLRNTNLAANFNGQNTE INNMNAAAAAAAAAA---- ---CVRGIITSK | 82 |
| BoNT/A | MAAA---- NYKDPVNGVDIAYIKIPNA GQM | 83 | GKNLRNTNLAANFNGQNTE INNMNFTKLKNFTGLFEFY K-CVRGIITSK | 84 |
| BoNT/A | MPFVNKQFNYKDPVNGVDI AR----NAGQM | 85 | GFNLRNTNLAA---- HNTEINNMNFTKLKNFTGL FEFYKLLCVRGIITSK | 86 |
| BoNT/A | MPKVNKQFN---- VNGVDIAYIKIPNAGQM | 87 | GFNLRNTNLAANFNGQNTE INNMNFTKLKNFTGLFEFR R--------TSK | 88 |
| BoNT/B | MPVTINNFNYNDPIDNDNI IAAAAAAARGT | 89 | YTIPPGFNISDKNMGKEYR GQNKAINKQAYEEISKEH- ------------ | 90 |
| BoNT/B | MPA---- FNYNDPIDNDNIIMMEPPF ARGT | 91 | YTIEEGFNISDKNMGKEYR GQNKAAAAAAAAEEISKEHL AVYKIQMCKSVK | 92 |
| BoNT/B | MPVTINNFNR--------- -MMEPPFARGT | 93 | YTIEEGFNISDKNMGKEYR GQNKAINKQAY------ AAAAAAIQMCKSVK | 94 |
| BoNT/C₁ | M--------- SDPVDNKNILYLDTHLNTL A | 95 | NIPKSNLNVLFMGQNLSRN PALRKVNPENMLAAA--- CHKAIDGRSLYNK | 96 |
| BoNT/D | MTRPVKD---- DPVNDNDILYLRIPQNKLI | 97 | YTIRDGFNLTNKGFNIENS GQNIERNPALQKL------ DLPPKVCLRLTK | 98 |
| BoNT/E | MPKINSPPNYNDPVNDRTI LYIKPGGCQEFY | 99 | GYNINNLKVNFRGQNANLN PRIITPITGRGLVKKAAAA CKNIVSVKGIRK | 100 |
| BoNT/E | MPKINSFNYNDPAAAANDR TILYIKPGGCQEFY | 101 | GYNINNLKVNFRGQNANLN PRIITPITGRGLV--- HRFCKNIVSVKGIRK | 102 |
| BoNT/E | MPKINSFNYNDPVNDRTIL KIKPGGCKEFY | 103 | GYNINNLKVNFRGQNANLN PRIITPITGRGLPP----- ------------ | 104 |
| BoNT/F | MP------ NYNDPVNDDTILYMQIPYE EKS | 105 | TVSEGFNIGNLAVNNRGQS IKLNPKIIDSIPDKGAAAA AA--CKSVIPRK | 106 |
| BoNT/G | MPVNIPP---- DPINNDDIIMMEPFNDPGP | 107 | QNEGFNIASKNLKTEFNGQ NKAVNKEAY--------- -----AAAAAAA | 108 |

Examples of amino acid sequence deletions include the removal of one or more contiguous or non-contiguous amino acids from the first 30 amino acids of the N-terminus and/or the last 50 amino acids of the C-terminus of the light chain sequence. Some examples of amino acid sequence deletions are indicated by dashes in the sequences shown in Table 5.

TABLE 5

| Toxin | N-term (AAs 1-30) of LC | SEQ ID NO: | C-term (last 50 AAs) of LC | SEQ ID NO: |
|---|---|---|---|---|
| BoNT/A | M-------- YKDPVNGVDIAYIKIPNAG QM | 109 | GFNLRNTNLAANFNGQNTE INNMNFTKLKNFTGLFEFY K---------- | 110 |
| BoNT/A | MPFVNKQ------ VNGVDIAYIKIPNAGQM | 111 | GFNLRNTNLAANFNGQNTE INNMNFTKLK--------- -LLCVRGIITSK | 112 |
| BoNT/A | MPFVNKQFNYKDP------ AYIKIPNAGQM | 113 | GFNLRNTNLAANFNGQNTE INNMN-------- GLFEFYKLLCVRGIITSK | 114 |

TABLE 5-continued

| Toxin | N-term (AAs 1-30) of LC | SEQ ID NO: | C-term (last 50 AAs) of LC | SEQ ID NO: |
|---|---|---|---|---|
| BoNT/A | MPFVNKQFNYKDPVNGVDIA---------- | 115 | GFNLRN----------NTEINNMNFTKLKNFTGLFEFYKLLCVRGIITSK | 116 |
| BoNT/B | MPVTINNFNYNDPIDNDNIIMME------- | 117 | YTI-----ISDKNMGKEYRGQNKAINKQAYEEISKEHLAVYKIQMCKSVK | 118 |
| BoNT/B | MPVTINNFNYND----------EPPFARGT | 119 | YTIEEGFNISD--------GQNKAINKQAYEEISKEHLAVYKIQMCKSVK | 120 |
| BoNT/B | MP--------NDPIDNDNIIMMEPPFARGT | 121 | YTIEEGFNISDKNMGKEYRGQNKAINKQA------------KIQMCKSVK | 122 |
| BoNT/C$_1$ | MPI-------SDPVDNKNILYLDTHLNTLA | 123 | NIPKSNLNVLFMGQNLSRNPALRKV----------KFCHKAIDGRSLYNK | 124 |
| BoNT/D | MTW----------VNDNDILYLRIPQNKLI | 125 | YTIRDGFNLTNKGFNIENSGQNIERNPA----------DLFTKVCLRLTK | 126 |
| BoNT/E | MP--------DPVNDRTILYIKPGGCQEFY | 127 | GYNINNLKVNFRGQNANLNPRIITPI----------RFCKNIVSVKGIRK | 128 |
| BoNT/E | MPKINSFNYN----------IKPGGCQEFY | 129 | GYNINN------GQNANLNPRIITPITGRGLVKKIIRFCKNIVSVKGIRK | 130 |
| BoNT/E | MPKINSFNYNDPVNDRTILYIK-------- | 131 | GYNINNLKVNFRGQNANLNPRIITPITGRGLVKKIIR---------KGIRK | 132 |
| BoNT/F | MPVAINSFNYNDPVNDDTILYMQIP----- | 133 | TVSEGFNIGNLAVNNRGQSIKLNPKIIDSIPD--------KFCKSVIPRK | 134 |
| BoNT/G | M--------------------------- | — | QNEGFNIASKNLKTEFNGQNKAVNKEA------------RIAMCKPVMYK | 135 |

Example 16C

In some embodiments of the present invention, the biological persistence and/or the enzymatic activity of a toxin can be altered by structurally modifying the toxin. In some embodiments, the structural modification includes the substitution, mutation or deletion of amino acids within the toxin. In a suitable embodiment, the structural modification includes a chimeric fusion construct in which a biological persistence-enhancing component or an enzymatic activity-enhancing component may be fused to, swapped for, or incorporated within a terminal end of the light chain of a *botulinum* toxin. In some embodiments, the structural modification includes a chimeric fusion construct in which a biological persistence-reducing component or an enzymatic activity-reducing component may be fused to, swapped for, or incorporated within a terminal end of the light chain of a *botulinum* toxin. In a suitable embodiment, the persistence- or activity-enhancing or persistence- or activity-reducing component is an N-terminal region including the first 30 amino acids of a light chain of a *botulinum* toxin, or a C-terminal region including the last 50 amino acids of a light chain of a *botulinum* toxin. This biological persistence- or enzymatic activity-enhancing component or biological persistence- or enzymatic activity-reducing component is swapped for, fused to, or incorporated within an N— and/or C-terminus of a light chain of a *botulinum* toxin to enhance or reduce its biological persistence and/or enzymatic activity.

In some embodiments, the fusion of, addition to, or swapping of the N-terminal region of the light chain of BoNT/A into a chimeric construct results in an increase in biological persistance and/or enzymatic activity. In some embodiments, a substituted, mutated, or deleted N-terminal region of the light chain of BoNT/A within a chimeric construct results in a decrease in biological persistance and/or enzymatic activity. In some embodiments, the fusion of, addition to, or swapping of the C-terminal region of the light chain of BoNT/A into a chimeric construct results in an increase in biological persistance and/or enzymatic activity. In some embodiments, a substituted, mutated, or deleted C-terminal region of the light chain of BoNT/A within a chimeric construct results in a decrease in biological persistance and/or enzymatic activity.

Generally, it is suitable that the chimeric toxin has a biological persistence of about 20% to 300% greater than an identical toxin without the structural modification. The biological persistence of the chimeric toxin may be enhanced by about 100%. That is, for example, the modified *botulinum* neurotoxin including the biological persistence-enhancing component is able to cause a substantial inhibition of neurotransmitter release (for example, acetylcholine) from a nerve terminal for about 20% to about 300% longer than a neurotoxin without the structural modification.

Similarly, it is suitable that the *chimeric botulinum* toxin light chain has an altered enzymatic activity. For example, the chimeric toxin can exhibit a reduced or an enhanced inhibition of exocytosis (such as exocytosis of a neurotransmitter) from a target cell with or without any alteration in the biological persistence of the modified neurotoxin. Altered enzymatic activities include increased or decreased efficiency or potency, increased or decreased localization to the plasma membrane, increased or decreased substrate specificity, and/or increased or decreased rate of proteolysis of SNAP/SNARE proteins. An increase in enzymatic activity can be from 1.5 to 5 times greater than the biological activity of the native or unmodified light chain. For example, the chimeric *botulinum* neurotoxin including the enzymatic activity-enhancing component is able to cause a substantial inhibition of neurotransmitter release (for example, acetylcholine) from a nerve terminal due to an increased rate of proteolysis of the SNAP-25 substrate as compared to a neurotoxin without the structural modification.

It has been observed that a recombinant construct with both the eight amino acid residues of SEQ ID NO: 27 (PFVNKQFN) deleted from the N-terminus and the twenty-two amino acid residues of SEQ ID NO: 28 (KNFTGLFE-FYKLLCVRGIITSK) deleted from the C-terminus of the light chain of *botulinum* toxin A exhibits a reduced activity such that the effective concentration ($EC_{50}$) required to cleave the SNAP-25 substrate is nearly ten-fold greater than that of a similar construct with only the C-terminal twenty-two amino acid deletion ($EC_{50}$ ΔN8ΔC22 = 4663 pM vs. $EC_{50}$Δ C22 =566 pM). The recombinant light chain of *botulinum* toxin A was used as a control ($EC_{50}$ rLC/A =7 pM), and, therefore, as compared to the rLC/A construct, a 666-fold greater concentration of the ΔNΔ8C22 construct is required. A recombinant light chain construct with the dileucine motif mutated to dialanine [rLC/A(LL-->AA)] also exhibits reduced activity ($EC_5$ rLC/A(LL-->AA) =184 pM); however, the effective concentration of the ΔN8ΔC22 construct is twenty-five fold greater than the rLC/A(LL-->AA) construct.

A modified light chain may include a light chain from *botulinum* toxins A, B, C1, D, E, F or G. One or multiple domains at the N— and/or C-terminus may be modified by addition, deletion or substitution. For example, a modified chimeric light chain component may include a light chain from BoNT/E modified by adding or replacing/substituting one or more N— and/or C-terminal end sequences derived from the BoNT/A light chain, thereby resulting in a chimeric BoNT/E-BoNT/A chimeric light chain with one or both terminal ends having one or more sequences which convey an increased or decreased ability to localize to a plasma membrane, increased or decreased biological persistence and/or an increased or decreased enzymatic activity.

A chimeric *botulinum* toxin can be constructed such that a C-terminal portion of the light chain of one *botulinum* toxin serotype replaces a similar C- terminal portion within the light chain of another *botulinum* toxin serotype. For example, the last twenty two amino acid residues bearing the dileucine motif from the C-terminus of the light chain of BoNT/A can replace the last twenty two amino acid residues of the C-terminus of the light chain of BoNT/E. The amino acid sequence of the entire light chain of such a chimeric construct is shown below:

MPKINSFNYNDPVNDRTILYIKPGGCQEFYKSFNIMK  SEQ ID NO:136

NIWIIPERNVIGTTPQDFHPPTSLKNGDSSYYDPNYL

QSDEEKDRFLKIVTKIFNRINNNLSGGILLEELSKAN

PYLGNDNTPDNQFHIGDASAVEIKFSNGSQDILLPNV

IIMGAEPDLFETNSSNISLRNNYMPSNHGFGSIAIVT

FSPEYSFRFNDNSMNEFIQDPALTLMHELIHSLHGLY

GAKGITTKYTITQKQNPLITNIRGTNIEEFLTFGGTD

LNIITSAQSNDIYTNLLADYKKIASKLSKVQVSNPLL

NPYKDVFEAKYGLDKDASGIYSVNINKFNDIFKKLYS

-continued
FTEFDLATKFQVKCRQTYIGQYKYFKLSNLLNDSIYN

ISEGYNINNLKVNFRGQNANLNPRIITPITGKNFTGL

FEFYKLLCVRGIITSK

In the construct above, the majority of the amino acid sequence is derived from BoNT/E serotype, and the amino acids shown in bold underlined text are derived from the last twenty two amino acid residues of the C-terminus of the light chain of BoNT/A which bears the dileucine motif.

In a further example, the first thirty amino acid residues from the N-terminus of the light chain of BoNT/A can replace the first thirty amino acid residues of the N-terminus of the light chain of BoNT/B. The amino acid sequence of the entire light chain of such a chimeric construct is shown below:

MPFVNKQFNYKDPVNGVDIAYIKIPNAGQMGRYYKAF  SEQ ID NO:137

KITDRIWIIPERYTFGYKPEDFNKSSGIFNRDVCEYY

DPDYLNTNDKKNIFFQTLIKLFNRIKSKPLGEKLLEM

IINGIPYLGDRRVPLEEFNTNIASVTVNKLISNPGEV

ERKKGIFANLIIFGPGPVLNENETIDIGIQNHFASRE

GFGGIMQMKFCPEYVSVFNNVQENKGASIFNRRGYFS

DPALILMHELIHVLHGLYGIKVDDLPIVPNEKKFFMQ

STDTIQAEELYTFGGQDPSIISPSTDKSIYDKVLQNF

RGIVDRLNKVLVCISDPNININIYKNKFKDKYKFVED

SEGKYSIDVESFNKLYKSLMLGFTEINIAENYKIKTR

ASYFSDSLPPVKIKNLLDNEIYTIEEGFNISDKNMGK

EYRGQNKAINKQAYEEISKEHLAVYKIQMCKSVK

In the construct above, the majority of the amino acid sequence is derived from BoNT/B serotype, and the amino acids shown in bold underlined text are derived from the first thirty amino acid residues of the N-terminus of the light chain of BoNT/A.

Still further, the chimeric construct can have both N-terminal and the C-terminal replacements. For example, the first nine amino acid residues from the N-terminus of the light chain of BoNT/A can replace the first nine amino acid residues of the N-terminus of the light chain of BoNT/E. Additionally, in the same construct, the last twenty-two amino acid residues from the C-terminus of the light chain of BoNT/A can replace the last twenty-two amino acid residues from the C-terminus of the light chain of BoNT/E. The amino acid sequence of the entire light chain of such a chimeric construct is shown below:

MPFVNKQFNNDPVNDRTILYIKPGGCQEFYKSFNIMK  SEQ ID NO:138

NIWIIPERNVIGTTPQDFHPPTSLKNGDSSYYDPNYL

QSDEEKDRFLKIVTKIFNRINNNLSGGILLEELSKAN

PYLGNDNTPDNQFHIGDASAVEIKFSNGSQDILLPNV

IIMGAEPDLFETNSSNISLRNNYMPSNHGFGSIAIVT

FSPEYSFRFNDNSMNEFIQDPALTLMHELIHSLHGLY

GAKGITTKYTITQKQNPLITNIRGTNIEEFLTFGGTD

-continued

LNIITSAQSNDIYTNLLADYKKIASKLSKVQVSNPLL

NPYKDVFEAKYGLDKDASGIYSVNINKFNDIFKKLYS

FTEFDLATKFQVKCRQTYIGQYKYFKLSNLLNDSIYN

ISEGYNINNLKVNFRGQNANLNPRIITPITGKNFTG

LFEFYKLLCVRGIITSK

In the construct above, the majority of the amino acid sequence is derived from BoNT/E serotype, and the amino acids shown in bold underlined text are derived from the first nine amino acid residues of the N-terminus and the last twenty-two amino acid residues of the C-terminus of the light chain of BoNT/A.

Similarly, the first nine amino acid residues from the N-terminus of the light chain of BoNT/A can replace the first nine amino acid residues of the N-terminus of the light chain of BoNT/B. Additionally, in the same construct, the last twenty-two amino acid residues from the C-terminus of the light chain of BoNT/A can replace the last twenty-two amino acid residues from the C-terminus of the light chain of BoNT/B. The amino acid sequence of the entire light chain of such a chimeric construct is shown below:

MPFVNKQFNYNDPIDNDNIIMMEPPFARGTGRYYKAF  SEQ ID NO:139

KITDRIWIIPERYTFGYKPEDFNKSSGIFNRDVCEYY

DPDYLNTNDKKNIFFQTLIKLFNRIKSKPLGEKLLEM

IINGIPYLGDRRVPLEEFNTNIASVTVNKLISNPGEV

ERKKGIFANLIIFGPGPVLNENETIDIGIQNHFASRE

GFGGIMQMKFCPEYVSVFNNVQENKGASIFNRRGYFS

DPALILMHELIHVLHGLYGIKVDDLPIVPNEKKFFMQ

STDTIQAEELYTFGGQDPSIISPSTDKSIYDKVLQNF

RGIVDRLNKVLVCISDPNINININIYKNKEKDKYKFVED

SEGKYSIDVESFNKLYKSLMLGFTEINIAENYKIKTR

ASYFSDSLPPVKIKNLLDNEIYTIEEGFNISDKNMGK

EYRGQNKAINKQKNFTGLFEFYKLLCVRGIITSK

In the construct above, the majority of the amino acid sequence is derived from BoNT/B serotype, and the amino acids shown in bold underlined text are derived from the first nine amino acid residues of the N-terminus and the last twenty-two amino acid residues of the C-terminus of the light chain of BoNT/A.

Furthermore, the first nine amino acid residues from the N-terminus of the light chain of BoNT/A can replace the first nine amino acid residues of the N-terminus of the light chain of BoNT/F. Additionally, in the same construct, the last twenty-two amino acid residues from the C-terminus of the light chain of BoNT/A can replace the last twenty-two amino acid residues from the C-terminus of the light chain of BoNT/F. The amino acid sequence of the entire light chain of such a chimeric construct is shown below:

MPFVNKQFNYNDPVNDDTILYMQIPYEEKSKKYYKAF  SEQ ID NO:140

EIMRNVWIIPERNTIGTNPSDFDPPASLKNGSSAYYD

-continued

PNYLTTDAEKDRYLKTTIKLFKRINSNPAGKVLLQEI

SYAKPYLGNDHTPIDEFSPVTRTTSVNIKLSTNVESS

MLLNLLVLGAGPDIFESCCYPVRKLIDPDVVYDPSNY

GFGSINIVTFSPEYEYTFNDISGGHNSSTESFIADPA

ISLAHELIHALHGLYGARGVTYEETIEVKQAPLMIAE

KPIRLEEFLTFGGQDLNIITSAMKEKIYNNLLANYEK

IATRLSEVNSAPPEYDINEYKDYFQWKYGLDKNADGS

YTVNENKFNEIYKKLYSFTESDLANKFKVKCRNTYFI

KYEFLKVPNLLDDDIYTVSEGFNIGNLAVNRGQSIKL

NPKIIDKNFTGLFEFVKLLCVRGIITSK

In the construct above, the majority of the amino acid sequence is derived from BoNT/F serotype, and the amino acids shown in bold underlined text are derived from the first nine amino acid residues of the N-terminus and the last twenty-two amino acid residues of the C-terminus of the light chain of BoNT/A.

In some embodiments, a light chain can be engineered such that one or more segments of the light chain of one or more toxin serotypes replace one or more segments of equal or unequal length within the light chain of another toxin serotype. In a non-limiting example of this kind of chimeric construct, fifty amino acid residues from the N-terminus of the light chain of BoNT/A can replace eight amino acid residues of the N-terminus of the light chain of BoNT/B, resulting in a net gain of forty-two amino acids in length in the N-terminal region of the light chain chimera. The amino acid sequence of the entire light chain of such a chimeric construct is shown below:

MPFVNKQFNYKDPVNGVDIAYIKIPNAGQMQPVKAFK  SEQ ID NO:141

IHNKIWVIPERDTFYNDPIDNDNIIMMEPPFARGTGR

YYKAFKITDRIWIIPERYTFGYKPEDFNKSSGIFNRD

VCEYYDPDYLNTNDKKNIFFQTLIKLFNRIKSKPLGE

KLLEMIINGIPYLGDRRVPLEEFNTNIASVTVNKLIS

NPGEVERKKGIFANLIIFGPGPVLNENETIDIGIQNH

FASREGFGGIMQMKFCPEYVSVFNNVQENKGASIFNR

RGYFSDPALILMHELIHVLHGLYGIKVDDLPIVPNEK

KFFMQSTDTIQAEELYTFGGQDPSIISPSTDKSIYDK

VLQNFRGIVDRLNKVLVCISDPNININIYKNFKDKYK

FVEDSEGKYSIDVESFNKLYKSLMLGFTEINIAENYK

IKTRASYFSDSLPPVKIKNLLDNEIYTIEEGFNISDK

NMGKEYRGQNKAINKQAYEEISKEHLAVYKIQMGKSV

K

In the construct above, the majority of the amino acid sequence is derived from BoNT/B serotype, and the amino acids shown in bold underlined text are derived from the first fifty amino acid residues of the N-terminus of the light chain of BoNT/A.

In a non-limiting example of this kind of chimeric construct, the last fifty amino acid residues from the C-terminus of the light chain of BoNT/A can replace fifteen amino acid residues within the C-terminus of the light chain of BoNT/E, resulting in a net gain of thirty-five amino acids in the C-terminal region of the light chain chimera. The amino acid sequence of the entire light chain of such a chimeric construct is shown below:

MPKINSFNYNDPVNDRTILYIKPGGCQEFYKSFNIMK SEQ ID NO:142
NIWIIPERNVIGTTPQDFHPPTSLKNGDSSYYDPNYL
QSDEEKDRFLKIVTKIFNRINNNLSGGILLEELSKAN
PYLGNDNTPDNQFHIGDASAVEIKFSNGSQDILLPNV
IIMGAEPDLFETNSSNLSLRNNYMPSNHGFGSIAIVT
FSPEYSFRFNDNSMNEFIQDPALTLMHELIHSLHGLY
GAKGITTKYTITQKQNPLITNIRGTNIEEFLTFGGTD
LNIITSAQSNDIYTNLLADYKKIASKLSKVQVSNPLL
NPYKDVFEAKYGLDKDASGIYSVNINKFNDIFKKLYS
FTEFDLATKFQVKCRQTYIGQYKYFKLSNLLNDSIYN
ISEGYNINNLKVNFRGQNANLNPRIITPGFNLRNTNL
AANFNGQNTEINNMNFTKLKNFTGLFEFYKLLCVRGI
ITSKNIVSVKGIRK

In the construct above, the majority of the amino acid sequence is derived from BoNT/E serotype, and the amino acids shown in bold underlined text are derived from the last fifty amino acid residues of the C-terminus of the light chain of BoNT/A.

In a non-limiting example of this kind of chimeric construct, thirty amino acid residues from the N-terminus of the light chain of BoNT/A can replace ten amino acid residues of the N-terminus of the light chain of BoNT/E, resulting in a net gain of twenty amino acids in length in the N-terminal region of the chimera. Additionally, in the same construct, the last fifty amino acid residues from the C-terminus of the light chain of BoNT/A can replace the last fifty amino acid residues from the C-terminus of the light chain of BoNT/E. The amino acid sequence of the entire light chain of such a chimeric construct is shown below:

MPKINSFNYMPFVNKQFNYKDPVNGVDIAYIKIPNAG SEQ ID NO:143
QMYIKPGGCQEFYKSFNIMKNIWIIPERNVIGTTPQD
FHPPTSLKNGDSSYYDPNYLQSDEEKDRFLKIVTKIF
NRINNNLSGGILLEELSKANPYLGNDNTPDNQFHIGD
ASAVEIKFSNGSQDILLPNVIIMGAEPDLFETNSSNI
SLRNNYMPSNHGFGSIAIVTFSPEYSFRFNDNSMNEF
IQDPALTLMHELIHSLHGLYGAKGITTKYTITQKQNP
LITNIRGTNIEEFLTFGGTDLNIITSAQSNDIYTNLL
ADYKKIASKLSKVQVSNPLLNPYKDVFEAKYGLDKDA
SGIYSVNINKFNDIFKKLYSFTEFDLATKFQVKCRQT
YIGQYKYFKLSNLLNDSIYNISEGFNLRNTNLAANFN
GQNTEINNMNFTKLKNFTGLFEFYKLLCVRGIITSK

In the construct above, the majority of the amino acid sequence is derived from BoNT/E serotype, and the amino acids shown in bold underlined text are derived from the thirty amino acid residues of the N-terminus and the last fifty amino acid residues of the C-terminus of the light chain of BoNT/A.

In a non-limiting example of this kind of chimeric construct, thirty amino acid residues from the N-terminus of the light chain of BoNT/A can replace ten amino acid residues of the N-terminus of the light chain of BoNT/B, resulting in a net gain of twenty amino acids in length in the N-terminal region of the chimera. Additionally, in the same construct, the last fifty amino acid residues from the C-terminus of the light chain of BoNT/A can replace the last fifty amino acid residues from the C-terminus of the light chain of BoNT/B. The amino acid sequence of the entire light chain of such a chimeric construct is shown below:

MPVTINNFNPMPFVNKQFNYKDPVNGVDIAYIKIPNAG SEQ ID NO:144
QMIMMEPPFARGTGRYYKAFKITDRIWIIPERYTFGY
KPEDFNKSSGIFNRDVCEYYDPDYLNTNDKKNIFFQT
LIKLFNRIKSKPLGEKLLEMIINGIPYLGDRRVPLEE
FNTNIASVTVNKLISNPGEVERKKGIFANLIIFGPGP
VLNENETIDIGIQNHFASREGFGGIMQMKFCPEYVSV
FNNVQENKGASIFNRRGYFSDPALILMHELIHVLHGL
YGIKVDDLPIVPNEKKFFMQSTDTIQAEELYTFGGQD
PSIISPSTDKSIYDKVLQNFRGIVDRLNKVLVCISDP
NININIYKNKFKDKYKFVEDSEGKYSIDVESFNKLYK
SLMLGFTEINIAENYKIKTRASYFSDSLPPVKIKNLL
DNEIGFNLRNTNLAANFNGQNTEINNMNFTKLKNFTG
LFEFYKLLCVRGIITSK

In the construct above, the majority of the amino acid sequence is derived from BoNT/B serotype, and the amino acids shown in bold underlined text are derived from the thirty amino acid residues of the N-terminus and the last fifty amino acid residues of the C-terminus of the light chain of BoNT/A.

In a non-limiting example of this kind of chimeric construct, thirty amino acid residues from the N-terminus of the light chain of BoNT/A can replace ten amino acid residues of the N-terminus of the light chain of BoNT/F, resulting in a net gain of twenty amino acids in length in the N-terminal region of the chimera. Additionally, in the same construct, the last fifty amino acid residues from the C-terminus of the light chain of BoNT/A can replace the last fifty amino acid residues from the C-terminus of the light chain of BoNT/F. The amino acid sequence of the entire light chain of such a chimeric construct is shown below:

MPVAINSFNMPFVNKQFNYKDPVNGVDIAYIKIPNAG SEQ ID NO:145
QMLYMQIPYEEKSKKYYKAFEIMRNVWIIPERNTIGT

```
                              -continued
NPSDFDPPASLKNGSSAYYDPNYLTTDAEKDRYLKTT

IKLFKRINSNPAGKVLLQEISYAKPYLGNDHTPIDEF

SPVTRTTSVNIKLSTNVESSMLLNLLVLGAGPDIFES

CCYPVRKLIDPDVVYDPSNYGFGSINIVTFSPEYEYT

FNDISGGHNSSTESFIADPAISLAHELIHALHGLYGA

RGVTYEETIEVKQAPLMIAEKPIRLEEFLTFGGQDLN

IITSAMKEKIYNNLLANYEKIATRLSEVNSAPPEYDI

NEYKDYFQWKYGLDKNADGSYTVNENKFNEIYKKLYS

FTESDLANKFKVKCRNTYFIKYEFLKVPNLLDDDIYG

FNLRNTNLAANFNGQNTEINNMNFTKLKNFTGLFEFY

KLLCVRGIITSK
```

In the construct above, the majority of the amino acid sequence is derived from BoNT/F serotype, and the amino acids shown in bold underlined text are derived from the thirty amino acid residues of the N-terminus and the last fifty amino acid residues of the C-terminus of the light chain of BoNT/A.

In some embodiments, the swapped sequences can be derived from two different sterotypes, resulting in a chimera with regions from three different serotypes in all. In this example, eight amino acid residues from the N-terminus of the light chain of BoNT/B can replace five amino acid residues of the N-terminus of the light chain of BoNT/E, resulting in a net gain of three amino acids in length in the N-terminal region of the chimera. Additionally, in the same construct, 30 amino acid residues including the dileucine repeat of the C-terminus of the light chain of BoNT/A can replace ten amino acid residues within the C-terminus of the light chain of BoNT/E, resulting in a net gain of 20 amino acids in the C-terminal region of the chimera. The amino acid sequence of the entire light chain of such a chimeric construct is shown below:

```
MPKINSFNYNDP *VTINNFNY*DRTILYIKPGGCQEFYK     SEQ ID NO:146

SFNIMKNIWIIPERNVIGTTPQDFHPPTSLKNGDSSY

YDPNYLQSDEEKDRFLKIVTKIFNRINNNLSGGILLE

ELSKANPYLGNDNTPDNQFHIGDASAVEIKFSNGSQD

ILLPNVIIMGAEPDLFETNSSNISLRNNYMPSNHGFG

SIAIVTFSPEYSFRFNDNSMNEFIQDPALTLMHELIH

SLHGLYGAKGITTKYTITQKQNPLITNIRGTNIEEFL

TFGGTDLNIITSAQSNDIYTNLLADYKKIASKLSKVQ

VSNPLLNPYKDVFEAKYGLDKDASGIYSVNINKFNDI

FKKLYSFTEFDLATKFQVKCRQTYIGQYKYFKLSNLL

NDSIYNISEGYNINNLKVNFRGQNANLNPRIITPITG

RGLVKKIIRFCKNNMNFTKLKNFTGLFEFYKLLCVRG

IITSK
```

In the construct above, the majority of the amino acid sequence is derived from BoNT/E serotype, and the amino acids shown in bold italicized text are derived from eight amino acid residues of the N-terminus of the light chain of BoNT/B and thirty amino acid residues shown in bold underlined text are derived from thirty amino acid residues of the C-terminus of the light chain of BoNT/A.

In a non-limiting example, eight amino acid residues from the N-terminus of the light chain of BoNT/B can replace five amino acid residues of the N-terminus of the light chain of BoNT/F, resulting in a net gain of three amino acids in length in the N-terminal region of the chimera. Additionally, in the same construct, 30 amino acid residues including the dileucine repeat of the C-terminus of the light chain of BoNT/A can replace ten amino acid residues within the C-terminus of the light chain of BoNT/F, resulting in a net gain of 20 amino acids in the C-terminal region of the chimera. The amino acid sequence of the entire light chain of such a chimeric construct is shown below:

```
MPVAINSFNYND *VTINNFNY*TILYMQIPYEEKSKKYY    SEQ ID NO:147

KAFEIMRNVWIIPERNTIGTNPSDFDPPASLKNGSSA

YYDPNYLTTDAEKDRYLKTTIKLFKRINSNPAGKVLL

QEISYAKPYLGNDHTPIDEFSPVTRTTSVNIKLSTNV

ESSMLLNLLVLGAGPDIFESCCYPVRKLIDPDVVYDP

SNYGFGSINIVTFSPEYEYTFNDISGGHNSSTESFIA

DPAISLAHELIHALHGLYGARGVTYEETIEVKQAPLM

IAEKPIRLEEFLTFGGQDLNIITSAMKEKIYNNLLAN

YEKIATRLSEVNSAPPEYDINEYKDYFQWKYGLDKNA

DGSYTVNENKFNEIYKKLYSFTESDLANKFKVKCRNT

YFIKYEFLKVPNLLDDDIYTVSEGFNIGNLAVNNRGQ

SIKLNPKIIDSIPDKGLVEKNNMNFTKLKNFTGLFEF

YKLLCVRGIITSKRK
```

In the construct above, the majority of the amino acid sequence is derived from BoNT/F serotype, and the amino acids shown in bold italicized text are derived from eight amino acid residues of the N-terminus of the light chain of BoNT/B and thirty amino acid residues shown in bold underlined text are derived from thirty amino acid residues of the C-terminus of the light chain of BoNT/A.

Example 16D

The invention also provides for a light chain of a *botulinum* toxin B, C1, D, E, F or G comprising about the first 30 amino acids from the N-terminus of the light chain of *botulinum* toxin type A and about the last 50 amino acids from the C-terminus of the light chain of *botulinum* toxin type A. The first 30 amino acids of the N-terminus of type A here may be all or part, for example 2-16 contiguous or non contiguous amino acids, of the 30 amino acids. The last 50 amino acids here may be all or part, for example 5-43 contiguous or non-contiguous, amino acids of the 50 amino acids.

In some embodiments, such a light chain comprises about the first 20 amino acids from the N-terminus of the light chain of *botulinum* toxin type A and about the last 30 amino acids from the C-terminus of the light chain of *botulinum* toxin type A. The first 20 amino acids of the N-terminus of type A here may be all or part, for example 2-16 contiguous or non contiguous amino acids, of the 20 amino acids. The last 30 amino acids here may be all or part, for example 5-23 contiguous or non-contiguous, amino acids of the 30 amino acids.

In some embodiments, such a light chain comprises about the first 4 to 8, e.g. the first 8, amino acids from the N-terminus of the light chain of *botulinum* toxin type A and about the last 7 to 22, e.g. the last 22, amino acids from the C-terminus of the light chain of *botulinum* toxin type A. The first 8 amino acids of the N-terminus of type A here may be all or part, for example 2-7 contiguous or non contiguous amino acids, of the 7 amino acids. The last 22 amino acids here may be all or part, for example 5-16 contiguous or non-contiguous, amino acids of the 20 amino acids.

In some embodiments, the inclusion of about the first 30 amino acids from the N-terminus and about the last 50 amino acids from the C-terminus of the light chain of type A replaces one or more amino acids at the N- and C-termini, respectively, of the light chain of *botulinum* toxin type B, C1, D, E, F or G. The first 30 amino acids of the N-terminus of type A here may be all or part, for example 2-16 contiguous or non contiguous amino acids, of the 30 amino acids. The last 50 amino acids here may be all or part, for example 5-43 contiguous or non-contiguous, amino acids of the 50 amino acids.

In some embodiments, the inclusion of about the 20 amino acids from the N-terminus and about the 30 amino acids from the C-terminus of the light chain of type A replaces one or more amino acids at the N- and C-termini, respectively, of the light chain of *botulinum* toxin type B, C1, D, E, F or G. The first 20 amino acids of the N-terminus of type A here may be all or part, for example 2-16 contiguous or non contiguous amino acids, of the 20 amino acids. The last 30 amino acids here may be all or part, for example 5-23 contiguous or non-contiguous, amino acids of the 30 amino acids.

In some embodiments, the inclusion of about the first 4 to 8, for example the first 8, amino acids from the N-terminus and about the last 7 to 22, for example the last 22, amino acids from the C-terminus of the light chain of type A replaces one or more amino acids at the N— and C-termini, respectively, of the light chain of *botulinum* toxin type B, C1, D, E, F or G. The first 8 amino acids of the N-terminus of type A here may be all or part, for example 2-7 contiguous or non contiguous amino acids, of the 7 amino acids. The last 22 amino acids here may be all or part, for example 5-16 contiguous or non-contiguous, amino acids of the 20 amino acids.

The invention also provides for a modified *botulinum* toxin comprising the light chain of described herein, including the ones described in Example 16D.

Example 17

Intracellular Localization of *Botulinum* Toxin Types A, B and E Light Chains in Neuronal and Non-Neuronal Cells:

Clostridial neurotoxins inhibit neurotransmission by cleavage of a SNARE protein; each serotype has a distinct therapeutic profile regarding efficacy, safety, and duration of action (BoNT/A>BoNT/B>>BoNT/E). After the toxin is internalised, the catalytic light chain (LC) translocates into the cytosol and cleaves one of the SNARE proteins. Differences in subcellular localization may influence the pharmacology of different serotypes. Constructs were generated encoding the LC from serotypes A, B and E fused with green fluorescent protein (GFP) at N— or C-terminus and transfected them into PC12 cells that were differentiated after transfection. Expression and catalytic activity of LC's were assessed by western blotting. Confocal microscopy reveals that GFP-LCA and LCA-GFP-GFP are localized in a punctate pattern on the plasma membrane and neurites, (very similar to the localization of GFP-SNAP-25). GFP-LCE and LCE-GFP-GFP are dispersed in the cytoplasm but their localization is markedly different from that of GFP alone. GFP-LCB is also cytosolic but different from GFP-LCE, while LCB-GFP-GFP is located in an internal structure. Localization data demonstrated that LCB-GFP-GFP is accumulated intracellularly (i.e. "localized" to the cytosol) and Western blot analysis demonstrated that this protein construct is being degraded in PC12 cells.

Thus, the LCB-GFP-GFP was noted to be in an extremely bright and presumably high concentration of LCB-GFP-GFP in a tight area and it was not cytosolic (was not diffuse throughout the cytosol). It may be that the LCB-GFP-GFP was, for example, retained in the ER (as is the case for some misfolded proteins), in a protein degradation path/organelle, or in an aggregation and precipitation within the cell (i.e. in an aggresome).

The inventors have shown that this pattern of localization is not unique to neuronal cells. Two non-neuronal cell lines: HeLa (adenocarcinoma of cervix) and HEK293T (human embryonic kidney) were transfected with the above described constructs. The various GFP-LC constructs expressed in HeLa cells displayed very similar patterns of localization for all serotypes, compared to those expressed in PC12 cells. Expression of the GFP-LC constructs in HEK293T cells resulted in a mixed patterns of localization with several constructs having similarities to LCB-GFP. Western blot analysis of the expressed proteins demonstrated that all the LC's were being degraded in HEK293T cells.

Materials and Methods:

The Light Chain genes from BoNT/A (Allergan Hall A), BoNT/B (NCTC 7273 Beans) and BoNT/E (NCTC 11219) were amplified from genomic DNA by PCR. The genes were cloned into pQBI25 plasmids (Qbiogene) as fusion proteins with GFP at the N-terminus or separately at the C-terminus:

GFP-LCA (GLCA), LCA-GFP; GFP-LCB (GLCB), LCB-GFP (LCBG); GFP-LCE (GLCE), LCE-GFP (LCEG)

The cell lines used for transfection were:

PC12: rat pheochromocytoma (chromaffin cells). NGF induces properties of sympathetic neurons.

HeLa cells: adenocarcinoma of cervix. Epithelial, non-secretory, no SNAP25, no VAMP-2.

HEK293T cells: primary human embryonal kidney transformed with SV40. No SNAP25, no VAMP-2 expression Cell lines were transfected using Lipofectamine2000 (Invitrogen). PC 12 cells were transfected under undifferentiated conditions and were differentiated afterwards with NGF (Harlan). Plasmids expressing GFP alone were used as a control in all experiments.

Expression and integrity of the transfected GFP-Light Chain fusions was assessed by immunoprecipitation using a GFP monoclonal antibody (3E6, Qbiogene), followed by western blot with antibodies probing for GFP (PolyAb, Santa Cruz) or LCA (PolyAb generated at Allergan).

Catalytic activity of the expressed Light Chain fusion proteins was determined by western blot using the following antibodies:

SMI-81 (Stemberger) and N-19 (Santa Cruz): Recognize cleaved (BoNT/A and BoNT/E) and full length SNAP 25.

PolyAb SNAP25$_{197}$: Polyclonal antibody generated at Allergan, specific to the BoNT/A cleaved peptide.

PolyAb SNAP25$_{180}$: Polyclonal antibody generated at Allergan, specific to the BoNT/E cleaved peptide.

Localization of the Light Chains was determined by confocal microscopy (Leica). Cell slices were taken at several positions in the transfected cells. Slices with the focal point at the middle of the cell are shown.

Inhibition of exocytosis as a result of expressing GFP-LCs was assessed by quantitation of $^3$H-noradrenaline release induced by K$^+$/Ca$^{2+}$ stimulation.

Cells were loaded for 4 hours with $^3$H-noradrenaline at 0.042 mM in culture media, and then washed 3× with PBS. Exocytosis was induced with K$^+$ in a Ca$^{2+}$ containing buffer.

Figure 19:
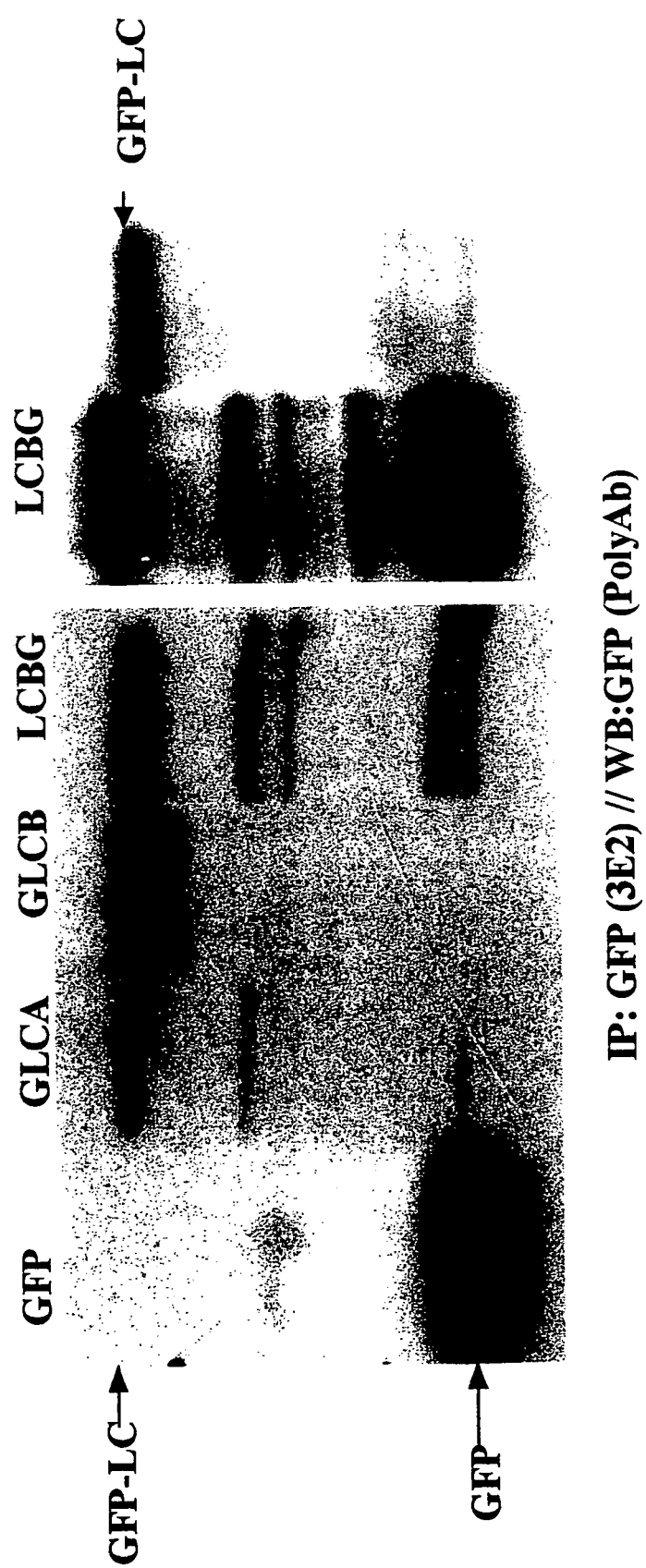
FIG. 19 shows the expression of transfected light chains in differentiated PC12 cells.
Figure 20:
FIG. 20 shows activity assessed by western blot of the lysate of transfected cells.

FIGS. 19 and 20 show the expression and activity of light chains in differentiated PC12 cells.

FIG. 19 shows the detection of GFP-LC fusion proteins expressed in differentiated PC12 cells. LCB-GFP is degraded in PC12 cells but not GFP-LCB. Expression and integrity of GFP-LCA was also assessed by probing with polyclonal antibody to LCA.

FIG. 20 shows Western blots of lysates from cells transfected with GFP, GFP-LCA, GFP-LCE, and GFP+LCA (each gene transfected separately, not a fusion construct). Activity of the light chains was assessed by probing with specific antibodies for the LCA and LCE cleaved products of SNAP25, and to the N-terminus of SNAP25 (recognizes both the cleaved and full-length SNAP25). The data shows that the expressed light chains are active proteases. Antibodies to SNAP-25$_{197}$ and SNAP-25$_{180}$ were produced at Allergan.

Subcellular localization of light chains in PC12 cells is shown in FIGS. 21 to 23.

FIG. 21 shows that GFP-fused light chain A localizes to the plasma membrane. PC12 cells were transfected with plasmids encoding GFP and full length GFP-LCA. Images were taken in a confocal microscope, with the focal plane at the middle of the cell. A clear localization at the plasma membrane can be observed. LCA-GFP displayed the same plasma membrane localization pattern.

FIG. 22 shows that light chain B localizes in the cytoplasm. PC12 cells were transfected with plasmids encoding LCB-GFP and GFP-LCB. A different localization pattern was observed dependent on fusion of GFP to the N— or C-terminus of LCB. The localization pattern observed for LCB-GFP is likely due to degradation of the protein. GFP-LCB localizes to the cytoplasm.

FIG. 23 shows that Light Chain E also localizes primarily in the cytoplasm. PC12 cells expressing GFP-fusions of LCE do not extend neurites even in the presence of NGF. PC 12 cells were transfected with plasmids encoding GFP-LCE and LCE-GFP. The localization of LCE is cytoplasmic for both fusion proteins. Despite treatment with NGF, transfected cells were round, with very few neurites.

Figures 24A, 24B:
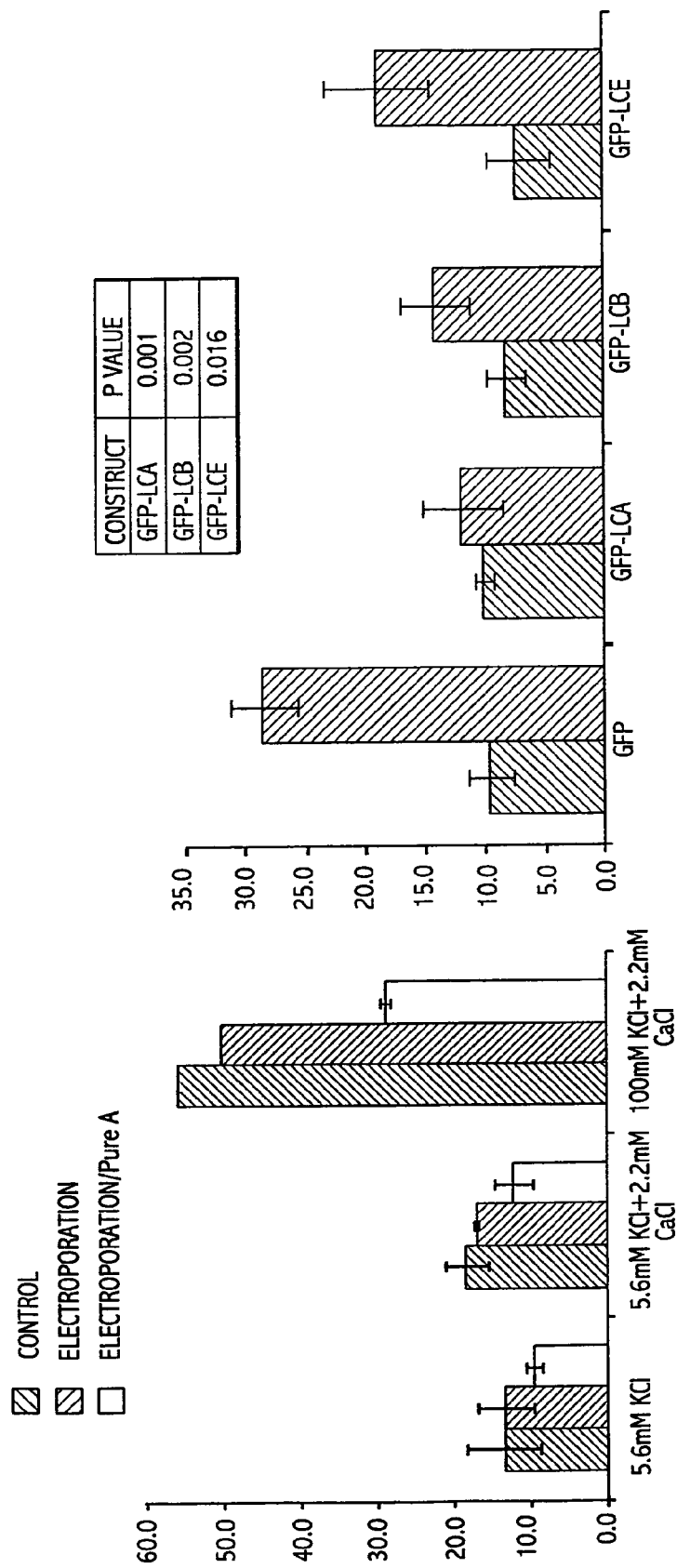
FIG. 24 shows that expressed LCs inhibit exocytosis.

FIG. 24 shows that expressed LCs inhibit exocytosis in PC12 cells. Exocytosis was measured in undifferentiated PC12 cells expressing GFP, GFP-LCA, GFP-LCB, and GFP-LCE that were selected for 3 days with G418. Release of $^3$H-noradrenaline was induced by incubating the cells with 100 mM K$^+$ in the presence of Ca$^{2+}$. Inhibition of exocytosis was observed in cells expressing the light chains. FIG. 24A shows norepinephrine release by PC12 cells electroporated with PURE A. The Y-axis represents % norepinephrine release. FIG. 24B shows the percentage of $^3$H norepinephrine released by non-differentiated PC12 cells transfected with various GFP constructs. The Y-axis represents % norepinephrine release.

FIG. 25 shows localization of GFP in HeLa and HEK293T cells. HeLa and HEK293T cells were transfected with a plasmid encoding the Green Fluorescent Protein (GFP). GFP fluorescence can be detected throughout the entire cell, including the nuclei (middle of cell).

Figure 26:
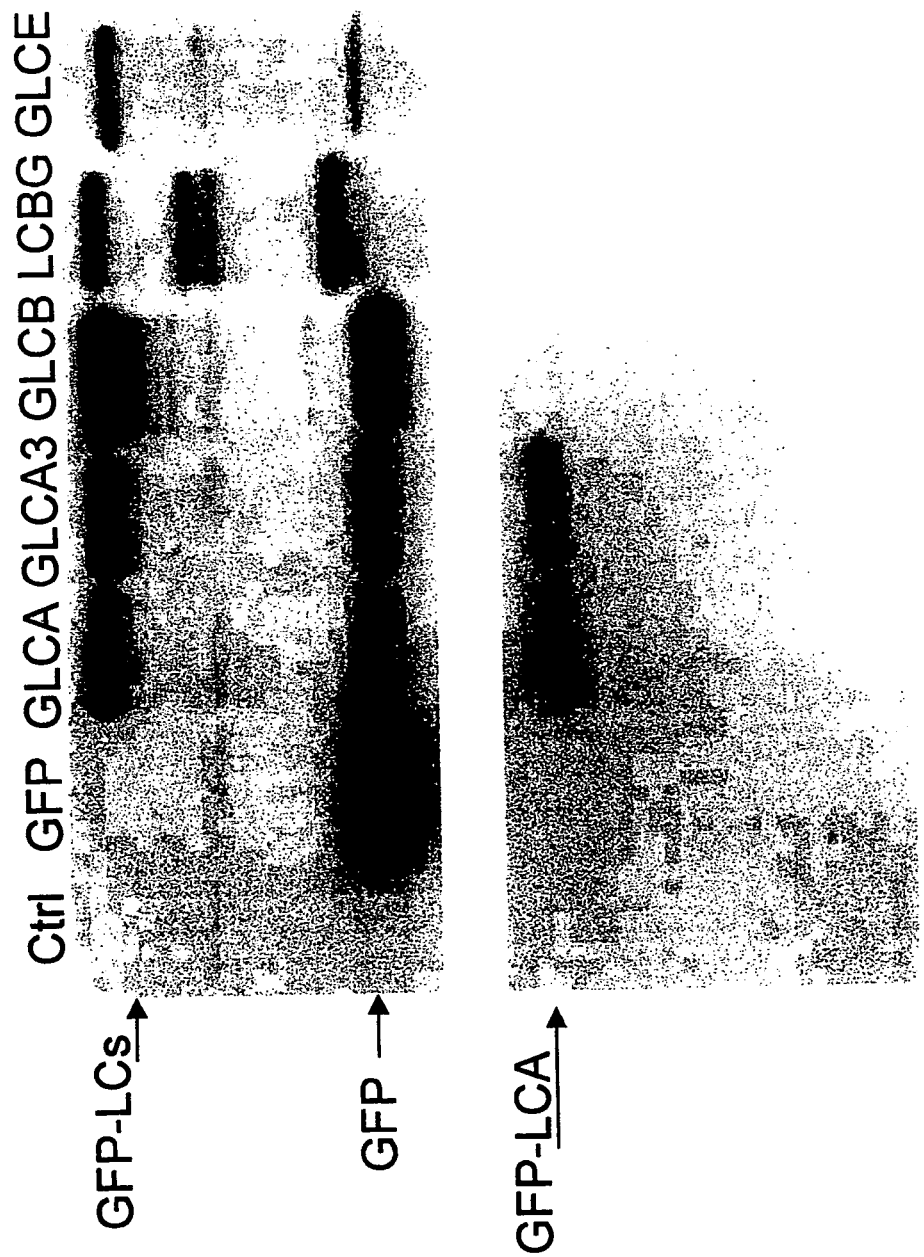
FIG. 26 shows detection of GFP-LC fusion proteins expressed in HeLa cells.
Figure 27:
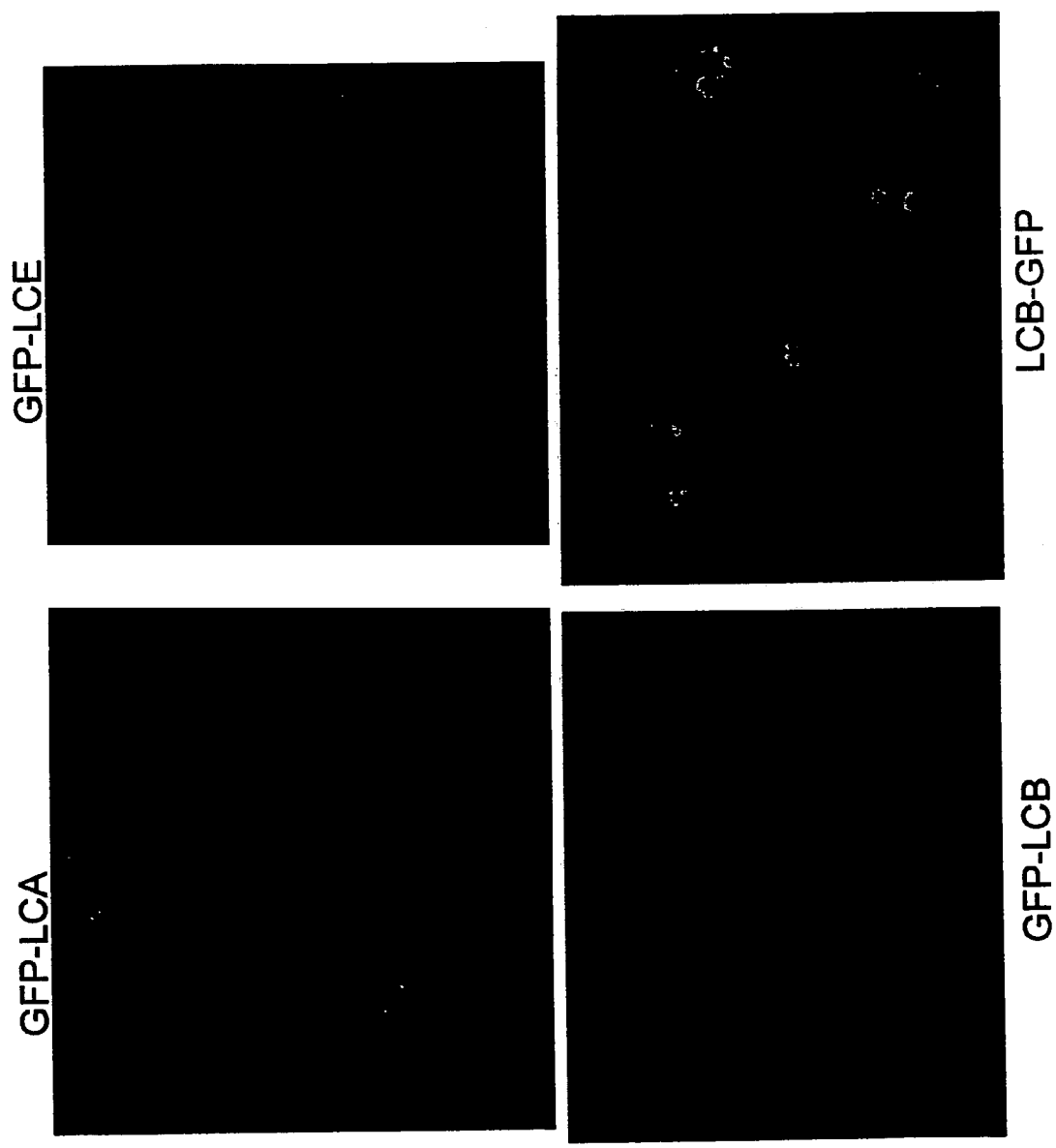
FIG. 27 shows localization of Light Chains in HeLa is similar to PC12 Cells. The panel on the left shows that GFP-*botulinum* toxin A light chain localizes to the plasma membrane. The middle panel shows that GFP-*botulinum* toxin B light chain exhibits a diffuse cytoplasmic localization. The panel on the right shows that GFP-*botulinum* toxin E light chain exhibits a semi-diffuse cytoplasmic localization.

FIGS. 26 and 27 show subcellular localization of GFP light chain fusions in HeLa cells.

FIG. 26 shows detection of GFP-LC fusion proteins expressed in HeLa cells, by probing Western blots with an antibody for GFP. This was accomplished by immunoprecipitation with a monoclonal antibody against GFP, followed with Western blot analysis probing for GFP with a polyclonal antibody In this cell line, LCB-GFP but not GFP-LCB is degraded, similar to PC12 cells. Expression and integrity of GFP-LCA was also assessed by probing with a polyclonal antibody to LCA. [Top: IP GFP(3E2)/WB GFP (PolyAb); Bottom: IP GFP(3E2)/WB LCA (PolyAb)].

FIG. 27 shows that localization of GFP-fused Light Chains expressed in HeLa cells is similar to PC12 Cells. HeLa cells were transfected with plasmids encoding GFP-LCA, GFP-LCE, GFP-LCB, and LCB-GFP. The pattern of localization for all Light Chains is similar to that observed in PC12 cells. Confocal images were acquired with the focal plane at the middle of the cells.

Figure 28:
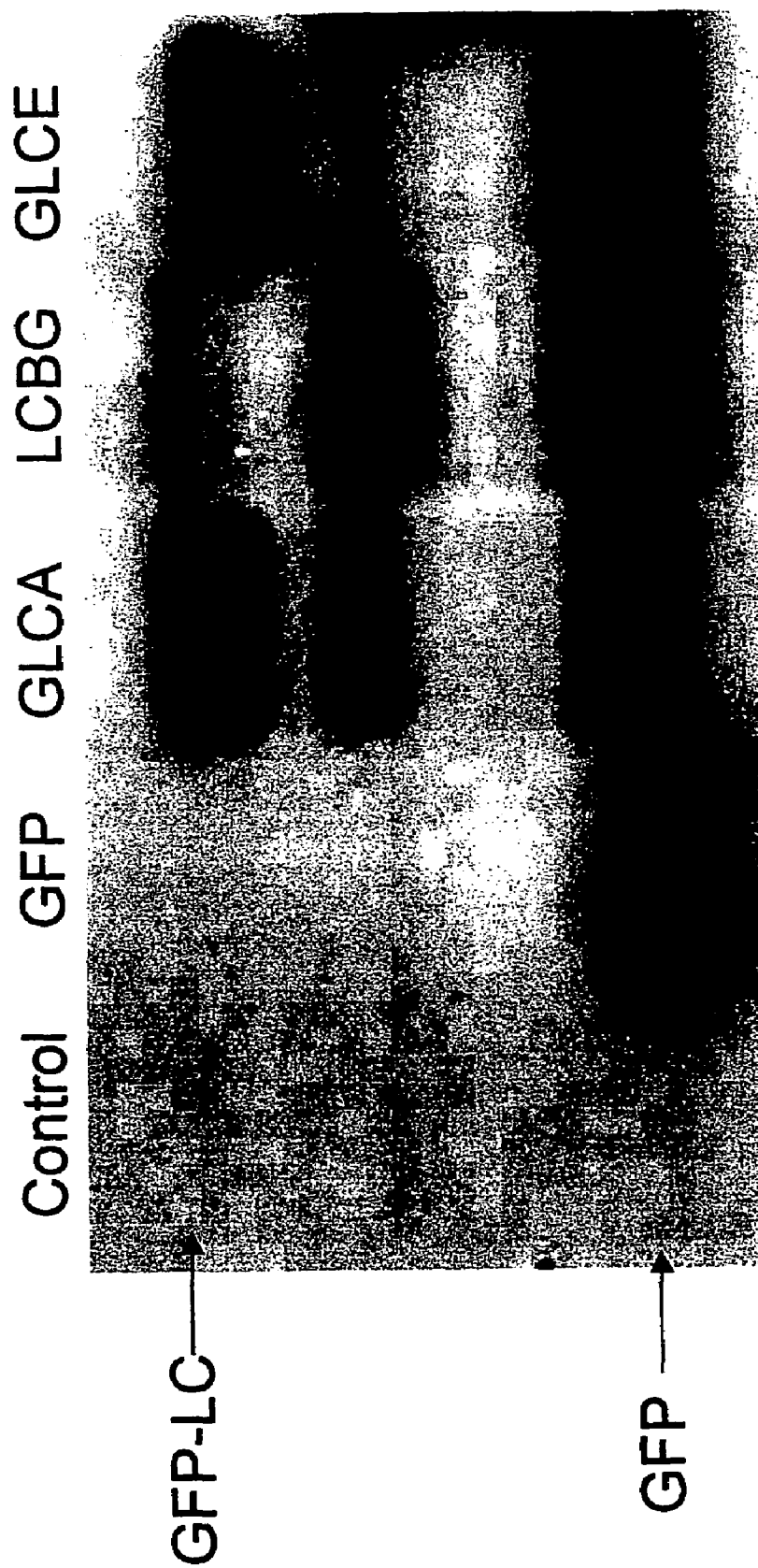
FIG. 28 shows the detection of GFP-LC fusion proteins expressed in HEK 293T cells.
Figure 29:
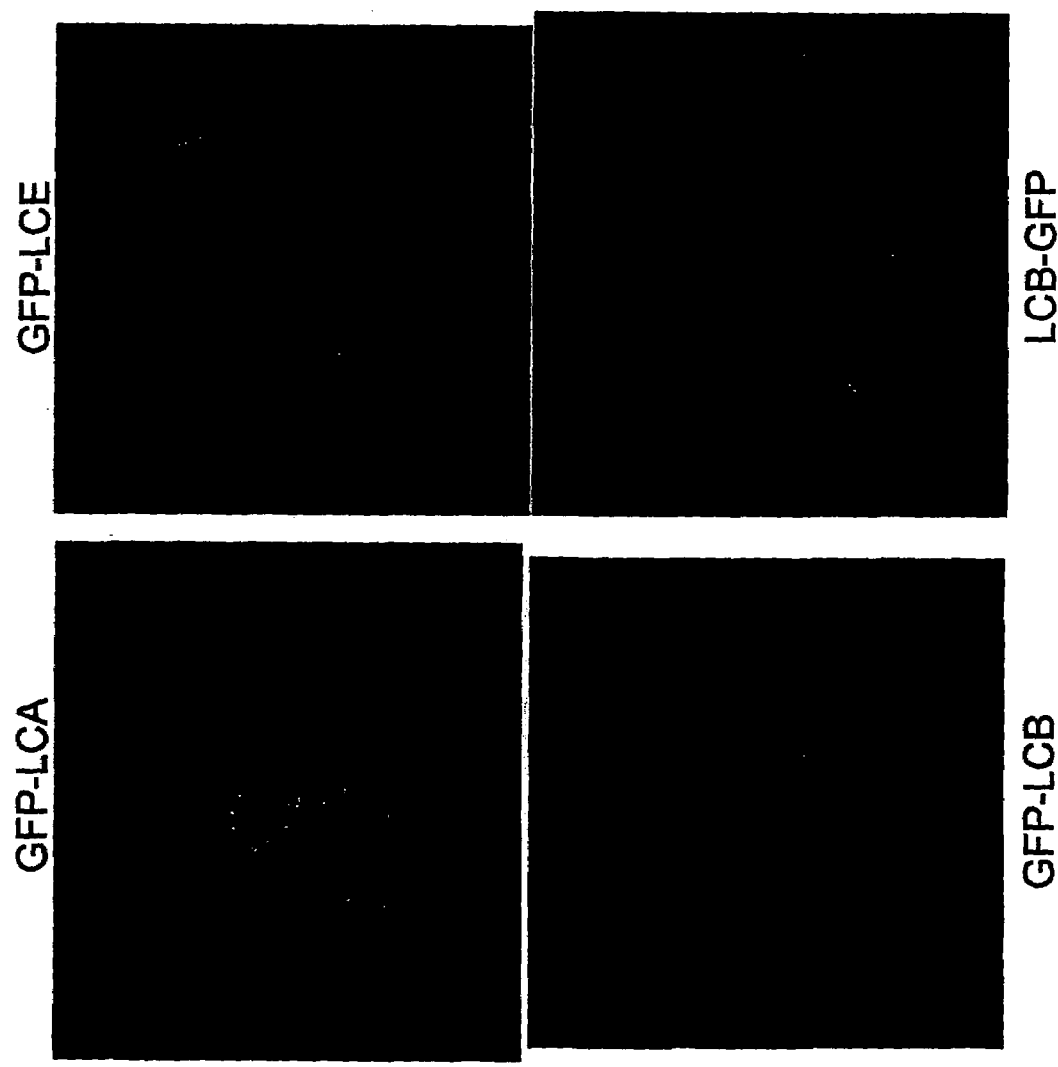
FIG. 29 shows HEK293T cells transfected with plasmids encoding GFP-LCA, GFP-LCE, GFP-LCB, and LCB-GFP. The panel on the left shows that GFP-*botulinum* toxin A light chain localizes to the plasma membrane. The middle panel shows that GFP-*botulinum* toxin B light chain exhibits a diffuse cytoplasmic localization. The panel on the right shows that GFP-*botulinum* toxin E light chain exhibits a semi-diffuse cytoplasmic localization.
Figure 30:
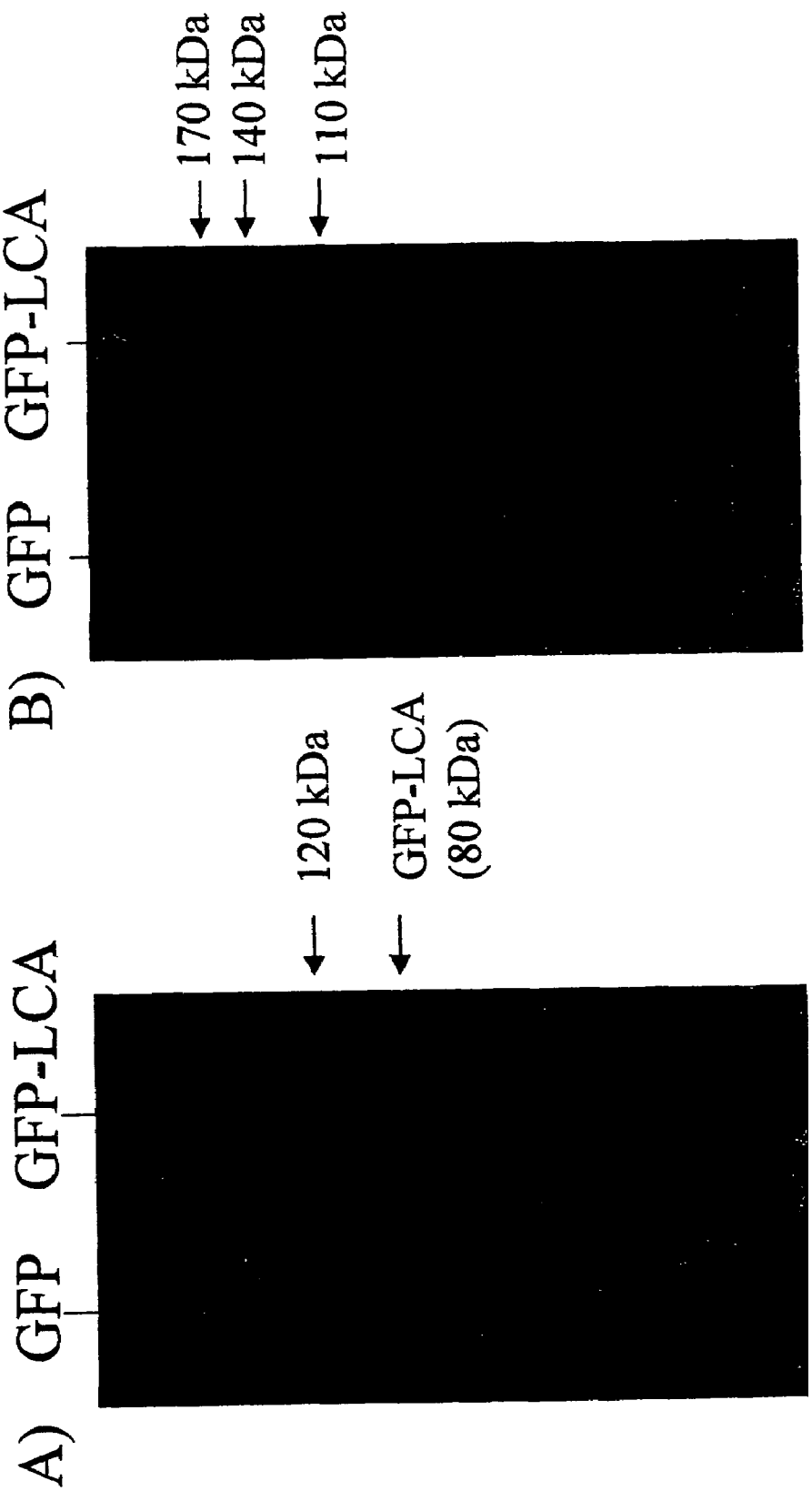
FIG. 30 shows western blots probed with a polyclonal antibody to LCA to determine the size of the complex containing GFP-LCA. PC-12 cells were treated with DPBT prior to lysis and the samples were immunoprecipitated using a monoclonal antibody for GFP. The western blot of the samples separated under reducing conditions shows a 80 kDa protein corresponding to GFP-LCA (FIG. 30A).
Figure 31:
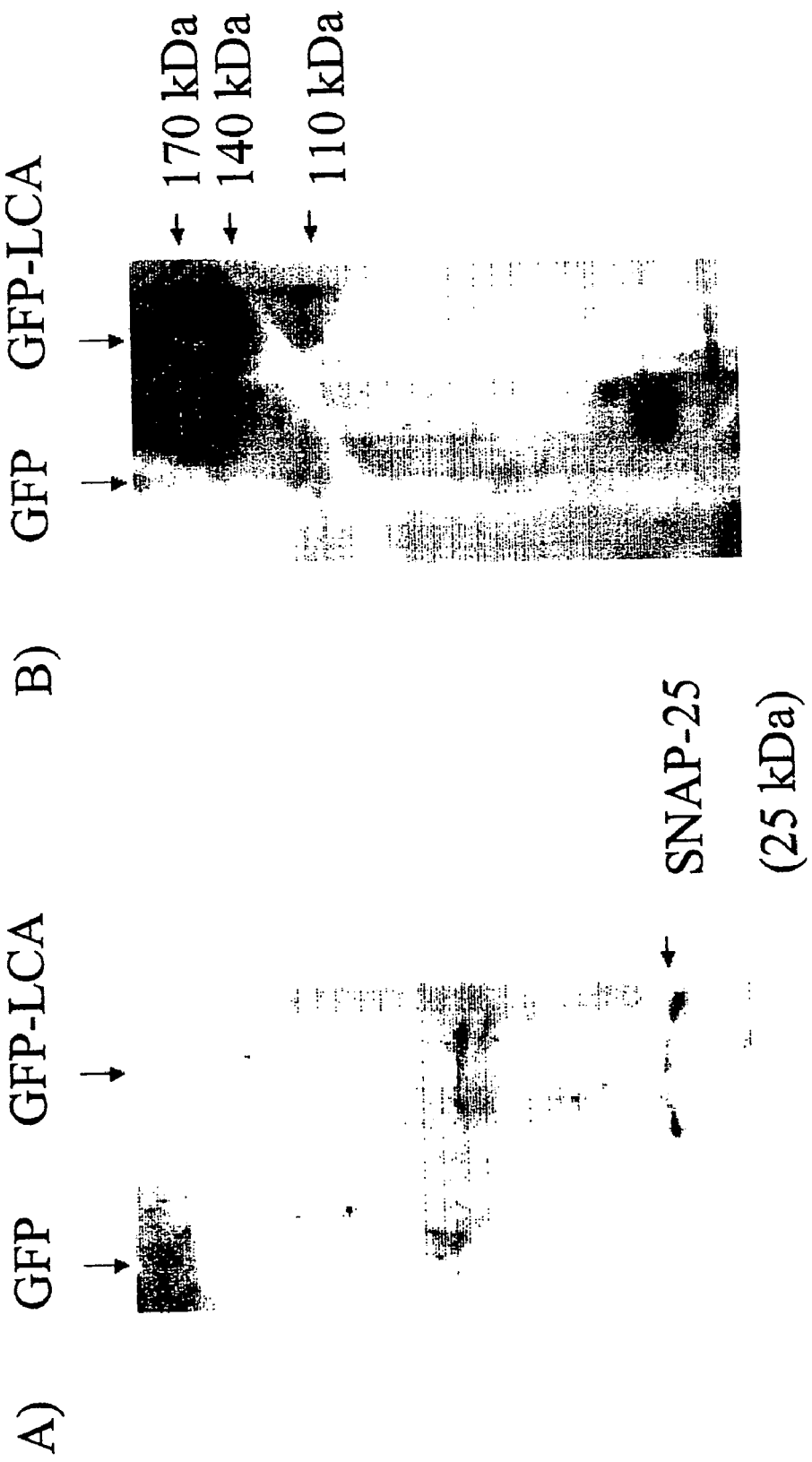
FIG. 31 shows western Blots probed with a polyclonal antibody to SNAP-25 to determine if the immuno-precipitated protein complexes containing GFP-LCA (FIG. 30) also contain SNAP-25.
Figure 32:
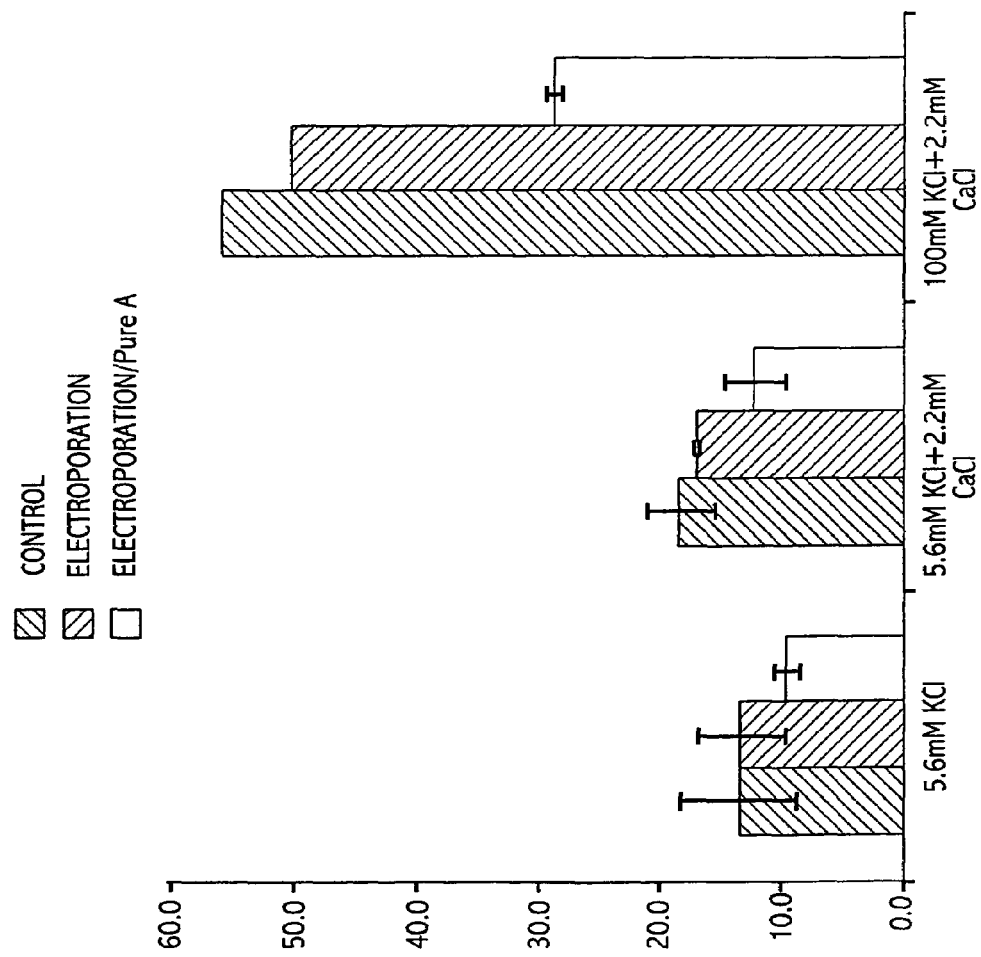
FIG. 32 is a graph showing the % of norepinephrine released from PC-12 cells when placed in buffers containing various concentrations of $Ca^{2+}/K^+$. The cells were untreated (control), electroporated, or electroporated in the presence of 500 nM PURE-A (electroporation/Pure A). Norepinephrine secretion was lower in PC-12 cells electroporated with 500 nM PURE-A. These results indicate an inhibition of PC-12 exocytosis caused by BoNT-A can be detected. The Y-axis shows the % of norepinephrine released.

FIGS. 28 and 29 show subcellular localization of GFP light chain fusions in HEK293T cells.

FIG. 28 shows the detection of GFP-LC fusion proteins expressed in HEK 293T cells. The fusion proteins were immunoprecipitated with a monoclonal antibody for GFP and the Western blots were probed with a polyclonal antibody for GFP. IP: GFP(3E2)/WB: GFP (PolyAb) The Western blot analysis revealed that all GFP-LC fusion proteins are being degraded in HEK293T cells.

FIG. 29 shows localization of the GFP fusion proteins in HEK293T cells transfected with plasmids encoding GFP-LCA, GFP-LCE, GFP-LCB, and LCB-GFP. The pattern of localization for all Light Chains is mixed with some resemblance to PC12 and HeLa cells but with accumulation of fluorescence intracellularly. The GFP-LC fusion proteins seem to accumulate similarly in all cell types when it is degraded. Western blots revealed that that all GFP-LC fusion proteins are degraded in HEK293T cells. Accumulation of the fusion proteins within the cells appears to be indicative of protein degradation.

The data shown in FIG. 19-29 demonstrates at least that:

the Light Chain of BoNT serotypes A, B and E displays a different subcellular localization;

GFP-LCA, GFP-LCB, and GFP-LCE fusion proteins expressed in differentiated PC12 cells display protease activity and inhibit exocytosis;

LCA localizes near the plasma membrane of PC12 and HeLa cells. Localization in HEK293T cells is different, probably due to degradation;

LCE localizes to the cytoplasm in PC12 and HeLa cells;

LCB-GFP is degraded in all cell types;

GFP-LCB has a cytoplasmic localization; and localization of the Light Chains is similar in both neuronal and non-neuronal exocytic cells (PC12 and HeLa cells, respectively), suggesting that the signal(s) for subcellular localization are contained within the Light Chain sequences.

Localization of the light chains from different serotypes of *botulinum* toxin may play a role in the therapeutic profile and duration of action of the neurotoxins.

Example 18

*Botulinum* Toxin Light Chain Constructs and Light Chain-Intracellular Structure Compositions:

Recombinant plasmids have been constructed to yield fusion proteins containing the green fluorescent protein attached to the light chain of *botulinum* neurotoxin (BoNT). These constructs are designated GFP-LCA, GFP-LCB, and GFP-LCE depending on the serotype of the constituent light chain. These light chains are metalloproteases that cleave a specific protein of the SNARE complex in neuronal cells inhibiting neurotransmitter release. Specifically, LCA and LCE cleave SNAP-25 and LCB cleaves VAMP2.

The inventors have shown that the protein product GFP-LCA localizes to the cytoplasmic side of the plasma membrane when expressed in PC-12 cells. The basis for membrane localization and identification of the compartment within the plasma membrane where the LCA resides was completed by identifying the proteins interacting with or in close proximity to GFP-LCA.

The inventors have also determined that the proteins expressed from the GFP-light chain constructs are active proteases with the ability to cleave specific SNARE proteins. The inventors also have demonstrated that these fusion proteins can inhibit exocytosis when expressed in secretory cell lines containing SNAP-25 and VAMP-2.

Methods:
Crosslinking Studies:
PC-12 cells were transfected with the plasmid containing either GFP–LCA (experimental group) or GFP (control group) and differentiated with neuronal growth factor (NGF). The cells were treated with a primary amine reactive crosslinking agent and subsequently lysed using T-X-100. The protein crosslinking agent, DTBP, is a reducible 11.9 Å chain, which can be cleaved by strong reducing agents such as DTT. DTBP is also water-soluble and membrane permeable.

The GFP-LCA was immunoprecipitated using a monoclonal antibody to GFP. The goal was to precipitate the GFP-LCA along with any interacting proteins attached via the cross-linking reagent. (This method can be used to prepare an isolated composition made up of a *botulinum* toxin light chain component and an intracellular structure component [the interacting proteins]. It is believed that the intracellular structure component interacts with the light chain component in a manner effective to facilitate substrate (SNARE) proteolysis within a cell.) These samples were subjected to SDS-PAGE under reduced and non-reduced conditions and blotted to PVDF. The blots were subsequently probed with antibodies specific for LCA and the SNARE protein SNAP-25. The antibodies used to probe are listed in the table below.

| Antibody Target | Source | Type (polyclonal or monoclonal) |
|---|---|---|
| LCA | Allergan | Polyclonal |
| SNAP-25(recognizes cleaved and uncleaved) | AB-CAM | Polyclonal |

Results:

Crosslinking Studies:

SNAP-25 immuno-precipitates with GFP-LCA suggesting these proteins form a complex when GFP-LCA is expressed in PC-12 cells. The inventors have also found that other SNARE type proteins immuno-precipitate with this complex when the cells are treated with a protein cross-linking agent prior to lysis. The inventors show the total size of the complex containing GFP-LCA and SNAP-25 using the cross-linking reagent.

FIG. 30 shows a western blot of GFP immuno-precipitated from cells transfected with GFP (lane 1) or GFP-LCA (lane 2). The cells were treated with a crosslinking agent DTBP prior to lysis. The samples were subjected to SDS-PAGE (4-15% polyacrilamide), blotted onto a PVDF membrane, and probed with an antibody for LCA. The samples are analyzed under reduced (FIG. 30A) and non-reduced (FIG. 30B) conditions. The crosslinking agent used in this study remains uncleaved in the non-reduced conditions. FIG. 30A shows that an 80 kDa protein is immuno-precipitated from PC-12 cells transfected with GFP-LCA, which correlates with the size of GFP-LCA. FIG. 30B shows three different protein complexes containing GFP-LCA are detected in the non-reduced sample with sizes of 110, 140 and 170 kDa. There were no protein bands larger than 170 kDa and nothing was detected in the wells of the gel. This result indicates sizes of the cellular complexes that contain GFP-LCA.

The blot from FIG. 30 was reprobed using a polyclonal antibody for SNAP-25 (FIG. 31). FIG. 31A shows a 25 kDa protein was detected in the reduced sample, which corresponds to the size of SNAP-25. This data confirms that SNAP-25 is immunoprecipitated with GFP-LCA. FIG. 31B shows the blot of the non-reduced samples, and the higher molecular weight proteins containing GFP-LCA were also detected using an antibody for SNAP-25. These data suggests GFP-LCA is in a complex that contains SNAP-25 when expressed in PC-12 cells.

Example 19

Proteins Expressed from the GFP-Light Chain Constructs can Inhibit Exocytosis when Expressed in Secretory Cell Lines:

The inventors have determined that the proteins expressed from the GFP-light chain constructs are active proteases with the ability to cleave specific SNARE proteins. In this example, the inventors also have demonstrated that these fusion proteins can inhibit exocytosis when expressed in secretory cell lines containing SNAP-25 and VAMP-2.

Methods:

Exocytosis Assay:

Exocytosis was measured using undifferentiated PC-12 cells exposed to tritium labeled norepinephrine (noradrenaline—Amersham). The labeled PC-12 cells were exposed to solutions containing various concentrations of potassium chloride and calcium chloride. The goal was to depolarize the PC-12 cells with potassium chloride and induce exocytosis via vesicle fusion with the plasma membrane with calcium chloride. The treated cells and the buffer containing the secreted $^3$H-noradrenline were collected separately and scintillation counted. Exocytosis was determined by calculating the percent norepinephrine released based on the formula below:

% label released=100*(number of dpm in buffer)/(number of dpm in cell+number of dpm in buffer)

Exocytosis was also analyzed using HIT-T15 cells, a hamster pancreatic cell line. This cell line is induced to secrete insulin when placed in media containing high glucose concentrations. HIT-T15 cells express SNAP-25 and their ability to secrete insulin is sensitive to treatment with BoNT-A. Insulin secretion was measured in HIT-T15 cells by placing the cells in DMEM containing high glucose (25 mM) or low glucose (5.6 mM). After 1 hour incubation at 37° C., the secretion media is collected and the amount of insulin secreted is determined using an insulin ELISA (APLCO diagnostics). Exocytosis is expressed as the amount of insulin secreted per $1\times10^5$ cells per hour.

Results:

Exocytosis Assay:

The inventors have demonstrated that the GFP-light chain construct produce active enzymes capable of inhibiting exocytosis when expressed in exocytotic cells.

The primary set of experiments was completed with PC-12 cells. The inventors detected a decrease in exocytosis by PC-12 cells treated with BoNT-A (FIG. 32). The cells were either untreated (control) or permbealized via electroporation in the presence or absence of 500 nM PURE A (purified *botulinum* toxin). First, analysis of the data reveals the percent norepinephrine released is significantly higher by PC-12 cells exposed to buffer containing a high concentration of potassium chloride (100 mM). It also appears the amount of $^3$H-norepinephorine secreted is lower in the PC-12 cells treated with 500 nM PURE A compared with untreated cells. This is expected as PURE A cleaves SNAP-25 causing an inhibition of exocytosis. These data confirm that an effect of BoNT-A treatment on PC-12 cells can be measured using this assay.

Figure 33:
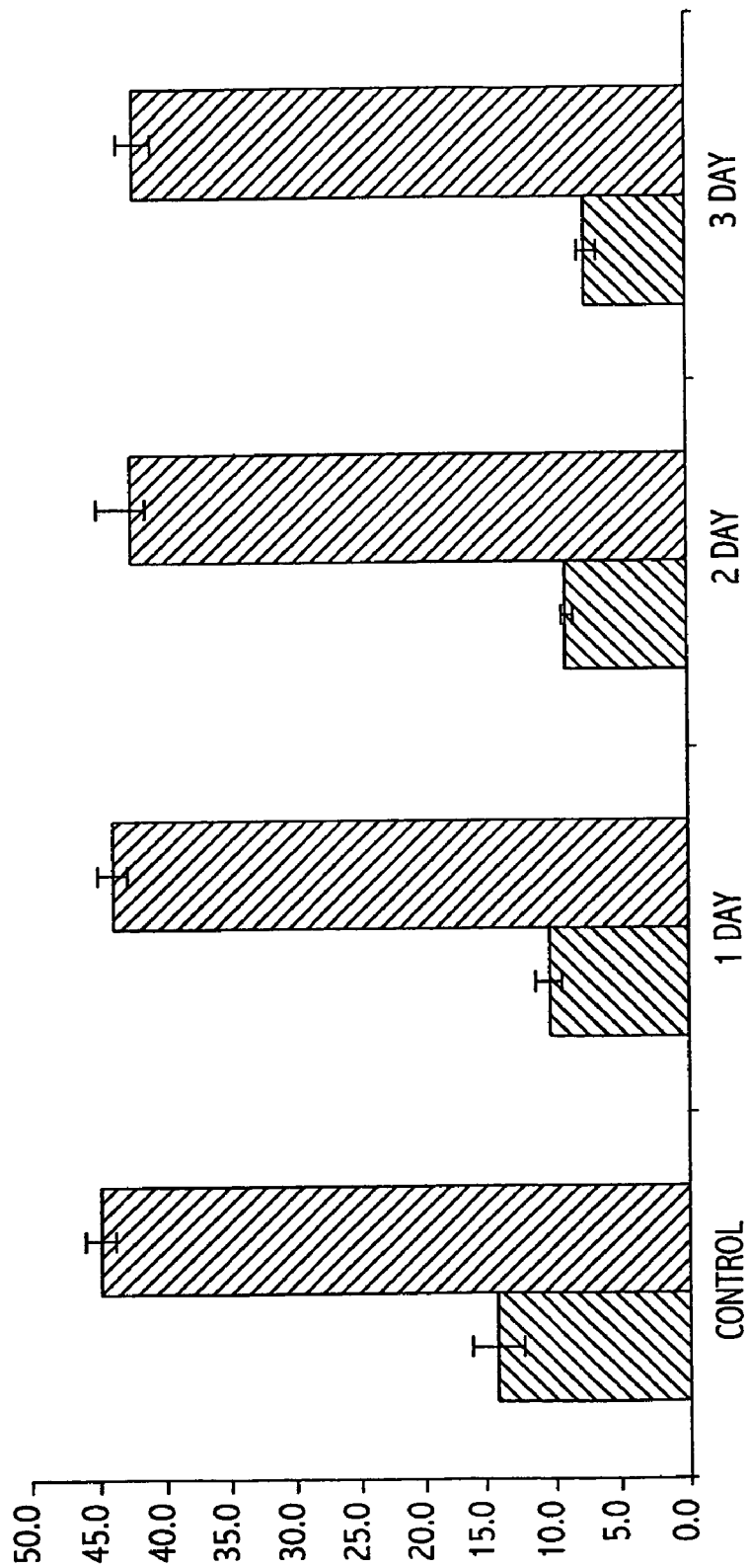
FIG. 33 is a graph showing the % norepinephrine released from PC-12 cells exposed to 500 nM PURE A for up to three days. Exocytosis was measured in cells placed in buffer containing 100 mM KCl without (light shaded bar) or with 2.2 mM $CaCl_2$ (Dark Shaded Bar). Exposure to 500 nM PURE A for up to three days has no effect on exocytosis by PC-12 cells. The Y-axis shows the % of norepinephrine released.

PC-12 cells are not known to express the receptor necessary for BoNT-A binding and uptake. This was confirmed as follows. Exocytosis in PC-12 cells exposed to 500 nM exogenous PURE A was measured for up to three days. Exocytosis was induced by placing cells in buffer containing 100 mM potassium chloride with or without 2.2 mM calcium chloride. Cells placed in buffer containing 2.2 mM calcium chloride released a higher amount of norepinephrine. These results indicate exocytosis can be induced when PC-12 cells are placed in a buffer containing a high concentration of potassium chloride supplemented with calcium chloride. The results in FIG. 33 also show no difference in exocytosis by cells exposed to exogenous 500 nM PURE A and untreated cells. These data confirm reported results that PC-12 cells do not contain the necessary receptor for the uptake of exogenous BoNT-A.

Figure 34:
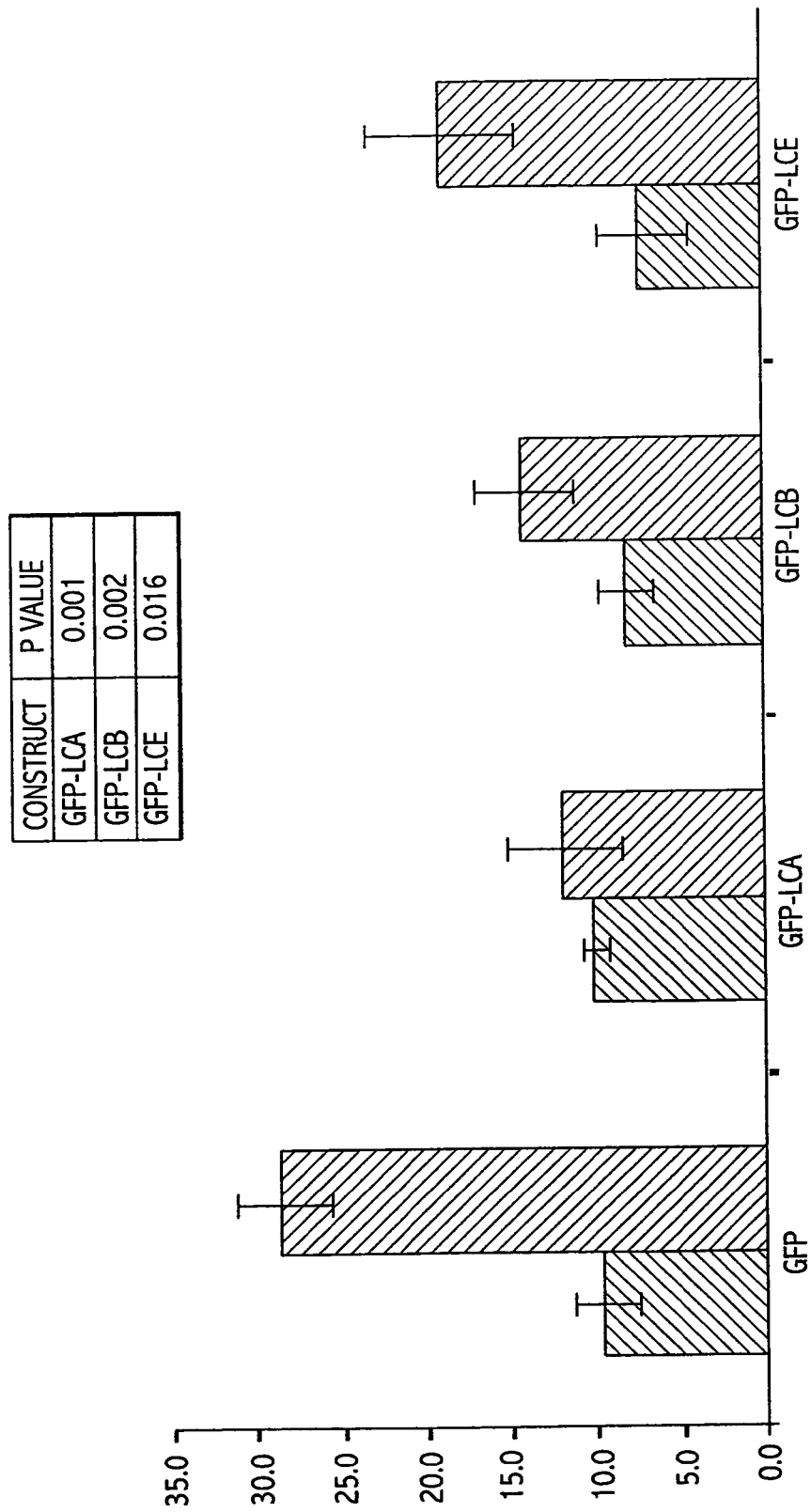
FIG. 34 is a graph showing the % norepinephrine released from PC-12 cells transfected with various plasmid constructs containing GFP and light chain fusion proteins. Exocytosis was measured in cells placed in buffer containing 100 mM KCl without (light shaded bar) or with 2.2 mM CaCl$_2$ (dark shaded bar). The constructs containing the light chain inhibited exocytosis when expressed in PC-12 cells. The Y-axis shows the % of norepinephrine released.
Figure 35:
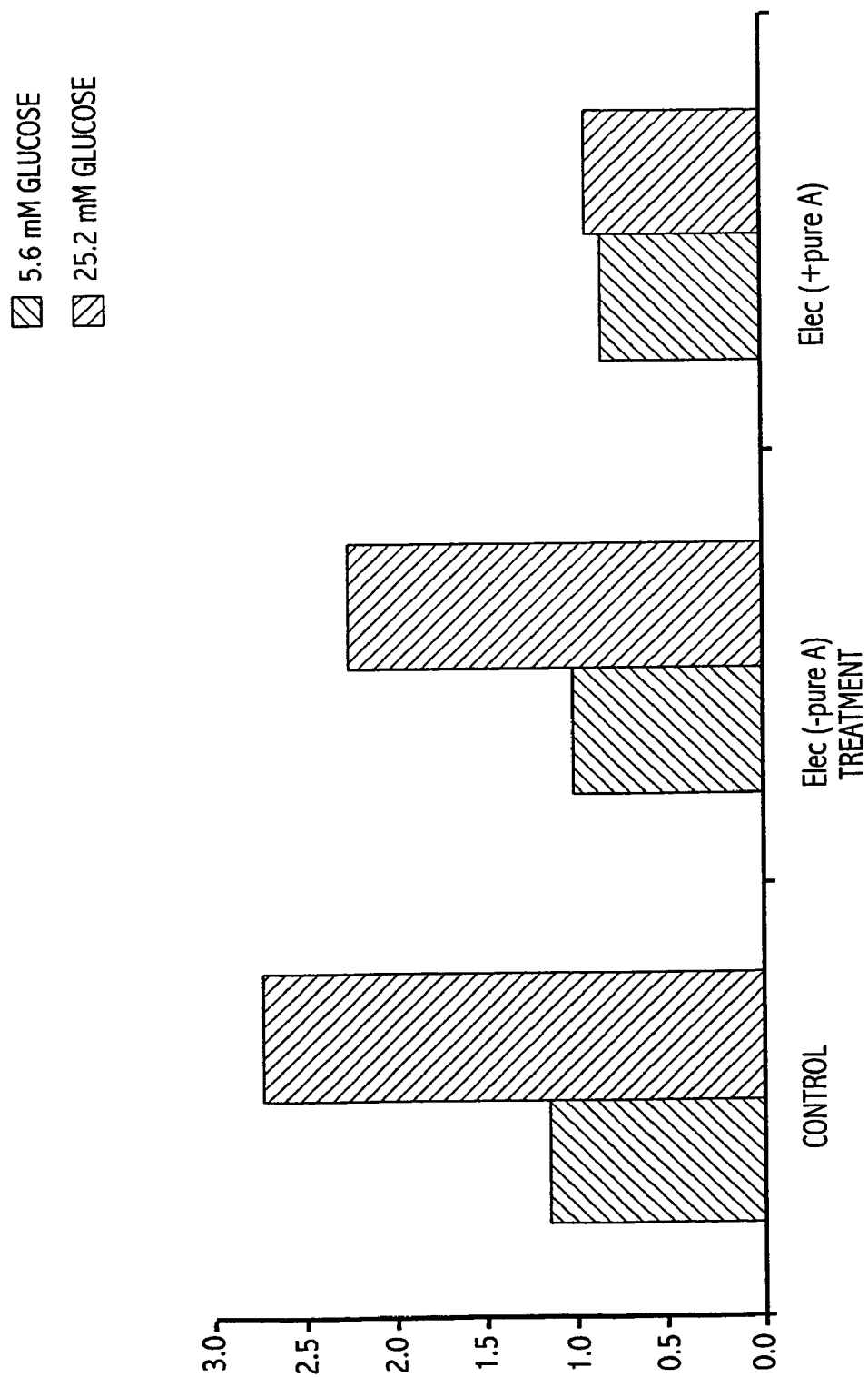
FIG. 35. is a graph showing the amount of insulin secreted by HIT-T15 cells placed in media containing high (25.2 mM) and low concentrations (5.6 mM) of glucose. The cells were untreated (control), electroporated, or electroporated in the presence of 500 nM PURE-A (electroporation/Pure A). PURE-A inhibited insulin secretion in electroporated HIT-T15 cells. The Y-axis shows the insulin released in ng/100,000 cells/hr.
Figure 36:
FIG. 36 shows a western blot of a cell lysate of HIT-T15 cell treated with PURE A. The blot was probed with a polyclonal antibody for the cleaved SNAP-25 produced by BoNT-A (SNAP-25$_{197}$). The cells were untreated (control)—lane 1, electroporated-lane 2, or electroporated in the presence of 500 nM PURE-A (electroporation/Pure A)-lane 3.

FIG. 34 shows the measurement of exocytosis by PC-12 cells transfected with plasmids containing the various GFP-light chain constructs. The cells containing the plasmid were selected by adding G418 to the growth media for three days. The data from the exocytosis assay shows the expressed fusion proteins inhibit $^3$H-norepinephrine release by PC-12 cells placed in 100 mM KCl and 2.2 mM CaCl$_2$. The inventors have shown that the GFP-LCA and GFP-LCE fusion proteins cleave SNAP-25$_{206}$ into SNAP-25$_{197}$ and SNAP-25$_{180}$, respectively. These data suggest the fusion proteins obtained from the expression of the plasmid constructs are active proteases that can inhibit exocytosis of PC-12 cells A hamster pancreatic cell line, HIT-T15, was also used to determine if active enzymes are produced by the various GFP-light chain constructs. This is a non-neuronal cell line that secretes insulin when placed in media containing high concentrations of glucose. These cells contain SNAP-25 and their ability to secrete insulin has been shown to be sensitive to BoNT-A. The inventors confirmed that these cells secrete insulin in response to glucose, and this exocytosis is inhibited by BoNT-A. FIG. 35 shows the insulin secretion by HIT-T15 cells in response to high levels of glucose. The amount of insulin secreted by these cells is greater when placed in media containing high concentrations of glucose. FIG. 35 also shows insulin secretion is inhibited in HIT-T15 cells electroporated in the presence of 500 nM BoNT-A. The lysates from the cells treated with BoNT-A were found to contain the cleaved SNAP-25 produced by BoNT-A when analyzed via Western blots (FIG. 36). These data suggest insulin secretion in HIT-T15 is inhibited by BoNT-A cleavage of SNAP-25.

Figure 37:
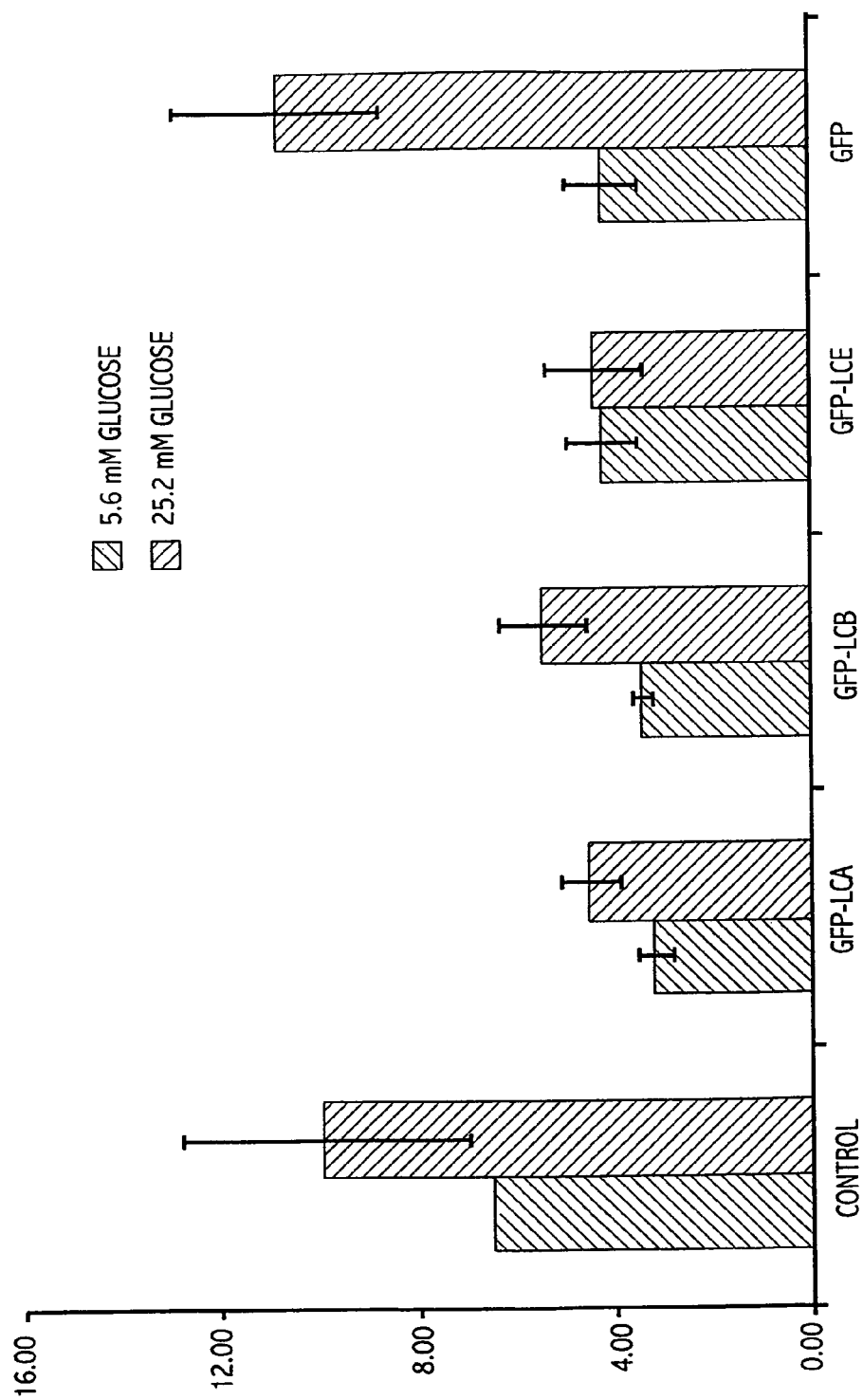
FIG. 37 is a graph showing the amount of insulin released from HIT-T15 cells transfected with various plasmid constructs containing GFP and light chain fusion proteins. Exocytosis was measured in cells placed in media containing 5.6 mM glucose (light shaded bar) or 25.6 mM glucose (dark shaded bar). The constructs containing the light chain inhibited exocytosis when expressed in PC-12 cells. The Y-axis shows the insulin released in ng/1,000,000 cells/hr.

FIG. 37 shows the measurement of insulin released by HIT-T15 cells transfected with plasmids containing the various GFP-light chain fusion proteins. There was a decrease in the amount of insulin secreted by cells transfected with the plasmids containing light chain constructs when compared with untransfected cells and cells transfected with the plasmid containing GFP. This inhibition was especially seen when the cells were placed in media containing high concentrations of glucose. These data provide additional evidence the constructs produce active forms of the *botulinum* neurotoxin light chain.

While this invention has been described with respect to various specific examples and embodiments, it is to be understood that the invention is not limited thereto and that it can be variously practiced with the scope of the following claims. All articles, references, publications, and patents set forth above are incorporated herein by reference in their entireties.

What is claimed is:

1. A modified *botulinum* neurotoxin type A, wherein the modification is one or more additional amino acid sequences comprising SEQ ID NO: 27 within the N-terminal 30 amino acids of a wild-type *botulinum* toxin type A light chain, wherein the additional amino acid sequence comprising SEQ ID NO: 27 increases biological half-life of the modified *botulinum* neurotoxin type A relative to an identical *botulinum* neurotoxin type A without the additional amino acid sequence comprising SEQ ID NO: 27.

2. The modified *botulinum* neurotoxin type A of claim 1, further comprising a modification of adding one or more additional leucine-based motifs of SEQ ID NO: 18 within the C-terminal 50 amino acids of the wild-type *botulinum* toxin type A light chain, wherein the additional leucine-based motif of SEQ ID NO: 18 increases biological half- life of the modified *botulinum* neurotoxin type A relative to an identical *botulinum* neurotoxin type A without the additional leucine-based motif.

3. The modified *botulinum* neurotoxin type A of claim 2, wherein the additional leucine-based motif is SEQ ID NO: 1, SEQ ID NO: 4, SEQ ID NO: 6, or SEQ ID NO: 13.

* * * * *

UNITED STATES PATENT AND TRADEMARK OFFICE
CERTIFICATE OF CORRECTION

PATENT NO. : 7,491,799 B2 Page 1 of 3
APPLICATION NO. : 10/757077
DATED : February 17, 2009
INVENTOR(S) : Steward et al.

It is certified that error appears in the above-identified patent and that said Letters Patent is hereby corrected as shown below:

On the Title Page, Item (56), under "Other Publications", line 21, delete "botullsm" and insert -- botulism --, therefor.

In column 1, line 23, delete "botulinum" and insert -- Botulinum --, therefor.

In column 1, line 26, delete "botulinum" and insert -- Botulinum --, therefor.

In column 6, line 39, delete "derivativization" and insert -- derivatization --, therefor.

In column 7, line 57, delete "caseine" and insert -- casein --, therefor.

In column 8, line 5, delete "caseine" and insert -- casein --, therefor.

In column 8, line 56, delete "caseine" and insert -- casein --, therefor.

In column 10, line 63, below "membrane." insert -- Fig. 6 shows an x-ray crystallographic structure of botulinum toxintype A. --.

In column 11, line 65, delete "Light Chain" and insert -- light chain --, therefor.

In column 12, line 8, delete "Light Chains" and insert -- light chains --, therefor.

In column 14, line 14, after "18)" insert -- , --.

In column 15, line 31, delete "B." and insert -- B, --, therefor.

In column 18, line 65, delete "HaIIA" and insert -- HAIIA --, therefor.

In column 20, line 1, delete "botulinumtoxin" and insert -- botulinum toxin --, therefor.

In column 20, line 21, delete "botulinum" and insert -- Botulinum --, therefor.

Signed and Sealed this

Twenty-first Day of December, 2010

David J. Kappos
*Director of the United States Patent and Trademark Office*

CERTIFICATE OF CORRECTION (continued)
U.S. Pat. No. 7,491,799 B2

In column 28, line 64, delete "MgCl2" and insert -- $MgCl_2$ --, therefor.

In column 30, line 4, delete "CaCl2" and insert -- $CaCl_2$ --, therefor.

In column 33, line 43, after "botulinum" insert -- . --.

In column 34, line 40, delete "(Stemberger)" and insert -- (Sternberger) --, therefor.

In column 35, line 31, delete "(Stemberger)" and insert -- (Sternberger) --, therefor.

In column 35, line 34, after "mutants" insert -- . --.

In column 43, line 24, delete "$EC_5rLC/A(LL-->AA)$" and insert -- $EC_{50}rLC/A(LL-->AA)$ --, therefor.

In column 43, line 28, delete "C1" and insert -- $C_1$ --, therefor.

In column 45, line 41, delete "RGIVDRLNKVLVCISDPNININIYKNKEKDKYKFVED" and insert -- RGIVDRLNKVLVCISDPNININIYKNKFKDKYKFVED --, therefor.

In column 46, line 16, delete "KYEFLKVPNLLDDDIYTVSEGFNIGNLAVNRGQSIKL" and insert -- KYEFLKVPNLLDDDIYTVSEGFNIGNLAVNNRGQSIKL --, therefor.

In column 46, line 55, delete "VLQNFRGIVDRLNKVLVCISDPNININIYKNFKDKYK" and insert -- VLQNFRGIVDRLNKVLVCISDPNININIYKNFKDKYK --, therefor.

In column 46, line 60, delete "NMGKEYRGQNKAINKQAYEEISKEHLAVYKIQMGKSV" and insert -- NMGKEYRGQNKAINKQAYEEISKEHLAVYKIQMCKSV --, therefor.

In column 48, line 26, delete "MPVTINNFNPMPFVNKQFNYKDPVNGVDIAYIKIPNAG" and insert -- MPVTINNFNMPFVNKQFNYKDPVNGVDIAYIKIPNAG --, therefor.

In column 49, line 26, delete "sterotypes," and insert -- serotypes, --, therefor.

In column 50, line 50, delete "C1" and insert -- $C_1$ --, therefor.

In column 51, line 15, delete "C1" and insert -- $C_1$ --, therefor.

In column 51, line 25, delete "C1" and insert -- $C_1$ --, therefor.

In column 51, line 36, delete "C1" and insert -- $C_1$ --, therefor.

In column 51, line 63, delete "LCA-GFP-GFP" and insert -- LCA-GFP --, therefor.

In column 51, line 66, delete "LCE-GFP-GFP" and insert -- LCE-GFP --, therefor.

In column 52, line 2, delete "LCB-GFP-GFP" and insert -- LCB-GFP --, therefor.

In column 52, line 3, delete "LCB-GFP-GFP" and insert -- LCB-GFP --, therefor.

CERTIFICATE OF CORRECTION (continued)
U.S. Pat. No. 7,491,799 B2

In column 52, line 7, delete "LCB-GFP-GFP" and insert -- LCB-GFP --, therefor.

In column 52, line 8, delete "LCB-GFP-GFP" and insert -- LCB-GFP --, therefor.

In column 52, line 10, delete "LCB-GFP-GFP" and insert -- LCB-GFP --, therefor.

In column 52, line 41, after "expression" insert -- . --.

In column 52, line 55, delete "(Stemberger)" and insert -- (Sternberger) --, therefor.

In column 56, line 40, delete "$^3$H-noradrenline" and insert -- $^3$H-noradrenaline --, therefor.

In column 57, line 1, delete "permbealized" and insert -- permeabilized --, therefor.

In column 57, line 7, delete "$^3$H-norepinephorine" and insert -- $^3$H-norepinephrine --, therefor.

SEQUENCE LISTING

<160> NUMBER OF SEQ ID NOS: 136

<210> SEQ ID NO 1
<211> LENGTH: 7
<212> TYPE: PRT
<213> ORGANISM: Clostridium botulinum

<400> SEQUENCE: 1

Phe Glu Phe Tyr Lys Leu Leu
1               5

<210> SEQ ID NO 2
<211> LENGTH: 7
<212> TYPE: PRT
<213> ORGANISM: Rat

<400> SEQUENCE: 2

Glu Glu Lys Arg Ala Ile Leu
1               5

<210> SEQ ID NO 3
<211> LENGTH: 7
<212> TYPE: PRT

```
<213> ORGANISM: Rat

<400> SEQUENCE: 3

Glu Glu Lys Met Ala Ile Leu
1               5

<210> SEQ ID NO 4
<211> LENGTH: 7
<212> TYPE: PRT
<213> ORGANISM: Rat

<400> SEQUENCE: 4

Ser Glu Arg Asp Val Leu Leu
1               5

<210> SEQ ID NO 5
<211> LENGTH: 7
<212> TYPE: PRT
<213> ORGANISM: Rat

<400> SEQUENCE: 5

Val Asp Thr Gln Val Leu Leu
1               5

<210> SEQ ID NO 6
<211> LENGTH: 8
<212> TYPE: PRT
<213> ORGANISM: Mouse

<400> SEQUENCE: 6

Ala Glu Val Gln Gln Asn Leu Leu
1               5

<210> SEQ ID NO 7
<211> LENGTH: 7
<212> TYPE: PRT
<213> ORGANISM: Frog

<400> SEQUENCE: 7

Ser Asp Lys Gln Asn Leu Leu
1               5

<210> SEQ ID NO 8
<211> LENGTH: 7
<212> TYPE: PRT
<213> ORGANISM: Chicken

<400> SEQUENCE: 8

Ser Asp Arg Gln Asn Leu Ile
1               5

<210> SEQ ID NO 9
<211> LENGTH: 7
<212> TYPE: PRT
<213> ORGANISM: Sheep

<400> SEQUENCE: 9

Ala Asp Thr Gln Val Leu Met
1               5

<210> SEQ ID NO 10
<211> LENGTH: 7
<212> TYPE: PRT
<213> ORGANISM: Homo sapiens
```

-continued

```
<400> SEQUENCE: 10

Ser Asp Lys Gln Thr Leu Leu
1               5

<210> SEQ ID NO 11
<211> LENGTH: 7
<212> TYPE: PRT
<213> ORGANISM: Homo sapiens

<400> SEQUENCE: 11

Ser Gln Ile Lys Arg Leu Leu
1               5

<210> SEQ ID NO 12
<211> LENGTH: 7
<212> TYPE: PRT
<213> ORGANISM: Homo sapiens

<400> SEQUENCE: 12

Ala Asp Thr Gln Ala Leu Leu
1               5

<210> SEQ ID NO 13
<211> LENGTH: 7
<212> TYPE: PRT
<213> ORGANISM: Homo sapiens

<400> SEQUENCE: 13

Asn Glu Gln Ser Pro Leu Leu
1               5

<210> SEQ ID NO 14
<211> LENGTH: 30
<212> TYPE: PRT
<213> ORGANISM: Clostridium botulinum

<400> SEQUENCE: 14

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met
            20                  25                  30

<210> SEQ ID NO 15
<211> LENGTH: 50
<212> TYPE: PRT
<213> ORGANISM: Clostridium botulinum

<400> SEQUENCE: 15

Gly Phe Asn Leu Arg Asn Thr Asn Leu Ala Ala Asn Phe Asn Gly Gln
1               5                   10                  15

Asn Thr Glu Ile Asn Asn Met Asn Phe Thr Lys Leu Lys Asn Phe Thr
            20                  25                  30

Gly Leu Phe Glu Phe Tyr Lys Leu Leu Cys Val Arg Gly Ile Ile Thr
        35                  40                  45

Ser Lys
    50

<210> SEQ ID NO 16
<211> LENGTH: 30
<212> TYPE: PRT
<213> ORGANISM: Clostridium botulinum

<400> SEQUENCE: 16
```

-continued

```
Met Pro Val Thr Ile Asn Asn Phe Asn Tyr Asn Asp Pro Ile Asp Asn
 1               5                  10                  15

Asp Asn Ile Ile Met Met Glu Pro Pro Phe Ala Arg Gly Thr
            20                  25                  30

<210> SEQ ID NO 17
<211> LENGTH: 50
<212> TYPE: PRT
<213> ORGANISM: Clostridium botulinum

<400> SEQUENCE: 17

Tyr Thr Ile Glu Glu Gly Phe Asn Ile Ser Asp Lys Asn Met Gly Lys
 1               5                  10                  15

Glu Tyr Arg Gly Gln Asn Lys Ala Ile Asn Lys Gln Ala Tyr Glu Glu
            20                  25                  30

Ile Ser Lys Glu His Leu Ala Val Tyr Lys Ile Gln Met Cys Lys Ser
        35                  40                  45

Val Lys
    50

<210> SEQ ID NO 18
<211> LENGTH: 30
<212> TYPE: PRT
<213> ORGANISM: Clostridium botulinum

<400> SEQUENCE: 18

Met Pro Ile Thr Ile Asn Asn Phe Asn Tyr Ser Asp Pro Val Asp Asn
 1               5                  10                  15

Lys Asn Ile Leu Tyr Leu Asp Thr His Leu Asn Thr Leu Ala
            20                  25                  30

<210> SEQ ID NO 19
<211> LENGTH: 50
<212> TYPE: PRT
<213> ORGANISM: Clostridium botulinum

<400> SEQUENCE: 19

Asn Ile Pro Lys Ser Asn Leu Asn Val Leu Phe Met Gly Gln Asn Leu
 1               5                  10                  15

Ser Arg Asn Pro Ala Leu Arg Lys Val Asn Pro Glu Asn Met Leu Tyr
            20                  25                  30

Leu Phe Thr Lys Phe Cys His Lys Ala Ile Asp Gly Arg Ser Leu Tyr
        35                  40                  45

Asn Lys
    50

<210> SEQ ID NO 20
<211> LENGTH: 30
<212> TYPE: PRT
<213> ORGANISM: Clostridium botulinum

<400> SEQUENCE: 20

Met Thr Trp Pro Val Lys Asp Phe Asn Tyr Ser Asp Pro Val Asn Asp
 1               5                  10                  15

Asn Asp Ile Leu Tyr Leu Arg Ile Pro Gln Asn Lys Leu Ile
            20                  25                  30

<210> SEQ ID NO 21
<211> LENGTH: 50
<212> TYPE: PRT
```

-continued

<213> ORGANISM: Clostridium botulinum

<400> SEQUENCE: 21

Tyr Thr Ile Arg Asp Gly Phe Asn Leu Thr Asn Lys Gly Phe Asn Ile
1               5                   10                  15

Glu Asn Ser Gly Gln Asn Ile Glu Arg Asn Pro Ala Leu Gln Lys Leu
            20                  25                  30

Ser Ser Glu Ser Val Val Asp Leu Phe Thr Lys Val Cys Arg Leu Leu
        35                  40                  45

Thr Lys
    50

<210> SEQ ID NO 22
<211> LENGTH: 30
<212> TYPE: PRT
<213> ORGANISM: Clostridium botulinum

<400> SEQUENCE: 22

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr
            20                  25                  30

<210> SEQ ID NO 23
<211> LENGTH: 50
<212> TYPE: PRT
<213> ORGANISM: Clostridium botulinum

<400> SEQUENCE: 23

Gly Tyr Asn Ile Asn Asn Leu Lys Val Asn Phe Arg Gly Gln Asn Ala
1               5                   10                  15

Asn Leu Asn Pro Arg Ile Ile Thr Pro Ile Thr Gly Arg Gly Leu Val
            20                  25                  30

Lys Lys Ile Ile Arg Phe Cys Lys Asn Ile Val Ser Val Lys Gly Ile
        35                  40                  45

Arg Lys
    50

<210> SEQ ID NO 24
<211> LENGTH: 30
<212> TYPE: PRT
<213> ORGANISM: Clostridium botulinum

<400> SEQUENCE: 24

Met Pro Val Ala Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser
            20                  25                  30

<210> SEQ ID NO 25
<211> LENGTH: 50
<212> TYPE: PRT
<213> ORGANISM: Clostridium botulinum

<400> SEQUENCE: 25

Thr Val Ser Glu Gly Phe Asn Ile Gly Asn Leu Ala Val Asn Asn Arg
1               5                   10                  15

Gly Gln Ser Ile Lys Leu Asn Pro Lys Ile Ile Asp Ser Ile Pro Asp
            20                  25                  30

Lys Gly Leu Val Glu Lys Ile Val Lys Phe Cys Lys Ser Val Ile Pro

Arg Lys
    50

<210> SEQ ID NO 26
<211> LENGTH: 30
<212> TYPE: PRT
<213> ORGANISM: Clostridium botulinum
<220> FEATURE:
<221> NAME/KEY: misc_feature
<222> LOCATION: (7)..(7)
<223> OTHER INFORMATION: Xaa is any amino acid.

<400> SEQUENCE: 26

Met Pro Val Asn Ile Lys Xaa Phe Asn Tyr Asn Asp Pro Ile Asn Asn
1               5                   10                  15

Asp Asp Ile Ile Met Met Glu Pro Phe Asn Asp Pro Gly Pro
            20                  25                  30

<210> SEQ ID NO 27
<211> LENGTH: 50
<212> TYPE: PRT
<213> ORGANISM: Clostridium botulinum

<400> SEQUENCE: 27

Gln Asn Glu Gly Phe Asn Ile Ala Ser Lys Asn Leu Lys Thr Glu Phe
1               5                   10                  15

Asn Gly Gln Asn Lys Ala Val Asn Lys Glu Ala Tyr Glu Glu Ile Ser
            20                  25                  30

Leu Glu His Leu Val Ile Tyr Arg Ile Ala Met Cys Lys Pro Val Met
        35                  40                  45

Tyr Lys
    50

<210> SEQ ID NO 28
<211> LENGTH: 30
<212> TYPE: PRT
<213> ORGANISM: Clostridium botulinum

<400> SEQUENCE: 28

Met Pro Phe Ala Asn Lys Gln Phe Asn Tyr Lys Asp Pro Val Asn Gly
1               5                   10                  15

Val Asp Ile Ala Tyr Ile Lys Ile Pro Asn Ala Gly Gln Met
            20                  25                  30

<210> SEQ ID NO 29
<211> LENGTH: 50
<212> TYPE: PRT
<213> ORGANISM: Clostridium botulinum

<400> SEQUENCE: 29

Gly Phe Asn Leu Arg Asn Thr Asn Leu Ala Ala Asn Phe Asn Gly Gln
1               5                   10                  15

Asn Thr Glu Ile Asn Asn Met Asn Arg Thr Lys Leu Lys Asn Phe Thr
            20                  25                  30

Gly Leu Phe Glu Phe Tyr Lys Leu Leu Cys Val Arg Gly Ile Ile Thr
        35                  40                  45

Ser Lys
    50

<210> SEQ ID NO 30

```
<211> LENGTH: 30
<212> TYPE: PRT
<213> ORGANISM: Clostridium botulinum

<400> SEQUENCE: 30

Met Pro Phe Val Asn Lys Gln Phe Asn Lys Asp Pro Val Asn Gly
1               5                   10                  15

Val Asp Ile Ala Tyr Ile Lys Ile Pro Asn Ala Gly Gln Met
            20                  25                  30

<210> SEQ ID NO 31
<211> LENGTH: 50
<212> TYPE: PRT
<213> ORGANISM: Clostridium botulinum

<400> SEQUENCE: 31

Gly Phe Asn Leu Arg Asn Thr Asn Leu Ala Ala Asn Phe Asn Gly Gln
1               5                   10                  15

Asn Thr Glu Ile Asn Asn Met Asn Phe Thr Lys Leu Lys Asn Ala Ala
            20                  25                  30

Gly Leu Phe Glu Phe Tyr Lys Leu Leu Cys Val Arg Gly Ile Ile Thr
        35                  40                  45

Ser Lys
    50

<210> SEQ ID NO 32
<211> LENGTH: 30
<212> TYPE: PRT
<213> ORGANISM: Clostridium botulinum

<400> SEQUENCE: 32

Met Pro Phe Val Asn Lys Gln Phe Asn Tyr Lys Asp Pro Val Asn Gly
1               5                   10                  15

Val Asp Ile Ala Arg Ile Lys Ile Pro Asn Ala Gly Gln Met
            20                  25                  30

<210> SEQ ID NO 33
<211> LENGTH: 50
<212> TYPE: PRT
<213> ORGANISM: Clostridium botulinum

<400> SEQUENCE: 33

Gly Phe Asn Leu Arg Asn Thr Asn Leu Ala Ala Asn His Asn Gly Gln
1               5                   10                  15

Asn Thr Glu Ile Asn Asn Met Asn Phe Thr Lys Leu Lys Asn Phe Thr
            20                  25                  30

Gly Leu Phe Glu Phe Tyr Lys Leu Leu Cys Val Arg Gly Ile Ile Thr
        35                  40                  45

Ser Lys
    50

<210> SEQ ID NO 34
<211> LENGTH: 30
<212> TYPE: PRT
<213> ORGANISM: Clostridium botulinum

<400> SEQUENCE: 34

Met Pro Phe Val Asn Lys His Phe Asn Tyr Lys Asp Pro Val Asn Gly
1               5                   10                  15

Val Asp Ile Ala Tyr Ile Lys Ile Pro Asn Ala Gly Gln Met
            20                  25                  30
```

<210> SEQ ID NO 35
<211> LENGTH: 50
<212> TYPE: PRT
<213> ORGANISM: Clostridium botulinum

<400> SEQUENCE: 35

Gly Phe Asn Leu Arg Asn Thr Asn Leu Ala Ala Asn Phe Asn Gly Gln
1               5                   10                  15

Asn Thr Glu Ile Asn Asn Met Asn Phe Thr Lys Leu Lys Asn Phe Thr
            20                  25                  30

Gly Leu Phe Glu Phe Tyr Lys Leu Leu Cys Ala Arg Gly Ile Ile Thr
        35                  40                  45

Ser Lys
    50

<210> SEQ ID NO 36
<211> LENGTH: 30
<212> TYPE: PRT
<213> ORGANISM: Clostridium botulinum

<400> SEQUENCE: 36

Met Pro Ala Thr Ile Asn Asn Phe Asn Tyr Asn Asp Pro Ile Asp Asn
1               5                   10                  15

Asp Asn Ile Ile Met Met Glu Pro Pro Phe Ala Arg Gly Thr
            20                  25                  30

<210> SEQ ID NO 37
<211> LENGTH: 50
<212> TYPE: PRT
<213> ORGANISM: Clostridium botulinum

<400> SEQUENCE: 37

Tyr Thr Ile Glu Glu Gly Phe Asn Ile Ser Asp Asn Lys Met Gly Lys
1               5                   10                  15

Glu Tyr Arg Gly Gln Asn Lys Ala Ile Asn Lys Gln Ala Tyr Glu Glu
            20                  25                  30

Ile Ser Lys Glu His Leu Ala Val Tyr Lys Ile Arg Met Cys Lys Ser
        35                  40                  45

Val Lys
    50

<210> SEQ ID NO 38
<211> LENGTH: 30
<212> TYPE: PRT
<213> ORGANISM: Clostridium botulinum

<400> SEQUENCE: 38

Met Pro Val Thr Ile Asn Asn Phe Asn Tyr Asn Asp Pro Ile Asp Asn
1               5                   10                  15

Asp Asn Ile Ile Ala Ala Glu Pro Pro Phe Ala Arg Gly Thr
            20                  25                  30

<210> SEQ ID NO 39
<211> LENGTH: 50
<212> TYPE: PRT
<213> ORGANISM: Clostridium botulinum

<400> SEQUENCE: 39

Tyr Thr Ile Glu Glu Gly Phe Asn Ile Ser Asp Asn Lys Met Gly Lys
1               5                   10                  15

```
Glu Tyr Arg Gly Gln Asn Lys Ala Ile Asn Lys Gln Ala Tyr Glu Glu
            20                  25                  30

Ile Ser Lys Glu His Leu Ala Val Arg Lys Ile Gln Met Cys Lys Ser
        35                  40                  45

Val Lys
    50
```

<210> SEQ ID NO 40
<211> LENGTH: 30
<212> TYPE: PRT
<213> ORGANISM: Clostridium botulinum

<400> SEQUENCE: 40

```
Met Pro Val Thr Ile Asn Asn Phe Asn Arg Asn Asp Pro Ile Asp Asn
1               5                   10                  15

Asp Asn Ile Ile Met Met Glu Pro Pro Phe Ala Arg Gly Thr
            20                  25                  30
```

<210> SEQ ID NO 41
<211> LENGTH: 50
<212> TYPE: PRT
<213> ORGANISM: Clostridium botulinum

<400> SEQUENCE: 41

```
Tyr Thr Ile Glu Glu Gly Phe Asn Ile Ser Asp Asn Lys Met Gly Lys
1               5                   10                  15

Glu Tyr Arg Gly Gln Asn Lys Ala Ile Asn Lys Gln Ala Lys Glu Glu
            20                  25                  30

Ile Ser Lys Glu His Leu Ala Val Tyr Lys Ile Gln Met Cys Lys Ser
        35                  40                  45

Val Lys
    50
```

<210> SEQ ID NO 42
<211> LENGTH: 30
<212> TYPE: PRT
<213> ORGANISM: Clostridium botulinum

<400> SEQUENCE: 42

```
Met Pro Ile Thr Ile Asn Asn Lys Asn Tyr Ser Asp Pro Val Asp Asn
1               5                   10                  15

Lys Asn Ile Leu Tyr Leu Asp Thr His Leu Asn Thr Leu Ala
            20                  25                  30
```

<210> SEQ ID NO 43
<211> LENGTH: 50
<212> TYPE: PRT
<213> ORGANISM: Clostridium botulinum

<400> SEQUENCE: 43

```
Asn Ile Pro Lys Ser Asn Leu Asn Val Leu Phe Met Gly Gln Asn Leu
1               5                   10                  15

Ser Arg Asn Pro Ala Leu Arg Lys Val Asn Pro Glu Asn Met Leu Tyr
            20                  25                  30

Leu Phe Thr Lys Phe Cys His Lys Ala Ile Asp Gly Arg Ser Leu Arg
        35                  40                  45

Asn Lys
    50
```

<210> SEQ ID NO 44
<211> LENGTH: 30
<212> TYPE: PRT
<213> ORGANISM: Clostridium botulinum

<400> SEQUENCE: 44

Met Thr Trp Pro Ala Lys Asp Phe Asn Tyr Ser Asp Pro Ala Asn Asp
1               5                   10                  15

Asn Asp Ile Leu Tyr Leu Arg Ile Pro Gln Asn Lys Leu Ile
            20                  25                  30

<210> SEQ ID NO 45
<211> LENGTH: 50
<212> TYPE: PRT
<213> ORGANISM: Clostridium botulinum

<400> SEQUENCE: 45

Tyr Thr Ile Arg Asp Gly Phe Asn Leu Thr Asn Lys Gly Phe Asn Ile
1               5                   10                  15

Glu Asn Ser Gly Gln Asn Ile Glu Arg Asn Pro Ala Leu Gln Lys Leu
            20                  25                  30

Ser Ser Glu Ser Val Val Asp Leu Phe Thr Lys Ala Cys Leu Arg Leu
        35                  40                  45

Thr Lys
    50

<210> SEQ ID NO 46
<211> LENGTH: 30
<212> TYPE: PRT
<213> ORGANISM: Clostridium botulinum

<400> SEQUENCE: 46

Met Pro Lys Ile Asn Ser Phe Asn Tyr Asn Asp Pro Ala Asn Asp Arg
1               5                   10                  15

Thr Ile Leu Tyr Ile Lys Pro Gly Gly Cys Gln Glu Phe Tyr
            20                  25                  30

<210> SEQ ID NO 47
<211> LENGTH: 50
<212> TYPE: PRT
<213> ORGANISM: Clostridium botulinum

<400> SEQUENCE: 47

Gly Tyr Asn Ile Asn Asn Leu Lys Val Asn Phe Arg Gly Gln Asn Ala
1               5                   10                  15

Asn Leu Asn Pro Arg Ile Ile Thr Pro Ile Thr Gly Arg Gly His Val
            20                  25                  30

Lys Lys Ile Ile Arg Phe Cys Lys Asn Ile Val Ser Val Lys Gly Ile
        35                  40                  45

Arg Lys
    50

<210> SEQ ID NO 48
<211> LENGTH: 30
<212> TYPE: PRT
<213> ORGANISM: Clostridium botulinum

<400> SEQUENCE: 48

Met Pro Lys Ile Asn Ser Arg Asn Tyr Asn Asp Pro Val Asn Asp Arg
1               5                   10                  15

Thr Ile Leu Tyr Ile Lys Pro Gly Gly Cys Gln Glu Phe Tyr

-continued

```
                    20                  25                  30

<210> SEQ ID NO 49
<211> LENGTH: 50
<212> TYPE: PRT
<213> ORGANISM: Clostridium botulinum

<400> SEQUENCE: 49

Gly Tyr Asn Ile Asn Asn Leu Lys Val Asn Phe Arg Gly Gln Asn Ala
1               5                   10                  15

Asn Leu Asn Pro Arg Ile Ile Thr Pro Ile Thr Gly Arg Gly Leu Val
                20                  25                  30

Lys Lys Ile Ile Arg Phe Cys Lys Asn Ala Ala Ser Val Lys Gly Ile
            35                  40                  45

Arg Lys
    50

<210> SEQ ID NO 50
<211> LENGTH: 30
<212> TYPE: PRT
<213> ORGANISM: Clostridium botulinum

<400> SEQUENCE: 50

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Arg
                20                  25                  30

<210> SEQ ID NO 51
<211> LENGTH: 50
<212> TYPE: PRT
<213> ORGANISM: Clostridium botulinum

<400> SEQUENCE: 51

Gly Tyr Asn Ile Asn Asn Leu Lys Val Asn Phe Arg Gly Gln Asn Ala
1               5                   10                  15

Asn Leu Asn Pro Arg Ile Ile Thr Pro Ile Thr Gly Arg Gly Leu Val
                20                  25                  30

Lys Lys Ile Ile Arg Phe Cys Lys Asn Ile Val Ser Ala Lys Gly Ile
            35                  40                  45

Arg Lys
    50

<210> SEQ ID NO 52
<211> LENGTH: 30
<212> TYPE: PRT
<213> ORGANISM: Clostridium botulinum

<400> SEQUENCE: 52

Met Pro Ala Ala Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser
                20                  25                  30

<210> SEQ ID NO 53
<211> LENGTH: 50
<212> TYPE: PRT
<213> ORGANISM: Clostridium botulinum

<400> SEQUENCE: 53

Thr Val Ser Glu Gly Phe Asn Ile Gly Asn Leu Ala Val Asn Asn Arg
```

```
                 1               5                  10                 15
Gly Gln Ser Ile Lys Leu Asn Pro Lys Ile Ile Asp Ser Ile Pro Asp
                20                  25                  30

Lys Gly Leu Val Glu Lys Ile Val Lys Phe Cys Lys Ser Ala Ile Pro
            35                  40                  45

Arg Lys
    50

<210> SEQ ID NO 54
<211> LENGTH: 30
<212> TYPE: PRT
<213> ORGANISM: Clostridium botulinum
<220> FEATURE:
<221> NAME/KEY: misc_feature
<222> LOCATION: (7)..(7)
<223> OTHER INFORMATION: Xaa is any amino acid.

<400> SEQUENCE: 54

Met Pro Val Asn Ile Lys Xaa His Asn Tyr Asn Asp Pro Ile Asn Asn
1               5                   10                  15

Asp Asp Ile Ile Met Met Glu Pro Phe Asn Asp Pro Gly Pro
            20                  25                  30

<210> SEQ ID NO 55
<211> LENGTH: 50
<212> TYPE: PRT
<213> ORGANISM: Clostridium botulinum

<400> SEQUENCE: 55

Gln Asn Glu Gly Phe Asn Ile Ala Ser Lys Asn Leu Lys Thr Glu Phe
1               5                   10                  15

Asn Gly Gln Asn Lys Ala Val Asn Lys Glu Ala Tyr Glu Glu Ile Ser
                20                  25                  30

Leu Glu His Leu Val Ile Tyr Arg Ile Ala Met Cys Lys Pro Ala Met
            35                  40                  45

Tyr Lys
    50

<210> SEQ ID NO 56
<211> LENGTH: 26
<212> TYPE: PRT
<213> ORGANISM: Clostridium botulinum

<400> SEQUENCE: 56

Met Pro Phe Val Asn Lys Gln Phe Asn Tyr Lys Asp Pro Val Asn Gly
1               5                   10                  15

Val Asp Ile Ala Tyr Ile Lys Ile Pro His
            20                  25

<210> SEQ ID NO 57
<211> LENGTH: 43
<212> TYPE: PRT
<213> ORGANISM: Clostridium botulinum

<400> SEQUENCE: 57

Gly Phe Asn Leu Arg Asn Thr Asn Leu Ala Ala Asn Phe Asn Gly Gln
1               5                   10                  15

Asn Thr Glu Ile Asn Asn Met Asn Ala Ala Ala Ala Ala Ala Ala Ala
                20                  25                  30

Ala Ala Cys Val Arg Gly Ile Ile Thr Ser Lys
            35                  40
```

<210> SEQ ID NO 58
<211> LENGTH: 26
<212> TYPE: PRT
<213> ORGANISM: Clostridium botulinum

<400> SEQUENCE: 58

Met Ala Ala Asn Tyr Lys Pro Asp Val Asn Gly Val Asp Ile Ala
1               5                   10                  15

Tyr Ile Lys Ile Pro Asn Ala Gly Gln Met
            20                  25

<210> SEQ ID NO 59
<211> LENGTH: 48
<212> TYPE: PRT
<213> ORGANISM: Clostridium botulinum

<400> SEQUENCE: 59

Gly Lys Asn Leu Arg Asn Thr Asn Leu Ala Ala Asn Phe Asn Gly Gln
1               5                   10                  15

Asn Thr Glu Ile Asn Asn Met Asn Phe Thr Lys Leu Lys Asn Phe Thr
            20                  25                  30

Gly Leu Phe Glu Phe Tyr Lys Cys Val Arg Gly Ile Ile Thr Ser Lys
        35                  40                  45

<210> SEQ ID NO 60
<211> LENGTH: 26
<212> TYPE: PRT
<213> ORGANISM: Clostridium botulinum

<400> SEQUENCE: 60

Met Pro Phe Val Asn Lys Gln Phe Asn Tyr Lys Asp Pro Val Asn Gly
1               5                   10                  15

Val Asp Ile Ala Arg Asn Ala Gly Gln Met
            20                  25

<210> SEQ ID NO 61
<211> LENGTH: 46
<212> TYPE: PRT
<213> ORGANISM: Clostridium botulinum

<400> SEQUENCE: 61

Gly Phe Asn Leu Arg Asn Thr Asn Leu Ala Ala His Asn Thr Glu Ile
1               5                   10                  15

Asn Asn Met Asn Phe Thr Lys Leu Lys Asn Phe Thr Gly Leu Phe Glu
            20                  25                  30

Phe Tyr Lys Leu Leu Cys Val Arg Gly Ile Ile Thr Ser Lys
        35                  40                  45

<210> SEQ ID NO 62
<211> LENGTH: 26
<212> TYPE: PRT
<213> ORGANISM: Clostridium botulinum

<400> SEQUENCE: 62

Met Pro Phe Val Asn Lys Gln Phe Asn Val Asn Gly Val Asp Ile Ala
1               5                   10                  15

Tyr Ile Lys Ile Pro Asn Ala Gly Gln Met
            20                  25

<210> SEQ ID NO 63

```
<211> LENGTH: 42
<212> TYPE: PRT
<213> ORGANISM: Clostridium botulinum

<400> SEQUENCE: 63

Gly Phe Asn Leu Arg Asn Thr Asn Leu Ala Ala Asn Phe Asn Gly Gln
1               5                   10                  15

Asn Thr Glu Ile Asn Asn Met Asn Phe Thr Lys Leu Lys Asn Phe Thr
            20                  25                  30

Gly Leu Phe Glu Phe Arg Arg Thr Ser Lys
        35                  40

<210> SEQ ID NO 64
<211> LENGTH: 30
<212> TYPE: PRT
<213> ORGANISM: Clostridium botulinum

<400> SEQUENCE: 64

Met Pro Val Thr Ile Asn Asn Phe Asn Tyr Asn Asp Pro Ile Asp Asn
1               5                   10                  15

Asp Asn Ile Ile Ala Ala Ala Ala Ala Ala Ala Arg Gly Thr
            20                  25                  30

<210> SEQ ID NO 65
<211> LENGTH: 37
<212> TYPE: PRT
<213> ORGANISM: Clostridium botulinum

<400> SEQUENCE: 65

Tyr Thr Ile Pro Pro Gly Phe Asn Ile Ser Asp Lys Asn Met Gly Lys
1               5                   10                  15

Glu Tyr Arg Gly Gln Asn Lys Ala Ile Asn Lys Gln Ala Tyr Glu Glu
            20                  25                  30

Ile Ser Lys Glu His
        35

<210> SEQ ID NO 66
<211> LENGTH: 26
<212> TYPE: PRT
<213> ORGANISM: Clostridium botulinum

<400> SEQUENCE: 66

Met Pro Ala Phe Asn Tyr Asn Asp Pro Ile Asp Asn Asp Asn Ile Ile
1               5                   10                  15

Met Met Glu Pro Pro Phe Ala Arg Gly Thr
            20                  25

<210> SEQ ID NO 67
<211> LENGTH: 49
<212> TYPE: PRT
<213> ORGANISM: Clostridium botulinum

<400> SEQUENCE: 67

Tyr Thr Ile Glu Glu Gly Phe Asn Ile Ser Asp Lys Asn Met Gly Lys
1               5                   10                  15

Glu Tyr Arg Gly Gln Asn Lys Ala Ala Ala Ala Ala Ala Ala Glu Glu
            20                  25                  30

Ile Lys Glu His Leu Ala Val Tyr Lys Ile Gln Met Cys Lys Ser Val
        35                  40                  45

Lys
```

```
<210> SEQ ID NO 68
<211> LENGTH: 20
<212> TYPE: PRT
<213> ORGANISM: Clostridium botulinum

<400> SEQUENCE: 68

Met Pro Val Thr Ile Asn Asn Phe Asn Arg Met Met Glu Pro Pro Phe
1               5                   10                  15

Ala Arg Gly Thr
            20

<210> SEQ ID NO 69
<211> LENGTH: 44
<212> TYPE: PRT
<213> ORGANISM: Clostridium botulinum

<400> SEQUENCE: 69

Tyr Thr Ile Glu Glu Gly Phe Asn Ile Ser Asp Lys Asn Met Gly Lys
1               5                   10                  15

Glu Tyr Arg Gly Gln Asn Lys Ala Ile Asn Lys Gln Ala Tyr Ala Ala
            20                  25                  30

Ala Ala Ala Ala Ile Gln Met Cys Lys Ser Val Lys
        35                  40

<210> SEQ ID NO 70
<211> LENGTH: 21
<212> TYPE: PRT
<213> ORGANISM: Clostridium botulinum

<400> SEQUENCE: 70

Met Ser Asp Pro Val Asp Asn Lys Asn Ile Leu Tyr Leu Asp Thr His
1               5                   10                  15

Leu Asn Thr Leu Ala
            20

<210> SEQ ID NO 71
<211> LENGTH: 47
<212> TYPE: PRT
<213> ORGANISM: Clostridium botulinum

<400> SEQUENCE: 71

Asn Ile Pro Lys Ser Asn Leu Asn Val Leu Phe Met Gly Gln Asn Leu
1               5                   10                  15

Ser Arg Asn Pro Ala Leu Arg Lys Val Asn Pro Glu Asn Met Leu Ala
            20                  25                  30

Ala Ala Cys His Lys Ala Ile Asp Gly Arg Ser Leu Tyr Asn Lys
        35                  40                  45

<210> SEQ ID NO 72
<211> LENGTH: 26
<212> TYPE: PRT
<213> ORGANISM: Clostridium botulinum

<400> SEQUENCE: 72

Met Thr Arg Pro Val Lys Asp Asp Pro Val Asn Asp Asn Asp Ile Leu
1               5                   10                  15

Tyr Leu Arg Ile Pro Gln Asn Lys Leu Ile
            20                  25

<210> SEQ ID NO 73
<211> LENGTH: 44
```

```
<212> TYPE: PRT
<213> ORGANISM: Clostridium botulinum

<400> SEQUENCE: 73

Tyr Thr Ile Arg Asp Gly Phe Asn Leu Thr Asn Lys Gly Phe Asn Ile
1               5                   10                  15

Glu Asn Ser Gly Gln Asn Ile Glu Arg Asn Pro Ala Leu Gln Lys Leu
            20                  25                  30

Asp Leu Pro Pro Lys Val Cys Leu Arg Leu Thr Lys
        35                  40

<210> SEQ ID NO 74
<211> LENGTH: 31
<212> TYPE: PRT
<213> ORGANISM: Clostridium botulinum

<400> SEQUENCE: 74

Met Pro Lys Ile Asn Ser Pro Pro Asn Tyr Asn Asp Pro Val Asn Asp
1               5                   10                  15

Arg Thr Ile Leu Tyr Ile Lys Pro Gly Gly Cys Gln Glu Phe Tyr
            20                  25                  30

<210> SEQ ID NO 75
<211> LENGTH: 50
<212> TYPE: PRT
<213> ORGANISM: Clostridium botulinum

<400> SEQUENCE: 75

Gly Tyr Asn Ile Asn Asn Leu Lys Val Asn Phe Arg Gly Gln Asn Ala
1               5                   10                  15

Asn Leu Asn Pro Arg Ile Ile Thr Pro Ile Thr Gly Arg Gly Leu Val
            20                  25                  30

Lys Lys Ala Ala Ala Ala Cys Lys Asn Ile Val Ser Val Lys Gly Ile
        35                  40                  45

Arg Lys
    50

<210> SEQ ID NO 76
<211> LENGTH: 33
<212> TYPE: PRT
<213> ORGANISM: Clostridium botulinum

<400> SEQUENCE: 76

Met Pro Lys Ile Asn Ser Phe Asn Tyr Asn Asp Pro Ala Ala Ala Ala
1               5                   10                  15

Asn Asp Arg Thr Ile Leu Tyr Ile Lys Pro Gly Gly Cys Gln Glu Phe
            20                  25                  30

Tyr

<210> SEQ ID NO 77
<211> LENGTH: 47
<212> TYPE: PRT
<213> ORGANISM: Clostridium botulinum

<400> SEQUENCE: 77

Gly Tyr Asn Ile Asn Asn Leu Lys Val Asn Phe Arg Gly Gln Asn Ala
1               5                   10                  15

Asn Leu Asn Pro Arg Ile Ile Thr Pro Ile Thr Gly Arg Gly Leu Val
            20                  25                  30

His Arg Phe Cys Lys Asn Ile Val Ser Val Lys Gly Ile Arg Lys
```

35                  40                  45

<210> SEQ ID NO 78
<211> LENGTH: 30
<212> TYPE: PRT
<213> ORGANISM: Clostridium botulinum

<400> SEQUENCE: 78

Met Pro Lys Ile Asn Ser Phe Asn Tyr Asn Asp Pro Val Asn Asp Arg
1               5                   10                  15

Thr Ile Leu Lys Ile Lys Pro Gly Gly Cys Lys Glu Phe Tyr
            20                  25                  30

<210> SEQ ID NO 79
<211> LENGTH: 33
<212> TYPE: PRT
<213> ORGANISM: Clostridium botulinum

<400> SEQUENCE: 79

Gly Tyr Asn Ile Asn Asn Leu Lys Val Asn Phe Arg Gly Gln Asn Ala
1               5                   10                  15

Asn Leu Asn Pro Arg Ile Ile Thr Pro Ile Thr Gly Arg Gly Leu Pro
            20                  25                  30

Pro

<210> SEQ ID NO 80
<211> LENGTH: 24
<212> TYPE: PRT
<213> ORGANISM: Clostridium botulinum

<400> SEQUENCE: 80

Met Pro Asn Tyr Asn Asp Pro Val Asn Asp Asp Thr Ile Leu Tyr Met
1               5                   10                  15

Gln Ile Pro Tyr Glu Glu Lys Ser
            20

<210> SEQ ID NO 81
<211> LENGTH: 48
<212> TYPE: PRT
<213> ORGANISM: Clostridium botulinum

<400> SEQUENCE: 81

Thr Val Ser Glu Gly Phe Asn Ile Gly Asn Leu Ala Val Asn Asn Arg
1               5                   10                  15

Gly Gln Ser Ile Lys Leu Asn Pro Lys Ile Ile Asp Ser Ile Pro Asp
            20                  25                  30

Lys Gly Ala Ala Ala Ala Ala Cys Lys Ser Val Ile Pro Arg Lys
            35                  40                  45

<210> SEQ ID NO 82
<211> LENGTH: 26
<212> TYPE: PRT
<213> ORGANISM: Clostridium botulinum

<400> SEQUENCE: 82

Met Pro Val Asn Ile Pro Pro Asp Pro Ile Asn Asn Asp Asp Ile Ile
1               5                   10                  15

Met Met Glu Pro Phe Asn Asp Pro Gly Pro
            20                  25

<210> SEQ ID NO 83

```
<211> LENGTH: 32
<212> TYPE: PRT
<213> ORGANISM: Clostridium botulinum

<400> SEQUENCE: 83

Gln Asn Glu Gly Phe Asn Ile Ala Ser Lys Asn Leu Thr Glu Phe Asn
1               5                   10                  15

Gly Gln Asn Lys Ala Val Asn Lys Glu Ala Tyr Ala Ala Ala Ala Ala
            20                  25                  30

<210> SEQ ID NO 84
<211> LENGTH: 22
<212> TYPE: PRT
<213> ORGANISM: Clostridium botulinum

<400> SEQUENCE: 84

Met Tyr Lys Asp Pro Val Asn Gly Val Asp Ile Ala Tyr Ile Lys Ile
1               5                   10                  15

Pro Asn Ala Gly Gln Met
            20

<210> SEQ ID NO 85
<211> LENGTH: 38
<212> TYPE: PRT
<213> ORGANISM: Clostridium botulinum

<400> SEQUENCE: 85

Gly Phe Asn Leu Arg Asn Thr Asn Leu Ala Ala Phe Asn Gly Gln Asn
1               5                   10                  15

Thr Glu Ile Asn Asn Met Asn Phe Thr Lys Leu Lys Asn Phe Thr Gly
            20                  25                  30

Leu Phe Glu Phe Tyr Lys
        35

<210> SEQ ID NO 86
<211> LENGTH: 24
<212> TYPE: PRT
<213> ORGANISM: Clostridium botulinum

<400> SEQUENCE: 86

Met Pro Phe Val Asn Lys Gln Val Asn Gly Val Asp Ile Ala Tyr Ile
1               5                   10                  15

Lys Ile Pro Asn Ala Gly Gln Met
            20

<210> SEQ ID NO 87
<211> LENGTH: 39
<212> TYPE: PRT
<213> ORGANISM: Clostridium botulinum

<400> SEQUENCE: 87

Gly Phe Asn Leu Arg Asn Thr Asn Leu Ala Ala Phe Asn Gly Gln Asn
1               5                   10                  15

Thr Glu Ile Asn Asn Met Asn Phe Thr Lys Leu Lys Leu Leu Cys Val
            20                  25                  30

Arg Gly Ile Ile Thr Ser Lys
        35

<210> SEQ ID NO 88
<211> LENGTH: 24
<212> TYPE: PRT
<213> ORGANISM: Clostridium botulinum
```

```
<400> SEQUENCE: 88

Met Pro Phe Val Asn Lys Gln Phe Asn Tyr Lys Asp Pro Ala Tyr Ile
1               5                   10                  15

Lys Ile Pro Asn Ala Gly Gln Met
            20

<210> SEQ ID NO 89
<211> LENGTH: 41
<212> TYPE: PRT
<213> ORGANISM: Clostridium botulinum

<400> SEQUENCE: 89

Gly Phe Asn Leu Arg Asn Thr Asn Leu Ala Ala Phe Asn Gly Gln Asn
1               5                   10                  15

Thr Glu Ile Asn Asn Met Asn Gly Leu Phe Glu Phe Tyr Lys Leu Leu
            20                  25                  30

Cys Val Arg Gly Ile Ile Thr Ser Lys
        35                  40

<210> SEQ ID NO 90
<211> LENGTH: 20
<212> TYPE: PRT
<213> ORGANISM: Clostridium botulinum

<400> SEQUENCE: 90

Met Pro Phe Val Asn Lys Gln Phe Asn Tyr Lys Asp Pro Val Asn Gly
1               5                   10                  15

Val Asp Ile Ala
            20

<210> SEQ ID NO 91
<211> LENGTH: 32
<212> TYPE: PRT
<213> ORGANISM: Clostridium botulinum

<400> SEQUENCE: 91

Gly Phe Asn Leu Arg Asn Asn Thr Glu Ile Asn Asn Met Asn Gly Leu
1               5                   10                  15

Phe Glu Phe Tyr Lys Leu Leu Cys Val Arg Gly Ile Ile Thr Ser Lys
            20                  25                  30

<210> SEQ ID NO 92
<211> LENGTH: 23
<212> TYPE: PRT
<213> ORGANISM: Clostridium botulinum

<400> SEQUENCE: 92

Met Pro Val Thr Ile Asn Asn Phe Asn Tyr Asn Asp Pro Ile Asp Asn
1               5                   10                  15

Asp Asn Ile Ile Met Met Glu
            20

<210> SEQ ID NO 93
<211> LENGTH: 45
<212> TYPE: PRT
<213> ORGANISM: Clostridium botulinum

<400> SEQUENCE: 93

Tyr Thr Ile Ile Ser Asp Lys Asn Met Gly Lys Glu Tyr Arg Gly Gln
1               5                   10                  15
```

-continued

Asn Lys Ala Ile Asn Lys Gln Ala Tyr Glu Glu Ile Ser Lys Glu His
             20                  25                  30

Leu Ala Val Tyr Lys Ile Gln Met Cys Lys Ser Val Lys
         35                  40                  45

<210> SEQ ID NO 94
<211> LENGTH: 20
<212> TYPE: PRT
<213> ORGANISM: Clostridium botulinum

<400> SEQUENCE: 94

Met Pro Val Thr Ile Asn Asn Phe Asn Tyr Asn Asp Glu Pro Pro Phe
1               5                   10                  15

Ala Arg Gly Thr
         20

<210> SEQ ID NO 95
<211> LENGTH: 42
<212> TYPE: PRT
<213> ORGANISM: Clostridium botulinum

<400> SEQUENCE: 95

Tyr Thr Ile Glu Glu Gly Phe Asn Ile Ser Asp Gly Gln Asn Lys Ala
1               5                   10                  15

Ile Asn Lys Gln Ala Tyr Glu Glu Ile Ser Lys Glu His Leu Ala Val
             20                  25                  30

Tyr Lys Ile Gln Met Cys Lys Ser Val Lys
         35                  40

<210> SEQ ID NO 96
<211> LENGTH: 21
<212> TYPE: PRT
<213> ORGANISM: Clostridium botulinum

<400> SEQUENCE: 96

Met Pro Asn Asp Pro Ile Asp Asn Asp Asn Ile Ile Met Met Glu Pro
1               5                   10                  15

Phe Ala Arg Gly Thr
             20

<210> SEQ ID NO 97
<211> LENGTH: 30
<212> TYPE: PRT
<213> ORGANISM: Clostridium botulinum

<400> SEQUENCE: 97

Tyr Thr Ile Glu Glu Gly Phe Asn Ile Ser Asp Gly Gln Asn Lys Ala
1               5                   10                  15

Ile Asn Lys Gln Ala Lys Ile Gln Met Cys Lys Ser Val Lys
             20                  25                  30

<210> SEQ ID NO 98
<211> LENGTH: 23
<212> TYPE: PRT
<213> ORGANISM: Clostridium botulinum

<400> SEQUENCE: 98

Met Pro Ile Ser Asp Pro Val Asp Asn Lys Asn Ile Leu Tyr Leu Asp
1               5                   10                  15

Thr His Leu Asn Thr Leu Ala
             20

```
<210> SEQ ID NO 99
<211> LENGTH: 40
<212> TYPE: PRT
<213> ORGANISM: Clostridium botulinum

<400> SEQUENCE: 99

Asn Ile Pro Lys Ser Asn Leu Asn Val Leu Phe Met Gly Gln Asn Leu
1               5                   10                  15

Ser Arg Asn Pro Ala Leu Arg Lys Val Lys Phe Cys His Lys Ala Ile
            20                  25                  30

Asp Gly Arg Ser Leu Tyr Asn Lys
        35                  40

<210> SEQ ID NO 100
<211> LENGTH: 20
<212> TYPE: PRT
<213> ORGANISM: Clostridium botulinum

<400> SEQUENCE: 100

Met Thr Trp Val Asn Asp Asn Asp Ile Leu Tyr Leu Arg Ile Pro Gln
1               5                   10                  15

Asn Lys Leu Ile
            20

<210> SEQ ID NO 101
<211> LENGTH: 33
<212> TYPE: PRT
<213> ORGANISM: Clostridium botulinum

<400> SEQUENCE: 101

Tyr Thr Ile Arg Asp Gly Phe Asn Leu Thr Asn Lys Gly Phe Asn Ile
1               5                   10                  15

Glu Arg Asn Pro Ala Asp Leu Phe Thr Lys Val Cys Leu Arg Leu Thr
            20                  25                  30

Lys

<210> SEQ ID NO 102
<211> LENGTH: 22
<212> TYPE: PRT
<213> ORGANISM: Clostridium botulinum

<400> SEQUENCE: 102

Met Pro Asp Pro Val Asn Asp Arg Thr Ile Leu Tyr Ile Lys Pro Gly
1               5                   10                  15

Gly Cys Gln Glu Phe Tyr
            20

<210> SEQ ID NO 103
<211> LENGTH: 40
<212> TYPE: PRT
<213> ORGANISM: Clostridium botulinum

<400> SEQUENCE: 103

Gly Tyr Asn Ile Asn Asn Leu Lys Val Asn Phe Arg Gly Gln Asn Ala
1               5                   10                  15

Asn Leu Asn Pro Arg Ile Ile Thr Pro Ile Arg Phe Cys Lys Asn Ile
            20                  25                  30

Val Ser Val Lys Gly Ile Arg Lys
        35                  40
```

```
<210> SEQ ID NO 104
<211> LENGTH: 20
<212> TYPE: PRT
<213> ORGANISM: Clostridium botulinum

<400> SEQUENCE: 104

Met Pro Lys Ile Asn Ser Phe Asn Tyr Asn Ile Lys Pro Gly Gly Cys
1               5                   10                  15

Gln Glu Phe Tyr
            20

<210> SEQ ID NO 105
<211> LENGTH: 44
<212> TYPE: PRT
<213> ORGANISM: Clostridium botulinum

<400> SEQUENCE: 105

Gly Tyr Asn Ile Asn Asn Gly Gln Asn Ala Asn Leu Asn Pro Arg Ile
1               5                   10                  15

Ile Thr Pro Ile Thr Gly Arg Gly Arg Val Lys Lys Ile Ile Arg Phe
            20                  25                  30

Cys Lys Asn Ile Val Ser Val Lys Gly Ile Arg Lys
        35                  40

<210> SEQ ID NO 106
<211> LENGTH: 22
<212> TYPE: PRT
<213> ORGANISM: Clostridium botulinum

<400> SEQUENCE: 106

Met Pro Lys Ile Asn Ser Phe Asn Tyr Asn Asp Pro Val Asn Asp Arg
1               5                   10                  15

Thr Ile Leu Tyr Ile Lys
            20

<210> SEQ ID NO 107
<211> LENGTH: 42
<212> TYPE: PRT
<213> ORGANISM: Clostridium botulinum

<400> SEQUENCE: 107

Gly Tyr Asn Ile Asn Asn Leu Lys Val Asn Phe Arg Gly Gln Asn Ala
1               5                   10                  15

Asn Leu Asn Pro Arg Ile Ile Thr Pro Ile Thr Gly Arg Gly Arg Val
            20                  25                  30

Lys Lys Ile Ile Arg Lys Gly Ile Arg Lys
        35                  40

<210> SEQ ID NO 108
<211> LENGTH: 25
<212> TYPE: PRT
<213> ORGANISM: Clostridium botulinum

<400> SEQUENCE: 108

Met Pro Val Ala Ile Asn Ser Phe Asn Tyr Asn Asp Pro Val Asn Asp
1               5                   10                  15

Asp Thr Ile Leu Tyr Met Gln Ile Pro
            20                  25

<210> SEQ ID NO 109
<211> LENGTH: 41
<212> TYPE: PRT
```

-continued

<213> ORGANISM: Clostridium botulinum

<400> SEQUENCE: 109

Thr Val Ser Glu Gly Asn Ile Gly Asn Leu Ala Val Asn Asn Arg Gly
1               5                   10                  15

Gln Ser Ile Lys Leu Asn Pro Lys Ile Ile Asp Ser Ile Pro Asp Lys
            20                  25                  30

Phe Cys Lys Ser Val Ile Pro Arg Lys
        35                  40

<210> SEQ ID NO 110
<211> LENGTH: 38
<212> TYPE: PRT
<213> ORGANISM: Clostridium botulinum

<400> SEQUENCE: 110

Gln Asn Glu Gly Phe Asn Ile Ala Ser Lys Asn Leu Lys Thr Glu Phe
1               5                   10                  15

Asn Gly Gln Asn Lys Ala Val Asn Lys Glu Ala Arg Ile Ala Met Cys
            20                  25                  30

Lys Pro Val Met Tyr Lys
        35

<210> SEQ ID NO 111
<211> LENGTH: 423
<212> TYPE: PRT
<213> ORGANISM: Clostridium botulinum

<400> SEQUENCE: 111

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65              70                  75                  80

Asp Arg Phe Leu Lys Ile Val Thr Lys Ile Phe Asn Arg Ile Asn Asn
            85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145             150                 155                 160

Asn Ser Ser Asn Ile Ser Leu Arg Asn Asn Tyr Met Pro Ser Asn His
            165                 170                 175

Gly Phe Gly Ser Ile Ala Ile Val Thr Phe Ser Pro Glu Tyr Ser Phe
        180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

```
Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
            245                 250                 255

Gly Thr Asp Leu Asn Ile Ile Thr Ser Ala Gln Ser Asn Asp Ile Tyr
        260                 265                 270

Thr Asn Leu Leu Ala Asp Tyr Lys Lys Ile Ala Ser Lys Leu Ser Lys
    275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
            325                 330                 335

Phe Asp Leu Ala Thr Lys Phe Gln Val Lys Cys Arg Gln Thr Tyr Ile
        340                 345                 350

Gly Gln Tyr Lys Tyr Phe Lys Leu Ser Asn Leu Leu Asn Asp Ser Ile
    355                 360                 365

Tyr Asn Ile Ser Glu Gly Tyr Asn Ile Asn Asn Leu Lys Val Asn Phe
370                 375                 380

Arg Gly Gln Asn Ala Asn Leu Asn Pro Arg Ile Ile Thr Pro Ile Thr
385                 390                 395                 400

Gly Lys Asn Phe Thr Gly Leu Phe Glu Phe Tyr Lys Leu Leu Cys Val
            405                 410                 415

Arg Gly Ile Ile Thr Ser Lys
        420

<210> SEQ ID NO 112
<211> LENGTH: 441
<212> TYPE: PRT
<213> ORGANISM: Clostridium botulinum

<400> SEQUENCE: 112

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Phe Gln Thr Leu Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
```

-continued

```
                165                 170                 175
Ile Gln Asn His Phe Ala Ser Arg Glu Gly Phe Gly Gly Ile Met Gln
            180                 185                 190
Met Lys Phe Cys Pro Glu Tyr Val Ser Val Phe Asn Asn Val Gln Glu
        195                 200                 205
Asn Lys Gly Ala Ser Ile Phe Asn Arg Arg Gly Tyr Phe Ser Asp Pro
    210                 215                 220
Ala Leu Ile Leu Met His Glu Leu Ile His Val Leu His Gly Leu Tyr
225                 230                 235                 240
Gly Ile Lys Val Asp Asp Leu Pro Ile Val Pro Asn Glu Lys Lys Phe
                245                 250                 255
Phe Met Gln Ser Thr Asp Thr Ile Gln Ala Glu Glu Leu Tyr Thr Phe
            260                 265                 270
Gly Gly Gln Asp Pro Ser Ile Ile Ser Pro Ser Thr Asp Lys Ser Ile
        275                 280                 285
Tyr Asp Lys Val Leu Gln Asn Phe Arg Gly Ile Val Asp Arg Leu Asn
    290                 295                 300
Lys Val Leu Val Cys Ile Ser Asp Pro Asn Ile Asn Ile Asn Ile Tyr
305                 310                 315                 320
Lys Asn Lys Phe Lys Asp Lys Tyr Lys Phe Val Glu Asp Ser Glu Gly
                325                 330                 335
Lys Tyr Ser Ile Asp Val Glu Ser Phe Asn Lys Leu Tyr Lys Ser Leu
            340                 345                 350
Met Leu Gly Phe Thr Glu Ile Asn Ile Ala Glu Asn Tyr Lys Ile Lys
        355                 360                 365
Thr Arg Ala Ser Tyr Phe Ser Asp Ser Leu Pro Pro Val Lys Ile Lys
    370                 375                 380
Asn Leu Leu Asp Asn Glu Ile Tyr Thr Ile Glu Glu Gly Phe Asn Ile
385                 390                 395                 400
Ser Asp Lys Asn Met Gly Lys Glu Tyr Arg Gly Gln Asn Lys Ala Ile
                405                 410                 415
Asn Lys Gln Ala Tyr Glu Glu Ile Ser Lys Glu His Leu Ala Val Tyr
            420                 425                 430
Lys Ile Gln Met Cys Lys Ser Val Lys
        435                 440

<210> SEQ ID NO 113
<211> LENGTH: 423
<212> TYPE: PRT
<213> ORGANISM: Clostridium botulinum

<400> SEQUENCE: 113

Met Pro Phe Val Asn Lys Gln Phe Asn Asn Asp Pro Val Asn Asp Arg
1               5                   10                  15
Thr Ile Leu Tyr Ile Lys Pro Gly Gly Cys Gln Glu Phe Tyr Lys Ser
            20                  25                  30
Phe Asn Ile Met Lys Asn Ile Trp Ile Ile Pro Glu Arg Asn Val Ile
        35                  40                  45
Gly Thr Thr Pro Gln Asp Phe His Pro Pro Thr Ser Leu Lys Asn Gly
    50                  55                  60
Asp Ser Ser Tyr Tyr Asp Pro Asn Tyr Leu Gln Ser Asp Glu Glu Lys
65                  70                  75                  80
Asp Arg Phe Leu Lys Ile Val Thr Lys Ile Phe Asn Arg Ile Asn Asn
                85                  90                  95
```

-continued

```
Asn Leu Ser Gly Gly Ile Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Lys Asn Phe Thr Gly Leu Phe Glu Phe Tyr Lys Leu Leu Cys Val
                405                 410                 415

Arg Gly Ile Ile Thr Ser Lys
            420

<210> SEQ ID NO 114
<211> LENGTH: 441
<212> TYPE: PRT
<213> ORGANISM: Clostridium botulinum

<400> SEQUENCE: 114

Met Pro Phe Val Asn Lys Gln Phe Asn Tyr Asn Asp Pro Ile Asp Asn
1               5                   10                  15

Asp Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45
```

```
Arg Tyr Thr Phe Gly Tyr Lys Pro Glu Asp Phe Asn Lys Ser Ser Gly
     50                  55                  60

Ile Phe Asn Arg Asp Val Cys Glu Tyr Tyr Asp Pro Asp Tyr Leu Asn
 65                  70                  75                  80

Thr Asn Asp Lys Lys Asn Ile Phe Phe Gln Thr Leu Ile Lys Leu Phe
                 85                  90                  95

Asn Arg Ile Lys Ser Lys Pro Leu Gly Glu Lys Leu Leu Glu Met Ile
                100                 105                 110

Ile Asn Gly Ile Pro Tyr Leu Gly Asp Arg Arg Val Pro Leu Glu Glu
                115                 120                 125

Phe Asn Thr Asn Ile Ala Ser Val Thr Val Asn Lys Leu Ile Ser Asn
            130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
                180                 185                 190

Met Lys Phe Cys Pro Glu Tyr Val Ser Val Phe Asn Asn Val Gln Glu
            195                 200                 205

Asn Lys Gly Ala Ser Ile Phe Asn Arg Arg Gly Tyr Phe Ser Asp Pro
            210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Thr Ile Gln Ala Glu Glu Leu Tyr Thr Phe
            260                 265                 270

Gly Gly Gln Asp Pro Ser Ile Ile Ser Pro Ser Thr Asp Lys Ser Ile
            275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asn Lys Leu Tyr Lys Ser Leu
            340                 345                 350

Met Leu Gly Phe Thr Glu Ile Asn Ile Ala Glu Asn Tyr Lys Ile Lys
            355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asn Met Gly Lys Glu Tyr Arg Gly Gln Asn Lys Ala Ile
                405                 410                 415

Asn Lys Gln Lys Asn Phe Thr Gly Leu Phe Glu Phe Tyr Lys Leu Leu
            420                 425                 430

Cys Val Arg Gly Ile Ile Thr Ser Lys
            435                 440

<210> SEQ ID NO 115
<211> LENGTH: 436
```

```
<212> TYPE: PRT
<213> ORGANISM: Clostridium botulinum

<400> SEQUENCE: 115

Met Pro Phe Val Asn Lys Gln Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asn Pro Ser Asp Phe Asp Pro Pro Ala Ser
    50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Lys Val Leu Leu Gln Glu Ile Ser
            100                 105                 110

Tyr Ala Lys Pro Tyr Leu Gly Asn Asp His Thr Pro Ile Asp Glu Phe
        115                 120                 125

Ser Pro Val Thr Arg Thr Thr Ser Val Asn Ile Lys Leu Ser Thr Asn
    130                 135                 140

Val Glu Ser Ser Met Leu Leu Asn Leu Leu Val Leu Gly Ala Gly Pro
145                 150                 155                 160

Asp Ile Phe Glu Ser Cys Cys Tyr Pro Val Arg Lys Leu Ile Asp Pro
                165                 170                 175

Asp Val Val Tyr Asp Pro Ser Asn Tyr Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly His Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Glu Glu Thr Ile Glu Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Glu Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ser Asp Leu Ala Asn Lys Phe Lys Val Lys Cys Arg Asn Thr Tyr
        355                 360                 365

Phe Ile Lys Tyr Glu Phe Leu Lys Val Pro Asn Leu Leu Asp Asp Asp
    370                 375                 380

Ile Tyr Thr Val Ser Glu Gly Phe Asn Ile Gly Asn Leu Ala Val Asn
385                 390                 395                 400
```

```
Asn Arg Gly Gln Ser Ile Lys Leu Asn Pro Lys Ile Ile Asp Lys Asn
            405                 410                 415

Phe Thr Gly Leu Phe Glu Phe Tyr Lys Leu Leu Cys Val Arg Gly Ile
            420                 425                 430

Ile Thr Ser Lys
        435

<210> SEQ ID NO 116
<211> LENGTH: 483
<212> TYPE: PRT
<213> ORGANISM: Clostridium botulinum

<400> SEQUENCE: 116

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Tyr Asn Asp Pro Ile Asp Asn Asp Asn Ile Ile Met Met
    50                  55                  60

Glu Pro Pro Phe Ala Arg Gly Thr Gly Arg Tyr Tyr Lys Ala Phe Lys
65                  70                  75                  80

Ile Thr Asp Arg Ile Trp Ile Ile Pro Glu Arg Tyr Thr Phe Gly Tyr
                85                  90                  95

Lys Pro Glu Asp Phe Asn Lys Ser Ser Gly Ile Phe Asn Arg Asp Val
            100                 105                 110

Cys Glu Tyr Tyr Asp Pro Asp Tyr Leu Asn Thr Asn Asp Lys Lys Asn
        115                 120                 125

Ile Phe Phe Gln Thr Leu Ile Lys Leu Phe Asn Arg Ile Lys Ser Lys
    130                 135                 140

Pro Leu Gly Glu Lys Leu Leu Glu Met Ile Ile Asn Gly Ile Pro Tyr
145                 150                 155                 160

Leu Gly Asp Arg Arg Val Pro Leu Glu Glu Phe Asn Thr Asn Ile Ala
                165                 170                 175

Ser Val Thr Val Asn Lys Leu Ile Ser Asn Pro Gly Glu Val Glu Arg
            180                 185                 190

Lys Lys Gly Ile Phe Ala Asn Leu Ile Ile Phe Gly Pro Gly Pro Val
        195                 200                 205

Leu Asn Glu Asn Glu Thr Ile Asp Ile Gly Ile Gln Asn His Phe Ala
    210                 215                 220

Ser Arg Glu Gly Phe Gly Gly Ile Met Gln Met Lys Phe Cys Pro Glu
225                 230                 235                 240

Tyr Val Ser Val Phe Asn Asn Val Gln Glu Asn Lys Gly Ala Ser Ile
                245                 250                 255

Phe Asn Arg Arg Gly Tyr Phe Ser Asp Pro Ala Leu Ile Leu Met His
            260                 265                 270

Glu Leu Ile His Val Leu His Gly Leu Tyr Gly Ile Lys Val Asp Asp
        275                 280                 285

Leu Pro Ile Val Pro Asn Glu Lys Lys Phe Phe Met Gln Ser Thr Asp
    290                 295                 300

Thr Ile Gln Ala Glu Glu Leu Tyr Thr Phe Gly Gly Gln Asp Pro Ser
305                 310                 315                 320

Ile Ile Ser Pro Ser Thr Asp Lys Ser Ile Tyr Asp Lys Val Leu Gln
```

```
                325                 330                 335
Asn Phe Arg Gly Ile Val Asp Arg Leu Asn Lys Val Leu Val Cys Ile
                340                 345                 350

Ser Asp Pro Asn Ile Asn Ile Asn Ile Tyr Lys Asn Lys Phe Lys Asp
                355                 360                 365

Lys Tyr Lys Phe Val Glu Asp Ser Glu Gly Lys Tyr Ser Ile Asp Val
                370                 375                 380

Glu Ser Phe Asn Lys Leu Tyr Lys Ser Leu Met Leu Gly Phe Thr Glu
385                 390                 395                 400

Ile Asn Ile Ala Glu Asn Tyr Lys Ile Lys Thr Arg Ala Ser Tyr Phe
                405                 410                 415

Ser Asp Ser Leu Pro Pro Val Lys Ile Lys Asn Leu Leu Asp Asn Glu
                420                 425                 430

Ile Tyr Thr Ile Glu Glu Gly Phe Asn Ile Ser Asp Lys Asn Met Gly
                435                 440                 445

Lys Glu Tyr Arg Gly Gln Asn Lys Ala Ile Asn Lys Gln Ala Tyr Glu
                450                 455                 460

Glu Ile Ser Lys Glu His Leu Ala Val Tyr Lys Ile Gln Met Cys Lys
465                 470                 475                 480

Ser Val Lys

<210> SEQ ID NO 117
<211> LENGTH: 458
<212> TYPE: PRT
<213> ORGANISM: Clostridium botulinum

<400> SEQUENCE: 117

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
                20                  25                  30

Phe Asn Ile Met Lys Asn Ile Trp Ile Ile Pro Glu Arg Asn Val Ile
                35                  40                  45

Gly Thr Thr Pro Gln Asp Phe His Pro Pro Thr Ser Leu Lys Asn Gly
                50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
                100                 105                 110

Tyr Leu Gly Asn Asp Asn Thr Pro Asp Asn Gln Phe His Ile Gly Asp
                115                 120                 125

Ala Ser Ala Val Glu Ile Lys Phe Ser Asn Gly Ser Gln Asp Ile Leu
                130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
                180                 185                 190

Arg Phe Asn Asp Asn Ser Met Asn Glu Phe Ile Gln Asp Pro Ala Leu
                195                 200                 205

Thr Leu Met His Glu Leu Ile His Ser Leu His Gly Leu Tyr Gly Ala
```

```
            210                 215                 220
Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
                260                 265                 270

Thr Asn Leu Leu Ala Asp Tyr Lys Lys Ile Ala Ser Lys Leu Ser Lys
                275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
                340                 345                 350

Gly Gln Tyr Lys Tyr Phe Lys Leu Ser Asn Leu Leu Asn Asp Ser Ile
                355                 360                 365

Tyr Asn Ile Ser Glu Gly Tyr Asn Ile Asn Asn Leu Lys Val Asn Phe
                370                 375                 380

Arg Gly Gln Asn Ala Asn Leu Asn Pro Arg Ile Ile Thr Pro Gly Phe
385                 390                 395                 400

Asn Leu Arg Asn Thr Asn Leu Ala Ala Asn Phe Asn Gly Gln Asn Thr
                405                 410                 415

Glu Ile Asn Asn Met Asn Phe Thr Lys Leu Lys Asn Phe Thr Gly Leu
                420                 425                 430

Phe Glu Phe Tyr Lys Leu Leu Cys Val Arg Gly Ile Ile Thr Ser Lys
                435                 440                 445

Asn Ile Val Ser Val Lys Gly Ile Arg Lys
            450                 455

<210> SEQ ID NO 118
<211> LENGTH: 443
<212> TYPE: PRT
<213> ORGANISM: Clostridium botulinum

<400> SEQUENCE: 118

Met Pro Lys Ile Asn Ser Phe Asn Tyr Met Pro Phe Val Asn Lys Gln
1               5                   10                  15

Phe Asn Tyr Lys Asp Pro Val Asn Gly Val Asp Ile Ala Tyr Ile Lys
                20                  25                  30

Ile Pro Asn Ala Gly Gln Met Tyr Ile Lys Pro Gly Gly Cys Gln Glu
            35                  40                  45

Phe Tyr Lys Ser Phe Asn Ile Met Lys Asn Ile Trp Ile Ile Pro Glu
        50                  55                  60

Arg Asn Val Ile Gly Thr Thr Pro Gln Asp Phe His Pro Pro Thr Ser
65                  70                  75                  80

Leu Lys Asn Gly Asp Ser Ser Tyr Tyr Asp Pro Asn Tyr Leu Gln Ser
                85                  90                  95

Asp Glu Glu Lys Asp Arg Phe Leu Lys Ile Val Thr Lys Ile Phe Asn
                100                 105                 110

Arg Ile Asn Asn Asn Leu Ser Gly Gly Ile Leu Leu Glu Glu Leu Ser
            115                 120                 125
```

Lys Ala Asn Pro Tyr Leu Gly Asn Asp Asn Thr Pro Asp Asn Gln Phe
            130                 135                 140

His Ile Gly Asp Ala Ser Ala Val Glu Ile Lys Phe Ser Asn Gly Ser
145                 150                 155                 160

Gln Asp Ile Leu Leu Pro Asn Val Ile Met Gly Ala Glu Pro Asp
            165                 170                 175

Leu Phe Glu Thr Asn Ser Ser Asn Ile Ser Leu Arg Asn Asn Tyr Met
            180                 185                 190

Pro Ser Asn His Gly Phe Gly Ser Ile Ala Ile Val Thr Phe Ser Pro
            195                 200                 205

Glu Tyr Ser Phe Arg Phe Asn Asp Asn Ser Met Asn Glu Phe Ile Gln
        210                 215                 220

Asp Pro Ala Leu Thr Leu Met His Glu Leu Ile His Ser Leu His Gly
225                 230                 235                 240

Leu Tyr Gly Ala Lys Gly Ile Thr Thr Lys Tyr Thr Ile Thr Gln Lys
                245                 250                 255

Gln Asn Pro Leu Ile Thr Asn Ile Arg Gly Thr Asn Ile Glu Glu Phe
            260                 265                 270

Leu Thr Phe Gly Gly Thr Asp Leu Asn Ile Ile Thr Ser Ala Gln Ser
        275                 280                 285

Asn Asp Ile Tyr Thr Asn Leu Leu Ala Asp Tyr Lys Lys Ile Ala Ser
290                 295                 300

Lys Leu Ser Lys Val Gln Val Ser Asn Pro Leu Leu Asn Pro Tyr Lys
305                 310                 315                 320

Asp Val Phe Glu Ala Lys Tyr Gly Leu Asp Lys Asp Ala Ser Gly Ile
                325                 330                 335

Tyr Ser Val Asn Ile Asn Lys Phe Asn Asp Ile Phe Lys Lys Leu Tyr
            340                 345                 350

Ser Phe Thr Glu Phe Asp Leu Ala Thr Lys Phe Gln Val Lys Cys Arg
        355                 360                 365

Gln Thr Tyr Ile Gly Gln Tyr Lys Tyr Phe Lys Leu Ser Asn Leu Leu
    370                 375                 380

Asn Asp Ser Ile Tyr Asn Ile Ser Glu Gly Phe Asn Leu Arg Asn Thr
385                 390                 395                 400

Asn Leu Ala Ala Asn Phe Asn Gly Gln Asn Thr Glu Ile Asn Asn Met
                405                 410                 415

Asn Phe Thr Lys Leu Lys Asn Phe Thr Gly Leu Phe Glu Phe Tyr Lys
            420                 425                 430

Leu Leu Cys Val Arg Gly Ile Ile Thr Ser Lys
        435                 440

<210> SEQ ID NO 119
<211> LENGTH: 461
<212> TYPE: PRT
<213> ORGANISM: Clostridium botulinum

<400> SEQUENCE: 119

Met Pro Val Thr Ile Asn Asn Phe Asn Met Pro Phe Val Asn Lys Gln
1               5                   10                  15

Phe Asn Tyr Lys Asp Pro Val Asn Gly Val Asp Ile Ala Tyr Ile Lys
            20                  25                  30

Ile Pro Asn Ala Gly Gln Met Ile Met Glu Pro Pro Phe Ala Arg
        35                  40                  45

Gly Thr Gly Arg Tyr Tyr Lys Ala Phe Lys Ile Thr Asp Arg Ile Trp
    50                  55                  60

-continued

```
Ile Ile Pro Glu Arg Tyr Thr Phe Gly Tyr Lys Pro Glu Asp Phe Asn
 65                  70                  75                  80

Lys Ser Ser Gly Ile Phe Asn Arg Asp Val Cys Glu Tyr Tyr Asp Pro
                 85                  90                  95

Asp Tyr Leu Asn Thr Asn Asp Lys Lys Asn Ile Phe Phe Gln Thr Leu
            100                 105                 110

Ile Lys Leu Phe Asn Arg Ile Lys Ser Lys Pro Leu Gly Glu Lys Leu
        115                 120                 125

Leu Glu Met Ile Ile Asn Gly Ile Pro Tyr Leu Gly Asp Arg Arg Val
    130                 135                 140

Pro Leu Glu Glu Phe Asn Thr Asn Ile Ala Ser Val Thr Val Asn Lys
145                 150                 155                 160

Leu Ile Ser Asn Pro Gly Glu Val Glu Arg Lys Gly Ile Phe Ala
                165                 170                 175

Asn Leu Ile Ile Phe Gly Pro Gly Pro Val Leu Asn Glu Asn Glu Thr
            180                 185                 190

Ile Asp Ile Gly Ile Gln Asn His Phe Ala Ser Arg Glu Gly Phe Gly
        195                 200                 205

Gly Ile Met Gln Met Lys Phe Cys Pro Glu Tyr Val Ser Val Phe Asn
    210                 215                 220

Asn Val Gln Glu Asn Lys Gly Ala Ser Ile Phe Asn Arg Arg Gly Tyr
225                 230                 235                 240

Phe Ser Asp Pro Ala Leu Ile Leu Met His Glu Leu Ile His Val Leu
                245                 250                 255

His Gly Leu Tyr Gly Ile Lys Val Asp Asp Leu Pro Ile Val Pro Asn
            260                 265                 270

Glu Lys Lys Phe Phe Met Gln Ser Thr Asp Thr Ile Gln Ala Glu Glu
        275                 280                 285

Leu Tyr Thr Phe Gly Gly Gln Asp Pro Ser Ile Ile Ser Pro Ser Thr
    290                 295                 300

Asp Lys Ser Ile Tyr Asp Lys Val Leu Gln Asn Phe Arg Gly Ile Val
305                 310                 315                 320

Asp Arg Leu Asn Lys Val Leu Val Cys Ile Ser Asp Pro Asn Ile Asn
                325                 330                 335

Ile Asn Ile Tyr Lys Asn Lys Phe Lys Asp Lys Tyr Lys Phe Val Glu
            340                 345                 350

Asp Ser Glu Gly Lys Tyr Ser Ile Asp Val Glu Ser Phe Asn Lys Leu
        355                 360                 365

Tyr Lys Ser Leu Met Leu Gly Phe Thr Glu Ile Asn Ile Ala Glu Asn
    370                 375                 380

Tyr Lys Ile Lys Thr Arg Ala Ser Tyr Phe Ser Asp Ser Leu Pro Pro
385                 390                 395                 400

Val Lys Ile Lys Asn Leu Leu Asp Asn Glu Ile Gly Phe Asn Leu Arg
                405                 410                 415

Asn Thr Asn Leu Ala Ala Asn Phe Asn Gly Gln Asn Thr Glu Ile Asn
            420                 425                 430

Asn Met Asn Phe Thr Lys Leu Lys Asn Phe Thr Gly Leu Phe Glu Phe
        435                 440                 445

Tyr Lys Leu Leu Cys Val Arg Gly Ile Ile Thr Ser Lys
    450                 455                 460

<210> SEQ ID NO 120
<211> LENGTH: 456
```

<212> TYPE: PRT
<213> ORGANISM: Clostridium botulinum

<400> SEQUENCE: 120

| | | | | | | | | | | | | | | |
|---|---|---|---|---|---|---|---|---|---|---|---|---|---|---|
| Met | Pro | Val | Ala | Ile | Asn | Ser | Phe | Asn | Met | Pro | Phe | Val | Asn | Lys | Gln |
| 1 | | | | 5 | | | | | 10 | | | | | 15 | |
| Phe | Asn | Tyr | Lys | Asp | Pro | Val | Asn | Gly | Val | Asp | Ile | Ala | Tyr | Ile | Lys |
| | | | 20 | | | | | 25 | | | | | 30 | | |
| Ile | Pro | Asn | Ala | Gly | Gln | Met | Leu | Tyr | Met | Gln | Ile | Pro | Tyr | Glu | Glu |
| | | | 35 | | | | | 40 | | | | | 45 | | |
| Lys | Ser | Lys | Lys | Tyr | Tyr | Lys | Ala | Phe | Glu | Ile | Met | Arg | Asn | Val | Trp |
| | 50 | | | | | 55 | | | | | 60 | | | | |
| Ile | Ile | Pro | Glu | Arg | Asn | Thr | Ile | Gly | Thr | Asn | Pro | Ser | Asp | Phe | Asp |
| 65 | | | | | 70 | | | | | 75 | | | | | 80 |
| Pro | Pro | Ala | Ser | Leu | Lys | Asn | Gly | Ser | Ser | Ala | Tyr | Tyr | Asp | Pro | Asn |
| | | | | 85 | | | | | 90 | | | | | 95 | |
| Tyr | Leu | Thr | Thr | Asp | Ala | Glu | Lys | Asp | Arg | Tyr | Leu | Lys | Thr | Thr | Ile |
| | | | | 100 | | | | | 105 | | | | | 110 | |
| Lys | Leu | Phe | Lys | Arg | Ile | Asn | Ser | Asn | Pro | Ala | Gly | Lys | Val | Leu | Leu |
| | | | 115 | | | | | 120 | | | | | 125 | | |
| Gln | Glu | Ile | Ser | Tyr | Ala | Lys | Pro | Tyr | Leu | Gly | Asn | Asp | His | Thr | Pro |
| | 130 | | | | | 135 | | | | | 140 | | | | |
| Ile | Asp | Glu | Phe | Ser | Pro | Val | Thr | Arg | Thr | Thr | Ser | Val | Asn | Ile | Lys |
| 145 | | | | | 150 | | | | | 155 | | | | | 160 |
| Leu | Ser | Thr | Asn | Val | Glu | Ser | Ser | Met | Leu | Leu | Asn | Leu | Leu | Val | Leu |
| | | | | 165 | | | | | 170 | | | | | 175 | |
| Gly | Ala | Gly | Pro | Asp | Ile | Phe | Glu | Ser | Cys | Cys | Tyr | Pro | Val | Arg | Lys |
| | | | 180 | | | | | 185 | | | | | 190 | | |
| Leu | Ile | Asp | Pro | Asp | Val | Val | Tyr | Asp | Pro | Ser | Asn | Tyr | Gly | Phe | Gly |
| | | 195 | | | | | 200 | | | | | 205 | | | |
| Ser | Ile | Asn | Ile | Val | Thr | Phe | Ser | Pro | Glu | Tyr | Glu | Tyr | Thr | Phe | Asn |
| | 210 | | | | | 215 | | | | | 220 | | | | |
| Asp | Ile | Ser | Gly | Gly | His | Asn | Ser | Ser | Thr | Glu | Ser | Phe | Ile | Ala | Asp |
| 225 | | | | | 230 | | | | | 235 | | | | | 240 |
| Pro | Ala | Ile | Ser | Leu | Ala | His | Glu | Leu | Ile | His | Ala | Leu | His | Gly | Leu |
| | | | | 245 | | | | | 250 | | | | | 255 | |
| Tyr | Gly | Ala | Arg | Gly | Val | Thr | Tyr | Glu | Glu | Thr | Ile | Glu | Val | Lys | Gln |
| | | | 260 | | | | | 265 | | | | | 270 | | |
| Ala | Pro | Leu | Met | Ile | Ala | Glu | Lys | Pro | Ile | Arg | Leu | Glu | Glu | Phe | Leu |
| | | 275 | | | | | 280 | | | | | 285 | | | |
| Thr | Phe | Gly | Gly | Gln | Asp | Leu | Asn | Ile | Ile | Thr | Ser | Ala | Met | Lys | Glu |
| | 290 | | | | | 295 | | | | | 300 | | | | |
| Lys | Ile | Tyr | Asn | Asn | Leu | Leu | Ala | Asn | Tyr | Glu | Lys | Ile | Ala | Thr | Arg |
| 305 | | | | | 310 | | | | | 315 | | | | | 320 |
| Leu | Ser | Glu | Val | Asn | Ser | Ala | Pro | Pro | Glu | Tyr | Asp | Ile | Asn | Glu | Tyr |
| | | | | 325 | | | | | 330 | | | | | 335 | |
| Lys | Asp | Tyr | Phe | Gln | Trp | Lys | Tyr | Gly | Leu | Asp | Lys | Asn | Ala | Asp | Gly |
| | | | 340 | | | | | 345 | | | | | 350 | | |
| Ser | Tyr | Thr | Val | Asn | Glu | Asn | Lys | Phe | Asn | Glu | Ile | Tyr | Lys | Lys | Leu |
| | | 355 | | | | | 360 | | | | | 365 | | | |
| Tyr | Ser | Phe | Thr | Glu | Ser | Asp | Leu | Ala | Asn | Lys | Phe | Lys | Val | Lys | Cys |
| | 370 | | | | | 375 | | | | | 380 | | | | |
| Arg | Asn | Thr | Tyr | Phe | Ile | Lys | Tyr | Glu | Phe | Leu | Lys | Val | Pro | Asn | Leu |
| 385 | | | | | 390 | | | | | 395 | | | | | 400 |

```
Leu Asp Asp Asp Ile Tyr Gly Phe Asn Leu Arg Asn Thr Asn Leu Ala
            405                 410                 415

Ala Asn Phe Asn Gly Gln Asn Thr Glu Ile Asn Asn Met Asn Phe Thr
        420                 425                 430

Lys Leu Lys Asn Phe Thr Gly Leu Phe Glu Phe Tyr Lys Leu Leu Cys
        435                 440                 445

Val Arg Gly Ile Ile Thr Ser Lys
    450                 455

<210> SEQ ID NO 121
<211> LENGTH: 449
<212> TYPE: PRT
<213> ORGANISM: Clostridium botulinum

<400> SEQUENCE: 121

Met Pro Lys Ile Asn Ser Phe Asn Tyr Asn Asp Pro Val Thr Ile Asn
1               5                   10                  15

Asn Phe Asn Tyr Asp Arg Thr Ile Leu Tyr Ile Lys Pro Gly Gly Cys
            20                  25                  30

Gln Glu Phe Tyr Lys Ser Phe Asn Ile Met Lys Asn Ile Trp Ile Ile
        35                  40                  45

Pro Glu Arg Asn Val Ile Gly Thr Thr Pro Gln Asp Phe His Pro Pro
    50                  55                  60

Thr Ser Leu Lys Asn Gly Asp Ser Ser Tyr Tyr Asp Pro Asn Tyr Leu
65                  70                  75                  80

Gln Ser Asp Glu Glu Lys Asp Arg Phe Leu Lys Ile Val Thr Lys Ile
                85                  90                  95

Phe Asn Arg Ile Asn Asn Asn Leu Ser Gly Gly Ile Leu Leu Glu Glu
            100                 105                 110

Leu Ser Lys Ala Asn Pro Tyr Leu Gly Asn Asp Asn Thr Pro Asp Asn
        115                 120                 125

Gln Phe His Ile Gly Asp Ala Ser Ala Val Glu Ile Lys Phe Ser Asn
    130                 135                 140

Gly Ser Gln Asp Ile Leu Leu Pro Asn Val Ile Ile Met Gly Ala Glu
145                 150                 155                 160

Pro Asp Leu Phe Glu Thr Asn Ser Ser Asn Ile Ser Leu Arg Asn Asn
                165                 170                 175

Tyr Met Pro Ser Asn His Gly Phe Gly Ser Ile Ala Ile Val Thr Phe
            180                 185                 190

Ser Pro Glu Tyr Ser Phe Arg Phe Asn Asp Asn Ser Met Asn Glu Phe
        195                 200                 205

Ile Gln Asp Pro Ala Leu Thr Leu Met His Glu Leu Ile His Ser Leu
    210                 215                 220

His Gly Leu Tyr Gly Ala Lys Gly Ile Thr Thr Lys Tyr Thr Ile Thr
225                 230                 235                 240

Gln Lys Gln Asn Pro Leu Ile Thr Asn Ile Arg Gly Thr Asn Ile Glu
                245                 250                 255

Glu Phe Leu Thr Phe Gly Gly Thr Asp Leu Asn Ile Ile Thr Ser Ala
            260                 265                 270

Gln Ser Asn Asp Ile Tyr Thr Asn Leu Leu Ala Asp Tyr Lys Lys Ile
        275                 280                 285

Ala Ser Lys Leu Ser Lys Val Gln Val Ser Asn Pro Leu Leu Asn Pro
    290                 295                 300

Tyr Lys Asp Val Phe Glu Ala Lys Tyr Gly Leu Asp Lys Asp Ala Ser
```

-continued

```
              305                 310                 315                 320
Gly Ile Tyr Ser Val Asn Ile Asn Lys Phe Asn Asp Ile Phe Lys Lys
                    325                 330                 335

Leu Tyr Ser Phe Thr Glu Phe Asp Leu Ala Thr Lys Phe Gln Val Lys
                    340                 345                 350

Cys Arg Gln Thr Tyr Ile Gly Gln Tyr Lys Tyr Phe Lys Leu Ser Asn
                    355                 360                 365

Leu Leu Asn Asp Ser Ile Tyr Asn Ile Ser Glu Gly Tyr Asn Ile Asn
            370                 375                 380

Asn Leu Lys Val Asn Phe Arg Gly Gln Asn Ala Asn Leu Asn Pro Arg
385                 390                 395                 400

Ile Ile Thr Pro Ile Thr Gly Arg Gly Leu Val Lys Lys Ile Ile Arg
                    405                 410                 415

Phe Cys Lys Asn Asn Met Asn Phe Thr Lys Leu Lys Asn Phe Thr Gly
                    420                 425                 430

Leu Phe Glu Phe Tyr Lys Leu Leu Cys Val Arg Gly Ile Ile Thr Ser
                    435                 440                 445

Lys
```

<210> SEQ ID NO 122
<211> LENGTH: 459
<212> TYPE: PRT
<213> ORGANISM: Clostridium botulinum

<400> SEQUENCE: 122

```
Met Pro Val Ala Ile Asn Ser Phe Asn Tyr Asn Asp Val Thr Ile Asn
1               5                   10                  15

Asn Phe Asn Tyr Thr Ile Leu Tyr Met Gln Ile Pro Tyr Glu Glu Lys
                20                  25                  30

Ser Lys Lys Tyr Tyr Lys Ala Phe Glu Ile Met Arg Asn Val Trp Ile
            35                  40                  45

Ile Pro Glu Arg Asn Thr Ile Gly Thr Asn Pro Ser Asp Phe Asp Pro
        50                  55                  60

Pro Ala Ser Leu Lys Asn Gly Ser Ser Ala Tyr Tyr Asp Pro Asn Tyr
65                  70                  75                  80

Leu Thr Thr Asp Ala Glu Lys Asp Arg Tyr Leu Lys Thr Thr Ile Lys
                85                  90                  95

Leu Phe Lys Arg Ile Asn Ser Asn Pro Ala Gly Lys Val Leu Leu Gln
                100                 105                 110

Glu Ile Ser Tyr Ala Lys Pro Tyr Leu Gly Asn Asp His Thr Pro Ile
            115                 120                 125

Asp Glu Phe Ser Pro Val Thr Arg Thr Thr Ser Val Asn Ile Lys Leu
        130                 135                 140

Ser Thr Asn Val Glu Ser Ser Met Leu Leu Asn Leu Leu Val Leu Gly
145                 150                 155                 160

Ala Gly Pro Asp Ile Phe Glu Ser Cys Cys Tyr Pro Val Arg Lys Leu
                165                 170                 175

Ile Asp Pro Asp Val Val Tyr Asp Pro Ser Asn Tyr Gly Phe Gly Ser
                180                 185                 190

Ile Asn Ile Val Thr Phe Ser Pro Glu Tyr Glu Tyr Thr Phe Asn Asp
            195                 200                 205

Ile Ser Gly Gly His Asn Ser Ser Thr Glu Ser Phe Ile Ala Asp Pro
        210                 215                 220

Ala Ile Ser Leu Ala His Glu Leu Ile His Ala Leu His Gly Leu Tyr
```

```
                    225                 230                 235                 240

Gly Ala Arg Gly Val Thr Tyr Glu Glu Thr Ile Glu Val Lys Gln Ala
                        245                 250                 255

Pro Leu Met Ile Ala Glu Lys Pro Ile Arg Leu Glu Glu Phe Leu Thr
                        260                 265                 270

Phe Gly Gly Gln Asp Leu Asn Ile Ile Thr Ser Ala Met Lys Glu Lys
                        275                 280                 285

Ile Tyr Asn Asn Leu Leu Ala Asn Tyr Glu Lys Ile Ala Thr Arg Leu
                        290                 295                 300

Ser Glu Val Asn Ser Ala Pro Pro Glu Tyr Asp Ile Asn Glu Tyr Lys
            305                 310                 315                 320

Asp Tyr Phe Gln Trp Lys Tyr Gly Leu Asp Lys Asn Ala Asp Gly Ser
                        325                 330                 335

Tyr Thr Val Asn Glu Asn Lys Phe Asn Glu Ile Tyr Lys Lys Leu Tyr
                        340                 345                 350

Ser Phe Thr Glu Ser Asp Leu Ala Asn Lys Phe Lys Val Lys Cys Arg
                        355                 360                 365

Asn Thr Tyr Phe Ile Lys Tyr Glu Phe Leu Lys Val Pro Asn Leu Leu
                        370                 375                 380

Asp Asp Asp Ile Tyr Thr Val Ser Glu Gly Phe Asn Ile Gly Asn Leu
            385                 390                 395                 400

Ala Val Asn Asn Arg Gly Gln Ser Ile Lys Leu Asn Pro Lys Ile Ile
                        405                 410                 415

Asp Ser Ile Pro Asp Lys Gly Leu Val Glu Lys Asn Asn Met Asn Phe
                        420                 425                 430

Thr Lys Leu Lys Asn Phe Thr Gly Leu Phe Glu Phe Tyr Lys Leu Leu
                        435                 440                 445

Cys Val Arg Gly Ile Ile Thr Ser Lys Arg Lys
                        450                 455

<210> SEQ ID NO 123
<211> LENGTH: 12
<212> TYPE: PRT
<213> ORGANISM: Clostridium botulinum

<400> SEQUENCE: 123

Met Pro Phe Val Asn Lys Gln Phe Asn Tyr Lys Asp
1               5                   10

<210> SEQ ID NO 124
<211> LENGTH: 11
<212> TYPE: PRT
<213> ORGANISM: Clostridium botulinum

<400> SEQUENCE: 124

Pro Phe Val Asn Lys Gln Phe Asn Tyr Lys Asp
1               5                   10

<210> SEQ ID NO 125
<211> LENGTH: 4
<212> TYPE: PRT
<213> ORGANISM: Clostridium botulinum

<400> SEQUENCE: 125

Met Tyr Lys Asp
1

<210> SEQ ID NO 126
```

```
<211> LENGTH: 7
<212> TYPE: PRT
<213> ORGANISM: Clostridium botulinum
<220> FEATURE:
<221> NAME/KEY: misc_feature
<222> LOCATION: (1)..(1)
<223> OTHER INFORMATION: Xaa is any amino acid.
<220> FEATURE:
<221> NAME/KEY: misc_feature
<222> LOCATION: (3)..(5)
<223> OTHER INFORMATION: Xaa is any amino acid.

<400> SEQUENCE: 126

Xaa Asp Xaa Xaa Xaa Leu Leu
1               5

<210> SEQ ID NO 127
<211> LENGTH: 7
<212> TYPE: PRT
<213> ORGANISM: Clostridium botulinum
<220> FEATURE:
<221> NAME/KEY: misc_feature
<222> LOCATION: (1)..(1)
<223> OTHER INFORMATION: Xaa is any amino acid.
<220> FEATURE:
<221> NAME/KEY: misc_feature
<222> LOCATION: (3)..(5)
<223> OTHER INFORMATION: Xaa is any amino acid.

<400> SEQUENCE: 127

Xaa Glu Xaa Xaa Xaa Leu Leu
1               5

<210> SEQ ID NO 128
<211> LENGTH: 7
<212> TYPE: PRT
<213> ORGANISM: Clostridium botulinum
<220> FEATURE:
<221> NAME/KEY: misc_feature
<222> LOCATION: (1)..(1)
<223> OTHER INFORMATION: Xaa is any amino acid.
<220> FEATURE:
<221> NAME/KEY: misc_feature
<222> LOCATION: (3)..(5)
<223> OTHER INFORMATION: Xaa is any amino acid.

<400> SEQUENCE: 128

Xaa Asp Xaa Xaa Xaa Leu Ile
1               5

<210> SEQ ID NO 129
<211> LENGTH: 7
<212> TYPE: PRT
<213> ORGANISM: Clostridium botulinum
<220> FEATURE:
<221> NAME/KEY: misc_feature
<222> LOCATION: (1)..(1)
<223> OTHER INFORMATION: Xaa is any amino acid.
<220> FEATURE:
<221> NAME/KEY: misc_feature
<222> LOCATION: (3)..(5)
<223> OTHER INFORMATION: Xaa is any amino acid.

<400> SEQUENCE: 129

Xaa Asp Xaa Xaa Xaa Leu Met
1               5

<210> SEQ ID NO 130
<211> LENGTH: 7
<212> TYPE: PRT
<213> ORGANISM: Clostridium botulinum
```

```
<220> FEATURE:
<221> NAME/KEY: misc_feature
<222> LOCATION: (1)..(1)
<223> OTHER INFORMATION: Xaa is any amino acid.
<220> FEATURE:
<221> NAME/KEY: misc_feature
<222> LOCATION: (3)..(5)
<223> OTHER INFORMATION: Xaa is any amino acid.

<400> SEQUENCE: 130

Xaa Glu Xaa Xaa Xaa Leu Ile
1               5

<210> SEQ ID NO 131
<211> LENGTH: 7
<212> TYPE: PRT
<213> ORGANISM: Clostridium botulinum
<220> FEATURE:
<221> NAME/KEY: misc_feature
<222> LOCATION: (1)..(1)
<223> OTHER INFORMATION: Xaa is any amino acid.
<220> FEATURE:
<221> NAME/KEY: misc_feature
<222> LOCATION: (3)..(5)
<223> OTHER INFORMATION: Xaa is any amino acid.

<400> SEQUENCE: 131

Xaa Glu Xaa Xaa Xaa Ile Leu
1               5

<210> SEQ ID NO 132
<211> LENGTH: 7
<212> TYPE: PRT
<213> ORGANISM: Clostridium botulinum
<220> FEATURE:
<221> NAME/KEY: misc_feature
<222> LOCATION: (1)..(1)
<223> OTHER INFORMATION: Xaa is any amino acid.
<220> FEATURE:
<221> NAME/KEY: misc_feature
<222> LOCATION: (3)..(5)
<223> OTHER INFORMATION: Xaa is any amino acid.

<400> SEQUENCE: 132

Xaa Glu Xaa Xaa Xaa Leu Met
1               5

<210> SEQ ID NO 133
<211> LENGTH: 4
<212> TYPE: PRT
<213> ORGANISM: Clostridium botulinum
<220> FEATURE:
<221> NAME/KEY: misc_feature
<222> LOCATION: (2)..(3)
<223> OTHER INFORMATION: Xaa is any amino acid.
<220> FEATURE:
<221> NAME/KEY: misc_feature
<222> LOCATION: (4)..(4)
<223> OTHER INFORMATION: Xaa is a hydrophobic amino acid.

<400> SEQUENCE: 133

Tyr Xaa Xaa Xaa
1

<210> SEQ ID NO 134
<211> LENGTH: 6
<212> TYPE: PRT
<213> ORGANISM: Clostridium botulinum

<400> SEQUENCE: 134
```

```
Phe Asp Lys Leu Tyr Lys
1               5
```

<210> SEQ ID NO 135
<211> LENGTH: 8
<212> TYPE: PRT
<213> ORGANISM: Clostridium botulinum

<400> SEQUENCE: 135

```
Pro Phe Val Asn Lys Gln Phe Asn
1               5
```

<210> SEQ ID NO 136
<211> LENGTH: 22
<212> TYPE: PRT
<213> ORGANISM: Clostridium botulinum

<400> SEQUENCE: 136

```
Lys Asn Phe Thr Gly Leu Phe Glu Phe Tyr Lys Leu Leu Cys Val Arg
1               5                   10                  15

Gly Ile Ile Thr Ser Lys
            20
```